United States Patent
Boa et al.

(10) Patent No.: US 9,351,852 B2
(45) Date of Patent: *May 31, 2016

(54) ARTIFICIAL DISC DEVICE

(75) Inventors: Qi-Bin Boa, Marquette, MI (US);
Jeffrey L. Trudeau, Marquette, MI (US); Brian Patrick Janowski, Marquette, MI (US); Matthew N. Songer, Marquette, MI (US); Hansen A. Yuan, Fayetteville, NY (US); Thomas S. Kilpela, Marquette, MI (US); Gregory Berrevoets, Skandia, MI (US)

(73) Assignee: PIONEER SURGICAL TECHNOLOGY, INC., Marquette, MI (US)

(*) Notice: Subject to any disclaimer, the term of this patent is extended or adjusted under 35 U.S.C. 154(b) by 129 days.

This patent is subject to a terminal disclaimer.

(21) Appl. No.: 13/585,607

(22) Filed: Aug. 14, 2012

(65) Prior Publication Data
US 2012/0310287 A1    Dec. 6, 2012

Related U.S. Application Data

(60) Division of application No. 10/971,734, filed on Oct. 22, 2004, now Pat. No. 8,241,360, which is a continuation-in-part of application No. 10/282,620, filed on Oct. 29, 2002, now Pat. No. 7,001,433, and a
(Continued)

(51) Int. Cl.
*A61F 2/44* (2006.01)
*A61B 17/88* (2006.01)
(Continued)

(52) U.S. Cl.
CPC .............. *A61F 2/4684* (2013.01); *A61F 2/442* (2013.01); *A61F 2/4425* (2013.01);
(Continued)

(58) Field of Classification Search
CPC ............ A61F 2/4611; A61F 2002/444; A61F 2002/4628
USPC ............................................ 623/17.11, 17.16
See application file for complete search history.

(56) References Cited

U.S. PATENT DOCUMENTS 3,867,728 A    2/1975    Stubstad et al.
3,875,595 A    4/1975    Froning et al.
(Continued)

FOREIGN PATENT DOCUMENTS

CA    2395609    2/2001
CA    2482403    9/2003
(Continued)

OTHER PUBLICATIONS

Bao et al., Artificial Disc Technology, Neurosurg. Focus 9(4), Oct. 2000, 7 pp.
(Continued)

*Primary Examiner* — David H Willse
*Assistant Examiner* — Javier Blanco
(74) *Attorney, Agent, or Firm* — Fitch, Even, Tabin & Flannery LLP

(57) ABSTRACT

An artificial disc device for replacing a damaged nucleus is disclosed. In one form, the device may be inserted in components such that the device may be assembled within and retained by the natural annulus therein. In another form, the device may be inserted into the natural annulus in a collapsed or compressed state or arrangement and then be expanded within and retained by the annulus therein. In a further form, the device may be provided with a releasable connection so that the device may be connected in an insertion configuration and may be released in an operable configuration. Insertion tools and methods are also disclosed.

12 Claims, 30 Drawing Sheets

Related U.S. Application Data continuation-in-part of application No. 10/692,468, filed on Oct. 22, 2003, now Pat. No. 8,388,684.

(60) Provisional application No. 60/382,758, filed on May 23, 2002.

(51) Int. Cl.
*A61F 2/46* (2006.01)
*A61F 2/30* (2006.01)
*A61F 2/48* (2006.01)

(52) U.S. Cl.
CPC .......... *A61F 2/4611* (2013.01); *A61F 2/30742* (2013.01); *A61F 2/30965* (2013.01); *A61F 2002/302* (2013.01); *A61F 2002/305* (2013.01); *A61F 2002/3008* (2013.01); *A61F 2002/30014* (2013.01); *A61F 2002/30016* (2013.01); *A61F 2002/3023* (2013.01); *A61F 2002/3039* (2013.01); *A61F 2002/3052* (2013.01); *A61F 2002/3054* (2013.01); *A61F 2002/3055* (2013.01); *A61F 2002/30113* (2013.01); *A61F 2002/30123* (2013.01); *A61F 2002/30125* (2013.01); *A61F 2002/30133* (2013.01); *A61F 2002/30158* (2013.01); *A61F 2002/30242* (2013.01); *A61F 2002/30245* (2013.01); *A61F 2002/30299* (2013.01); *A61F 2002/30311* (2013.01); *A61F 2002/30327* (2013.01); *A61F 2002/30331* (2013.01); *A61F 2002/30369* (2013.01); *A61F 2002/30387* (2013.01); *A61F 2002/30428* (2013.01); *A61F 2002/30448* (2013.01); *A61F 2002/30462* (2013.01); *A61F 2002/30471* (2013.01); *A61F 2002/30476* (2013.01); *A61F 2002/30485* (2013.01); *A61F 2002/30507* (2013.01); *A61F 2002/30528* (2013.01); *A61F 2002/30538* (2013.01); *A61F 2002/30556* (2013.01); *A61F 2002/30563* (2013.01); *A61F 2002/30565* (2013.01); *A61F 2002/30574* (2013.01); *A61F 2002/30581* (2013.01); *A61F 2002/30583* (2013.01); *A61F 2002/30586* (2013.01); *A61F 2002/30588* (2013.01); *A61F 2002/30604* (2013.01); *A61F 2002/30616* (2013.01); *A61F 2002/30649* (2013.01); *A61F 2002/30662* (2013.01); *A61F 2002/30673* (2013.01); *A61F 2002/30685* (2013.01); *A61F 2002/30738* (2013.01); *A61F 2002/30784* (2013.01); *A61F 2002/30841* (2013.01); *A61F 2002/30919* (2013.01); *A61F 2002/30934* (2013.01); *A61F 2002/30935* (2013.01); *A61F 2002/443* (2013.01); *A61F 2002/444* (2013.01); *A61F 2002/4627* (2013.01); *A61F 2002/4628* (2013.01); *A61F 2002/4681* (2013.01); *A61F 2002/484* (2013.01); *A61F 2210/0085* (2013.01); *A61F 2220/005* (2013.01); *A61F 2220/0025* (2013.01); *A61F 2220/0033* (2013.01); *A61F 2220/0075* (2013.01); *A61F 2220/0091* (2013.01); *A61F 2230/0006* (2013.01); *A61F 2230/0008* (2013.01); *A61F 2230/0015* (2013.01); *A61F 2230/0026* (2013.01); *A61F 2230/0065* (2013.01); *A61F 2230/0069* (2013.01); *A61F 2230/0071* (2013.01); *A61F 2230/0093* (2013.01); *A61F 2250/0006* (2013.01); *A61F 2250/0009* (2013.01); *A61F 2250/0018* (2013.01); *A61F 2250/0019* (2013.01); *A61F 2250/0039* (2013.01); *A61F 2250/0098* (2013.01); *A61F 2310/00017* (2013.01); *A61F 2310/00023* (2013.01); *A61F 2310/00029* (2013.01); *A61F 2310/00179* (2013.01); *A61F 2310/00203* (2013.01); *A61F 2310/00239* (2013.01); *A61F 2310/00574* (2013.01)

(56) References Cited

U.S. PATENT DOCUMENTS

| | | |
|---|---|---|
| 3,975,778 A | 8/1976 | Newton, III |
| 4,021,382 A | 5/1977 | Stoy et al. |
| 4,081,402 A | 3/1978 | Levy et al. |
| 4,147,764 A | 4/1979 | Levy et al. |
| 4,309,777 A | 1/1982 | Patil |
| 4,349,921 A | 9/1982 | Kuntz |
| 4,374,523 A | 2/1983 | Yoon |
| 4,454,612 A | 6/1984 | McDaniel et al. |
| 4,566,466 A | 1/1986 | Ripple et al. |
| 4,650,490 A | 3/1987 | Figgie, III |
| 4,714,469 A | 12/1987 | Kenna |
| 4,728,561 A | 3/1988 | Crocker |
| 4,759,766 A | 7/1988 | Buettner-Janz et al. |
| 4,759,769 A | 7/1988 | Hedman et al. |
| 4,863,476 A | 9/1989 | Shepperd |
| 4,863,477 A | 9/1989 | Monson |
| 4,899,761 A | 2/1990 | Brown et al. |
| 4,917,704 A | 4/1990 | Frey et al. |
| 4,932,969 A | 6/1990 | Frey et al. |
| 4,936,848 A | 6/1990 | Bagby |
| 4,946,378 A | 8/1990 | Hirayama et al. |
| 4,997,432 A | 3/1991 | Keller |
| 5,002,576 A | 3/1991 | Fuhrmann et al. |
| 5,035,716 A | 7/1991 | Downey |
| 5,047,055 A | 9/1991 | Bao et al. |
| 5,071,437 A | 12/1991 | Steffee |
| 5,084,057 A | 1/1992 | Green et al. |
| 5,108,438 A | 4/1992 | Stone |
| 5,127,920 A | 7/1992 | MacArthur |
| 5,133,759 A | 7/1992 | Turner |
| 5,133,772 A | 7/1992 | Hack et al. |
| 5,147,404 A | 9/1992 | Downey |
| 5,171,281 A | 12/1992 | Parsons et al. |
| 5,176,710 A | 1/1993 | Hahn et al. |
| 5,192,326 A | 3/1993 | Bao et al. |
| 5,258,031 A | 11/1993 | Salib et al. |
| 5,258,043 A | 11/1993 | Stone |
| 5,273,742 A | 12/1993 | Gould et al. |
| 5,306,308 A | 4/1994 | Gross et al. |
| 5,306,309 A | 4/1994 | Wagner et al. |
| 5,314,477 A | 5/1994 | Marnay |
| 5,320,625 A | 6/1994 | Bertin |
| 5,320,644 A | 6/1994 | Baumgartner |
| 5,401,269 A | 3/1995 | Buttner-Janz et al. |
| 5,425,773 A | 6/1995 | Boyd et al. |
| 5,443,512 A | 8/1995 | Parr et al. |
| 5,458,642 A | 10/1995 | Beer et al. |
| 5,458,643 A | 10/1995 | Oka et al. |
| 5,462,362 A | 10/1995 | Yuhta et al. |
| 5,480,449 A | 1/1996 | Hamilton et al. |
| 5,507,816 A | 4/1996 | Bullivant |
| 5,514,180 A | 5/1996 | Heggeness et al. |
| 5,522,899 A | 6/1996 | Michelson |
| 5,534,028 A | 7/1996 | Bao et al. |
| 5,542,949 A | 8/1996 | Yoon |
| 5,549,679 A | 8/1996 | Kuslich |
| 5,556,431 A | 9/1996 | Buttner-Janz |
| 5,556,433 A | 9/1996 | Gabriel et al. |
| 5,562,736 A | 10/1996 | Ray et al. |
| 5,562,738 A | 10/1996 | Boyd et al. |
| 5,571,189 A | 11/1996 | Kuslich |
| 5,595,563 A | 1/1997 | Moisdon |
| 5,609,643 A | 3/1997 | Colleran et al. |
| 5,645,596 A | 7/1997 | Kim et al. |
| 5,645,597 A | 7/1997 | Krapiva |
| 5,658,336 A | 8/1997 | Pisharodi |
| 5,665,122 A | 9/1997 | Kambin |

(56) References Cited

U.S. PATENT DOCUMENTS

| | | |
|---|---|---|
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,693,100 A | 12/1997 | Pisharodi |
| 5,702,450 A | 12/1997 | Bisserie |
| 5,716,416 A | 2/1998 | Lin |
| 5,728,762 A | 3/1998 | Reich et al. |
| 5,755,797 A | 5/1998 | Baumgartner |
| 5,755,798 A | 5/1998 | Papavero et al. |
| 5,782,832 A | 7/1998 | Larsen et al. |
| 5,824,093 A | 10/1998 | Ray et al. |
| 5,824,094 A | 10/1998 | Serhan et al. |
| 5,860,980 A | 1/1999 | Axelson, Jr. et al. |
| 5,865,845 A | 2/1999 | Thalgott |
| 5,865,846 A | 2/1999 | Bryan et al. |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,919,235 A | 7/1999 | Husson et al. |
| 5,964,807 A | 10/1999 | Gan et al. |
| 5,969,020 A | 10/1999 | Shalaby et al. |
| 5,976,186 A | 11/1999 | Bao et al. |
| 5,980,572 A | 11/1999 | Kim et al. |
| 6,001,130 A | 12/1999 | Bryan et al. |
| 6,019,793 A | 2/2000 | Perren et al. |
| 6,022,376 A | 2/2000 | Assell et al. |
| 6,039,763 A | 3/2000 | Shelokov |
| RE36,758 E | 6/2000 | Fitz |
| 6,074,390 A | 6/2000 | Zucherman et al. |
| 6,093,205 A | 7/2000 | McLeod et al. |
| 6,093,207 A | 7/2000 | Pisharodi |
| 6,110,210 A | 8/2000 | Norton et al. |
| 6,113,639 A | 9/2000 | Ray et al. |
| 6,127,597 A | 10/2000 | Beyar et al. |
| 6,132,465 A | 10/2000 | Ray et al. |
| 6,136,031 A | 10/2000 | Middleton |
| 6,139,579 A | 10/2000 | Steffee et al. |
| 6,143,031 A | 11/2000 | Knothe et al. |
| 6,146,422 A | 11/2000 | Lawson |
| 6,156,067 A | 12/2000 | Bryan et al. |
| 6,162,252 A | 12/2000 | Kuras et al. |
| 6,179,874 B1 | 1/2001 | Cauthen |
| 6,183,518 B1 | 2/2001 | Ross et al. |
| 6,187,048 B1 | 2/2001 | Milner et al. |
| 6,190,387 B1 | 2/2001 | Zucherman et al. |
| 6,206,924 B1 | 3/2001 | Timm |
| 6,224,630 B1 | 5/2001 | Bao et al. |
| 6,240,926 B1 | 6/2001 | Gan et al. |
| 6,251,140 B1 | 6/2001 | Marino et al. |
| 6,264,695 B1 | 7/2001 | Stoy |
| 6,280,475 B1 | 8/2001 | Bao et al. |
| 6,283,968 B1 | 9/2001 | Mehdizadeh |
| 6,283,998 B1 | 9/2001 | Eaton |
| 6,315,795 B1 | 11/2001 | Scarborough et al. |
| 6,315,797 B1 | 11/2001 | Middleton |
| 6,348,071 B1 | 2/2002 | Steffee et al. |
| 6,352,557 B1 | 3/2002 | Ferree |
| 6,368,350 B1 | 4/2002 | Erickson et al. |
| 6,371,990 B1 | 4/2002 | Ferree |
| 6,375,682 B1 | 4/2002 | Fleischmann et al. |
| 6,395,032 B1 | 5/2002 | Gauchet |
| 6,402,784 B1 | 6/2002 | Wardlaw |
| 6,402,785 B1 | 6/2002 | Zdeblick et al. |
| 6,419,704 B1 | 7/2002 | Ferree |
| 6,428,544 B1 | 8/2002 | Ralph et al. |
| 6,428,575 B2 | 8/2002 | Koo et al. |
| 6,428,579 B1 | 8/2002 | Valentini |
| 6,432,106 B1 | 8/2002 | Fraser |
| 6,432,107 B1 | 8/2002 | Ferree |
| 6,432,140 B1 | 8/2002 | Lin |
| 6,436,098 B1 | 8/2002 | Michelson |
| 6,436,101 B1 | 8/2002 | Hamada |
| 6,436,102 B1 | 8/2002 | Ralph et al. |
| 6,436,140 B1 | 8/2002 | Liu et al. |
| 6,436,141 B2 | 8/2002 | Castro et al. |
| 6,436,142 B1 | 8/2002 | Paes et al. |
| 6,436,146 B1 | 8/2002 | Hassler et al. |
| 6,440,168 B1 | 8/2002 | Cauthen |
| 6,440,170 B1 | 8/2002 | Jackson |
| 6,478,801 B1 | 11/2002 | Ralph et al. |
| 6,478,822 B1 | 11/2002 | Leroux et al. |
| 6,488,716 B1 | 12/2002 | Huang et al. |
| 6,508,839 B1 | 1/2003 | Lambrecht et al. |
| 6,517,580 B1 | 2/2003 | Ramadan et al. |
| 6,527,804 B1 | 3/2003 | Gauchet et al. |
| 6,533,799 B1 | 3/2003 | Bouchier |
| 6,540,785 B1 | 4/2003 | Gill et al. |
| 6,547,823 B2 | 4/2003 | Scarborough et al. |
| 6,562,047 B2 | 5/2003 | Ralph et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,592,624 B1 | 7/2003 | Fraser et al. |
| 6,602,291 B1 | 8/2003 | Ray et al. |
| 6,607,559 B2 | 8/2003 | Ralph et al. |
| 6,610,091 B1 | 8/2003 | Reiley |
| 6,652,533 B2 | 11/2003 | O'Neil |
| 6,669,730 B2 | 12/2003 | Ralph et al. |
| 6,673,113 B2 | 1/2004 | Ralph et al. |
| 6,679,915 B1 | 1/2004 | Cauthen |
| 6,682,562 B2 | 1/2004 | Viart et al. |
| 6,743,257 B2 | 6/2004 | Castro |
| 6,770,095 B2 | 8/2004 | Grinberg et al. |
| 6,783,550 B2 | 8/2004 | MacArthur |
| 6,793,678 B2 | 9/2004 | Hawkins |
| 6,824,565 B2 | 11/2004 | Muhanna et al. |
| 6,863,689 B2 | 3/2005 | Ralph et al. |
| 6,899,716 B2 | 5/2005 | Cragg |
| 6,936,071 B1 | 8/2005 | Marnay et al. |
| 6,984,246 B2 | 1/2006 | Huang |
| 7,001,433 B2 | 2/2006 | Songer et al. |
| 7,156,876 B2 | 1/2007 | Moumene et al. |
| 2001/0010021 A1 | 7/2001 | Boyd et al. |
| 2001/0012938 A1 | 8/2001 | Zucherman et al. |
| 2001/0016772 A1 | 8/2001 | Lee et al. |
| 2001/0016773 A1 | 8/2001 | Serhan et al. |
| 2001/0016776 A1 | 8/2001 | Zucherman et al. |
| 2001/0020476 A1 | 9/2001 | Gan et al. |
| 2001/0027343 A1 | 10/2001 | Keller |
| 2001/0032019 A1 | 10/2001 | Van Dyke et al. |
| 2001/0032020 A1 | 10/2001 | Besselink |
| 2001/0047208 A1 | 11/2001 | Michelson |
| 2001/0051829 A1 | 12/2001 | Middleton |
| 2002/0013600 A1 | 1/2002 | Scribner et al. |
| 2002/0022883 A1 | 2/2002 | Burg |
| 2002/0022888 A1 | 2/2002 | Serhan et al. |
| 2002/0026244 A1 | 2/2002 | Trieu |
| 2002/0029082 A1 | 3/2002 | Muhanna |
| 2002/0029083 A1 | 3/2002 | Zucherman et al. |
| 2002/0035400 A1 | 3/2002 | Bryan et al. |
| 2002/0045942 A1 | 4/2002 | Ham |
| 2002/0045944 A1 | 4/2002 | Muhanna et al. |
| 2002/0049498 A1 | 4/2002 | Yuksel et al. |
| 2002/0065560 A1* | 5/2002 | Varga et al. ................ 623/17.16 |
| 2002/0082608 A1 | 6/2002 | Reiley et al. |
| 2002/0082701 A1 | 6/2002 | Zdeblick et al. |
| 2002/0087480 A1 | 7/2002 | Sauriol et al. |
| 2002/0099444 A1 | 7/2002 | Boyd et al. |
| 2002/0106393 A1 | 8/2002 | Bianchi et al. |
| 2002/0107571 A1 | 8/2002 | Foley |
| 2002/0107572 A1 | 8/2002 | Foley et al. |
| 2002/0107573 A1 | 8/2002 | Steinberg |
| 2002/0111683 A1 | 8/2002 | Ralph et al. |
| 2002/0111687 A1 | 8/2002 | Ralph et al. |
| 2002/0120269 A1 | 8/2002 | Lange |
| 2002/0120270 A1 | 8/2002 | Trieu et al. |
| 2002/0120334 A1 | 8/2002 | Crozet |
| 2002/0120336 A1 | 8/2002 | Santilli |
| 2002/0151979 A1 | 10/2002 | Lambrecht et al. |
| 2002/0156528 A1 | 10/2002 | Gau |

(56) References Cited

U.S. PATENT DOCUMENTS

| | | |
|---|---|---|
| 2002/0165612 A1 | 11/2002 | Gerber et al. |
| 2003/0009226 A1 | 1/2003 | Graf |
| 2003/0009227 A1 | 1/2003 | Lambrecht et al. |
| 2003/0014113 A1 | 1/2003 | Ralph et al. |
| 2003/0014115 A1 | 1/2003 | Ralph et al. |
| 2003/0023311 A1 | 1/2003 | Trieu |
| 2003/0028197 A1 | 2/2003 | Hanson et al. |
| 2003/0028251 A1 | 2/2003 | Mathews |
| 2003/0040799 A1 | 2/2003 | Boyd et al. |
| 2003/0040802 A1 | 2/2003 | Errico et al. |
| 2003/0045939 A1 | 3/2003 | Casutt |
| 2003/0055427 A1 | 3/2003 | Graf |
| 2003/0069586 A1 | 4/2003 | Errico et al. |
| 2003/0069642 A1 | 4/2003 | Ralph et al. |
| 2003/0069643 A1 | 4/2003 | Ralph et al. |
| 2003/0074076 A1 | 4/2003 | Ferree et al. |
| 2003/0078590 A1 | 4/2003 | Errico et al. |
| 2003/0078662 A1 | 4/2003 | Ralph et al. |
| 2003/0093155 A1 | 5/2003 | Lambrecht et al. |
| 2003/0100951 A1 | 5/2003 | Serhan et al. |
| 2003/0130667 A1 | 7/2003 | Lin |
| 2003/0135276 A1 | 7/2003 | Eckman |
| 2003/0135277 A1 | 7/2003 | Bryan et al. |
| 2003/0135278 A1 | 7/2003 | Eckman |
| 2003/0139813 A1* | 7/2003 | Messerli et al. ............ 623/17.11 |
| 2003/0149438 A1 | 8/2003 | Nichols et al. |
| 2003/0176921 A1 | 9/2003 | Lawson |
| 2003/0204260 A1 | 10/2003 | Ferree |
| 2003/0204261 A1 | 10/2003 | Eisermann et al. |
| 2003/0204362 A1 | 10/2003 | Beresford et al. |
| 2003/0208203 A1* | 11/2003 | Lim et al. ........................ 606/61 |
| 2003/0216810 A1 | 11/2003 | Ralph et al. |
| 2003/0220691 A1 | 11/2003 | Songer et al. |
| 2003/0229358 A1 | 12/2003 | Errico et al. |
| 2004/0010316 A1 | 1/2004 | William et al. |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034426 A1 | 2/2004 | Errico |
| 2004/0044410 A1 | 3/2004 | Ferree et al. |
| 2004/0049280 A1 | 3/2004 | Cauthen |
| 2004/0068321 A1 | 4/2004 | Ferree |
| 2004/0082999 A1 | 4/2004 | Mathys et al. |
| 2004/0093082 A1 | 5/2004 | Ferree |
| 2004/0093088 A1 | 5/2004 | Ralph et al. |
| 2004/0098129 A1 | 5/2004 | Lin |
| 2004/0102846 A1 | 5/2004 | Keller et al. |
| 2004/0117019 A1* | 6/2004 | Trieu et al. .................. 623/17.11 |
| 2004/0117022 A1 | 6/2004 | Marnay et al. |
| 2004/0133132 A1 | 7/2004 | Chappuis |
| 2004/0133278 A1 | 7/2004 | Marino et al. |
| 2004/0133280 A1 | 7/2004 | Trieu |
| 2004/0143331 A1 | 7/2004 | Errico et al. |
| 2004/0143332 A1 | 7/2004 | Krueger et al. |
| 2004/0148027 A1 | 7/2004 | Errico et al. |
| 2004/0148028 A1 | 7/2004 | Ferree et al. |
| 2004/0153065 A1* | 8/2004 | Lim ................................ 606/53 |
| 2004/0153157 A1 | 8/2004 | Keller |
| 2004/0153158 A1 | 8/2004 | Errico et al. |
| 2004/0167626 A1 | 8/2004 | Geremakis et al. |
| 2004/0167628 A1 | 8/2004 | Foley |
| 2004/0176843 A1 | 9/2004 | Zubok et al. |
| 2004/0176845 A1 | 9/2004 | Zubok et al. |
| 2004/0176848 A1 | 9/2004 | Zubok et al. |
| 2004/0186577 A1 | 9/2004 | Ferree |
| 2004/0204760 A1 | 10/2004 | Fitz et al. |
| 2004/0220670 A1* | 11/2004 | Eisermann et al. ........ 623/17.14 |
| 2004/0225295 A1 | 11/2004 | Zubok et al. |
| 2005/0021042 A1 | 1/2005 | Marnay et al. |
| 2005/0021143 A1 | 1/2005 | Keller |
| 2005/0021149 A1 | 1/2005 | Borruto et al. |
| 2005/0027360 A1 | 2/2005 | Webb et al. |
| 2005/0033305 A1 | 2/2005 | Schultz |
| 2005/0033437 A1 | 2/2005 | Bao et al. |
| 2005/0033438 A1 | 2/2005 | Schultz et al. |
| 2005/0038445 A1 | 2/2005 | Errico et al. |
| 2005/0038515 A1 | 2/2005 | Kunzler |
| 2005/0038516 A1* | 2/2005 | Spoonamore ............... 623/17.14 |
| 2005/0055097 A1 | 3/2005 | Grunberg et al. |
| 2005/0060034 A1 | 3/2005 | Berry et al. |
| 2005/0060035 A1 | 3/2005 | Errico et al. |
| 2005/0071011 A1 | 3/2005 | Ralph et al. |
| 2005/0071012 A1 | 3/2005 | Serhan et al. |
| 2005/0085911 A1 | 4/2005 | Link |
| 2005/0085917 A1 | 4/2005 | Marnay et al. |
| 2005/0096745 A1* | 5/2005 | Andre et al. ................. 623/17.11 |
| 2005/0113842 A1 | 5/2005 | Bertagnoli et al. |
| 2005/0119752 A1 | 6/2005 | Williams et al. |
| 2005/0131541 A1 | 6/2005 | Trieu |
| 2005/0143820 A1 | 6/2005 | Zucherman et al. |
| 2005/0143824 A1 | 6/2005 | Richelsoph et al. |
| 2005/0154463 A1 | 7/2005 | Trieu |
| 2005/0154464 A1 | 7/2005 | Humphreys et al. |
| 2005/0154466 A1 | 7/2005 | Humphreys et al. |
| 2005/0154468 A1 | 7/2005 | Rivin |
| 2005/0165485 A1 | 7/2005 | Trieu |
| 2005/0192670 A1 | 9/2005 | Zubok et al. |
| 2005/0192671 A1 | 9/2005 | Bao et al. |
| 2005/0203538 A1 | 9/2005 | Lo et al. |
| 2005/0266581 A1 | 12/2005 | Droit et al. |
| 2006/0004453 A1 | 1/2006 | Bartish et al. |
| 2006/0020342 A1 | 1/2006 | Ferree et al. |
| 2006/0041614 A1 | 2/2006 | Oe |
| 2006/0069436 A1 | 3/2006 | Sutton et al. |
| 2006/0212122 A1 | 9/2006 | Perera |
| 2006/0229627 A1 | 10/2006 | Hunt et al. |
| 2006/0235527 A1 | 10/2006 | Buettner-Janz et al. |
| 2006/0235528 A1 | 10/2006 | Buettner-Janz |
| 2006/0235531 A1 | 10/2006 | Buettner-Janz |
| 2006/0241761 A1 | 10/2006 | Gately |
| 2007/0027547 A1 | 2/2007 | Rydell et al. |
| 2007/0100454 A1 | 5/2007 | Burgess et al. |
| 2007/0213461 A1 | 9/2007 | Hu et al. |
| 2007/0225726 A1 | 9/2007 | Dye et al. |
| 2008/0091211 A1 | 4/2008 | Gately |
| 2008/0288081 A1 | 11/2008 | Scrafton et al. |
| 2009/0043390 A1 | 2/2009 | Meisel |
| 2009/0164023 A1 | 6/2009 | Devine |
| 2009/0185904 A1 | 7/2009 | Landberg |
| 2012/0203344 A1 | 8/2012 | Trudeau et al. |

FOREIGN PATENT DOCUMENTS

| | | |
|---|---|---|
| CA | 2548780 | 7/2005 |
| CN | 1697633 | 11/2005 |
| DE | 9000094 U1 | 1/1991 |
| DE | 29911422 U1 | 8/1999 |
| DE | 10130825 | 3/2002 |
| DE | 202005005405 | 6/2005 |
| EP | 0179695 | 4/1986 |
| EP | 0346129 A1 | 12/1989 |
| EP | 0773008 A1 | 5/1997 |
| EP | 0919209 A1 | 6/1999 |
| EP | 1104665 A1 | 6/2001 |
| EP | 1205160 | 5/2002 |
| FR | 2372622 | 6/1978 |
| FR | 2723841 | 3/1996 |
| FR | 2787014 | 6/2000 |
| FR | 2797179 | 2/2001 |
| FR | 2799116 | 4/2001 |
| FR | 2805985 | 9/2001 |
| FR | 2824261 | 11/2002 |
| JP | 63300758 A2 | 12/1988 |
| JP | 1308557 A2 | 12/1989 |
| JP | 01142293 | 4/1990 |
| JP | 02111358 | 4/1990 |
| JP | 2215461 A2 | 8/1990 |
| JP | 2224659 A2 | 9/1990 |
| JP | 2224660 A2 | 9/1990 |
| JP | 03275055 A | 12/1991 |
| JP | 03275056 A | 12/1991 |
| JP | 04303444 A | 10/1992 |
| JP | 05277141 A | 10/1993 |
| JP | 06285099 | 10/1994 |

(56) References Cited

FOREIGN PATENT DOCUMENTS

| | | | |
|---|---|---|---|
| JP | 08098850 | A | 4/1996 |
| JP | 08098851 | A2 | 4/1996 |
| JP | 11009618 | A | 1/1999 |
| JP | 11137585 | A | 5/1999 |
| JP | 2008284348 | | 11/2008 |
| WO | 9011740 | | 10/1990 |
| WO | 9100713 | | 1/1991 |
| WO | 9105521 | | 5/1991 |
| WO | 9116867 | | 11/1991 |
| WO | 9316664 | | 9/1993 |
| WO | 9500082 | | 5/1995 |
| WO | 9601598 | | 1/1996 |
| WO | 9611642 | | 4/1996 |
| WO | 9627339 | | 9/1996 |
| WO | 9805274 | | 2/1998 |
| WO | 9819617 | | 5/1998 |
| WO | 9855053 | | 12/1998 |
| WO | 9911203 | | 3/1999 |
| WO | 9922675 | | 5/1999 |
| WO | 9930651 | | 6/1999 |
| WO | 0013619 | | 3/2000 |
| WO | 0042953 | | 7/2000 |
| WO | 0059412 | | 10/2000 |
| WO | 0115638 | | 3/2001 |
| WO | 0132100 | | 5/2001 |
| WO | 0168003 | | 9/2001 |
| WO | 02087480 | | 11/2002 |
| WO | 03035129 | | 5/2003 |
| WO | 03099172 | | 12/2003 |
| WO | 2005009298 | | 2/2005 |
| WO | 2005041818 | | 5/2005 |
| WO | 2005051240 | | 6/2005 |
| WO | 2006016384 | | 2/2006 |
| WO | 2006061114 | | 6/2006 |

OTHER PUBLICATIONS

Depuy Spine, Inc., Charite Artificial Disc Centreline TDR Instrumentation Surgical Technique, Dec. 2004, 20 pp.
Depuy Spine, Inc., Charite Artificial Disc Product Catalog, Dec. 2004, 16 pp.
European Patent Office, Supplemental EPO Search Report for Application No. 03738960.8, Feb. 20, 2008, 6 pp.
Feder, B., "When FDA Says Yes, but Insurers Say No," The New York Times, Jul. 6, 2005, 2 pp.
Zdeblick, T., et al., "Cervical Interbody Fusion Cages", Spine, vol. 23, No. 7, 1998, 11 pp.
State Intellectual Property Office, First Notification of Office Action for Application No. 200780040650.7, Dec. 15, 2010, 9 pp.
European Patent Office, Supplemental EPO Search Report for Application No. EP07842616, Mar. 20, 2012, 7 pp.
European Patent Office, Supplemental EPO Search Report for Application No. EP04706064, Mar. 22, 2012, 8 pp.
International Searching Authority, International Search Report, corresponding to International Patent Appln. No. PCT/US2007/07517, Apr. 23, 2008, 1 pg.
International Searching Authority, International Search Report, corresponding to International Patent Appln. No. PCT/2007/075693, Jul. 3, 2008, 1 pg.

* cited by examiner

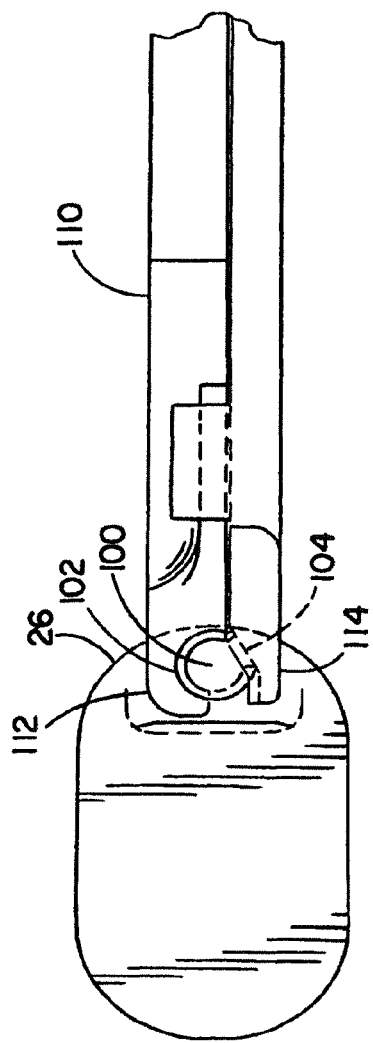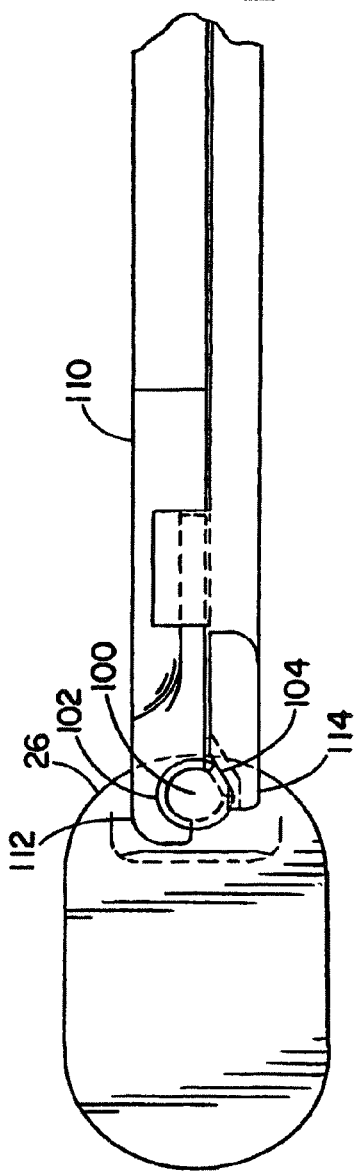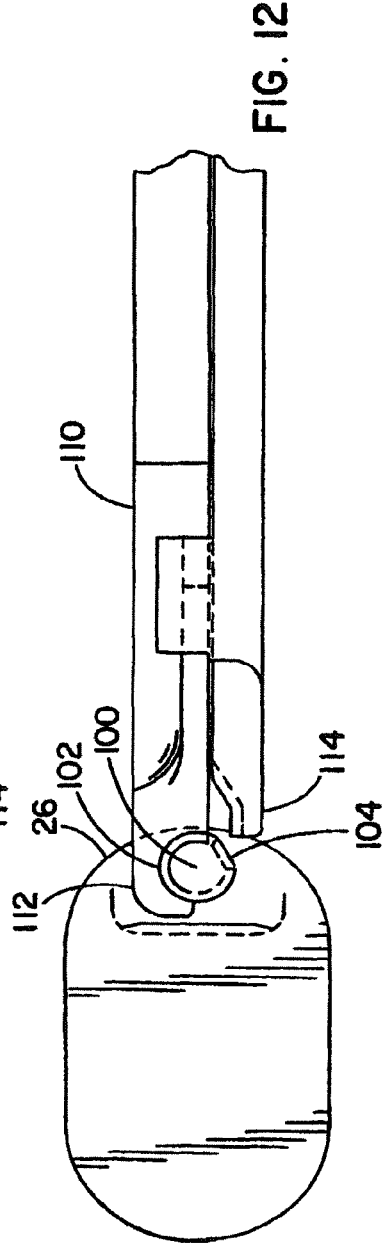

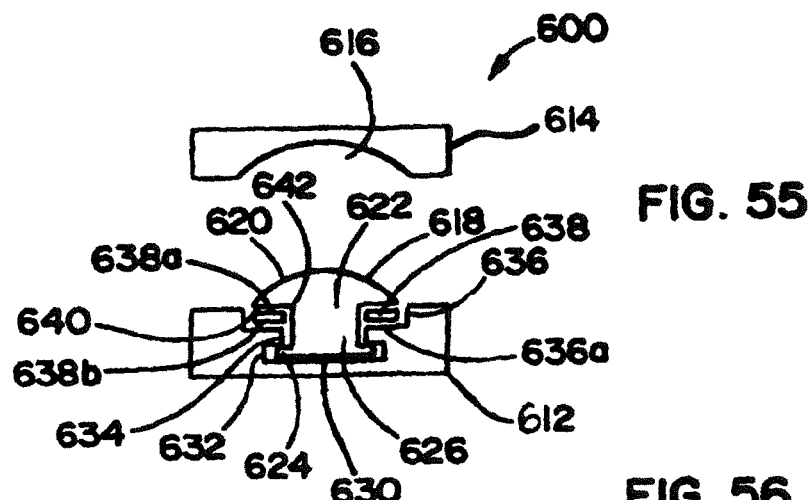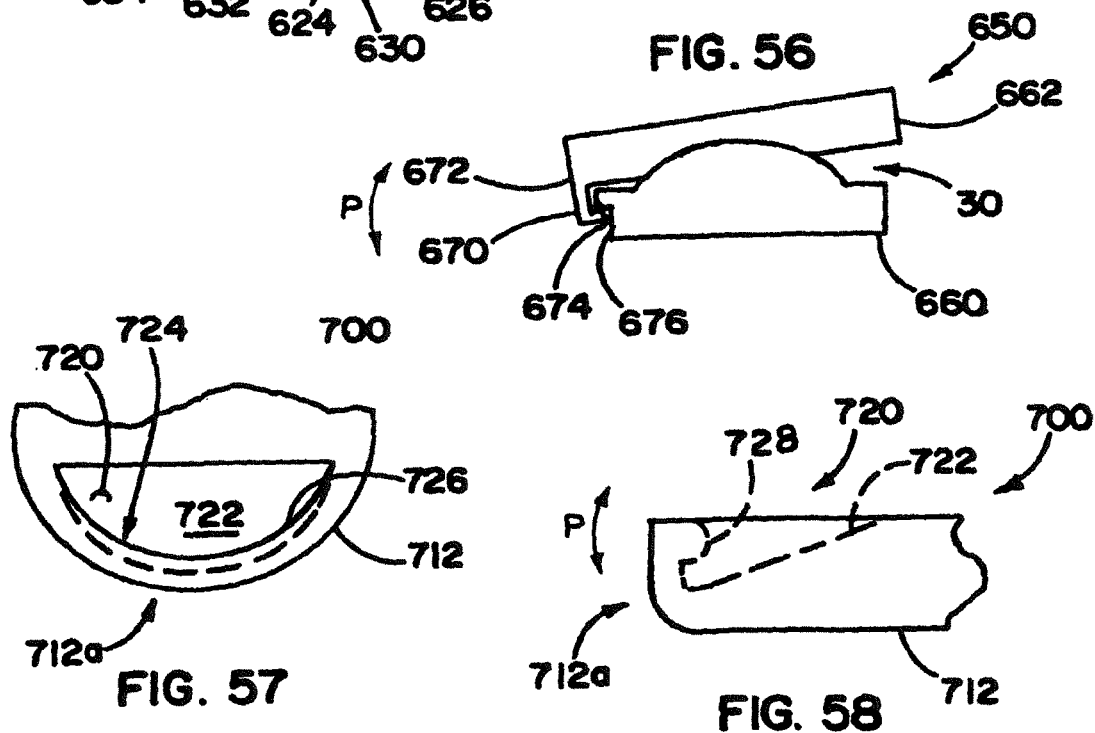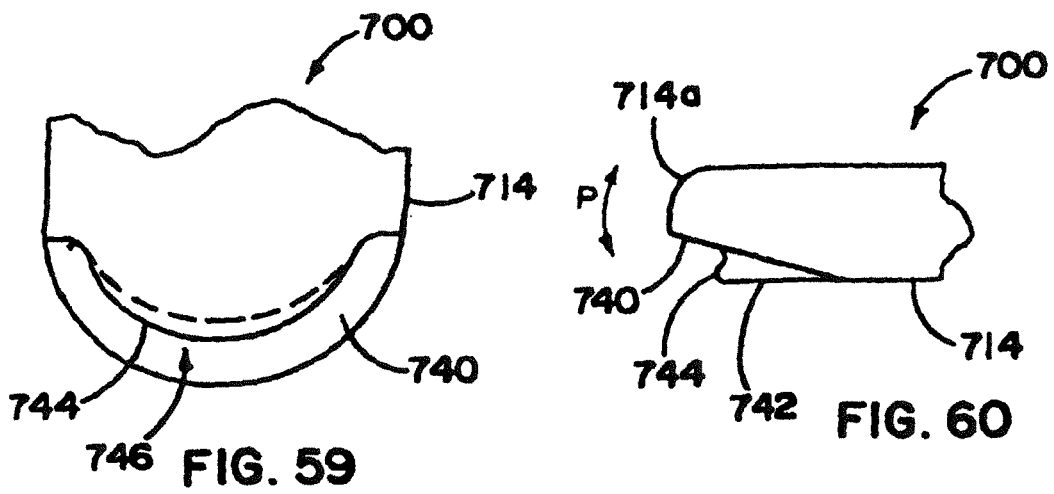

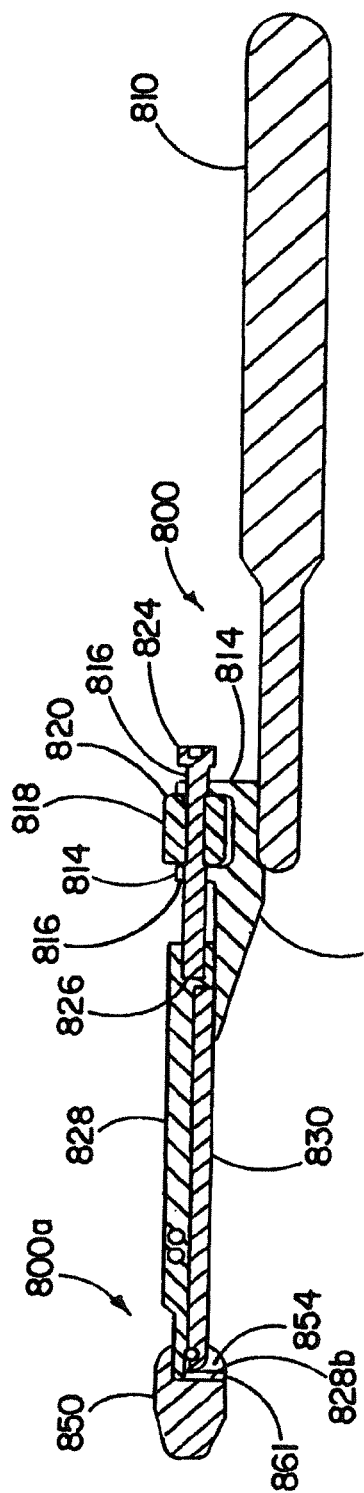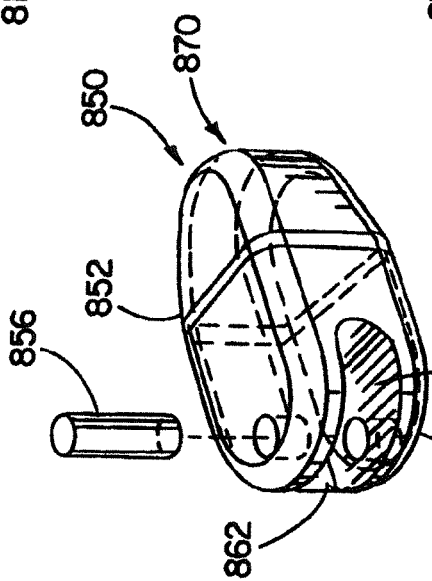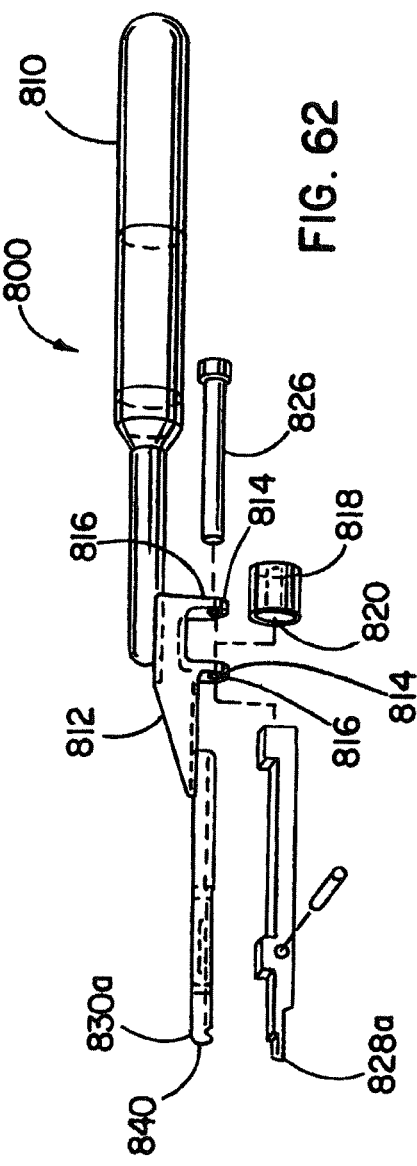

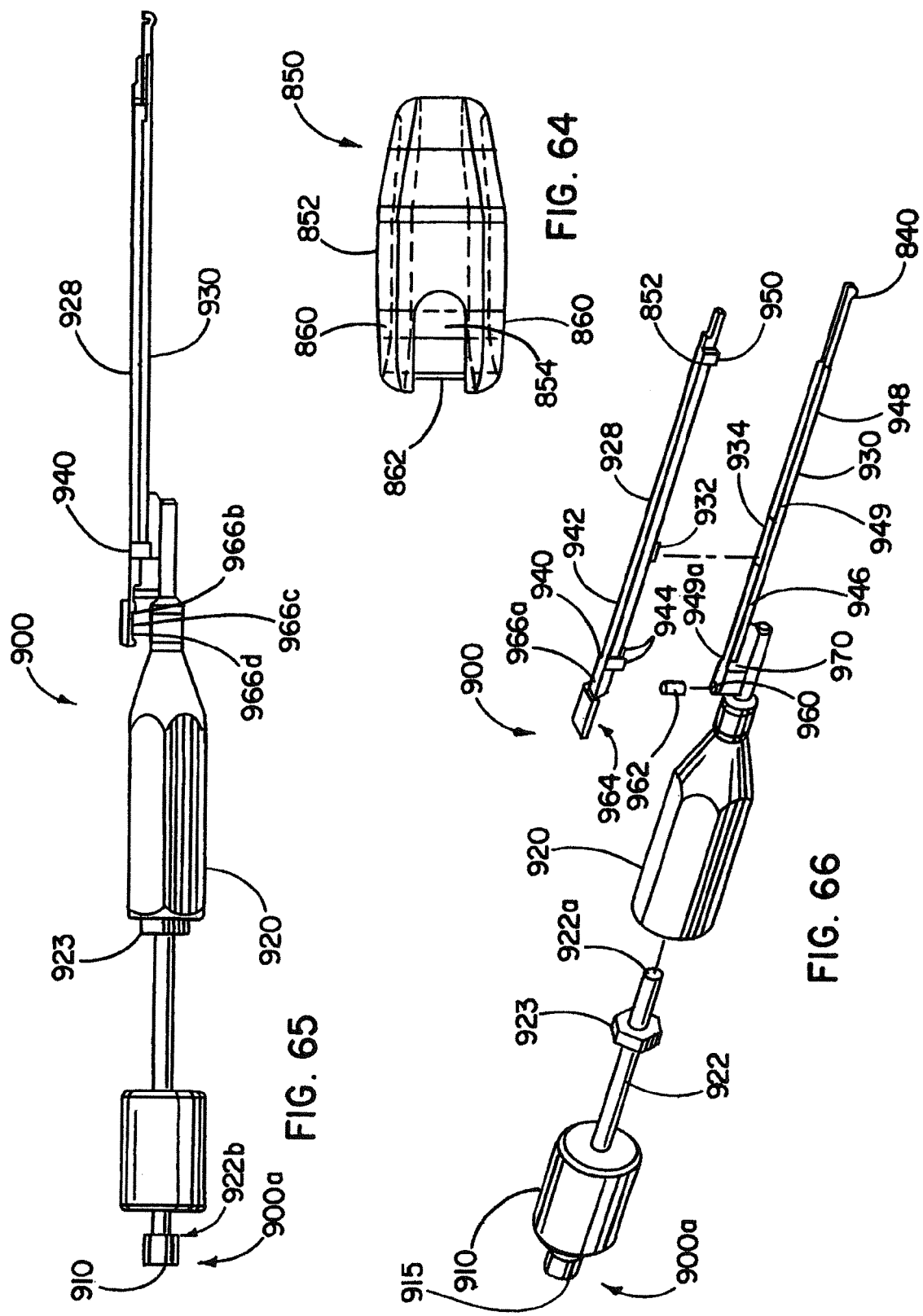

ARTIFICIAL DISC DEVICE

CROSS-REFERENCE TO RELATED APPLICATION

This application is a divisional of U.S. application Ser. No. 10/971,734, filed Oct. 22, 2004, which issued on Aug. 14, 2012 as U.S. Pat. No. 8,241,360, which is a continuation-in-part of U.S. application Ser. No. 10/692,468, filed Oct. 22, 2003, which issued on Mar. 5, 2013 as U.S. Pat. No. 8,388,684, which is a continuation-in-part of U.S. application Ser. No. 10/282,620, filed Oct. 29, 2002, which issued on Feb. 21, 2006 as U.S. Pat. No. 7,001,433, which claims the benefit of U.S. Provisional Application No. 60/382,758, filed May 23, 2002. Each patent application identified above is incorporated herein by reference in its entirety.

FIELD OF THE INVENTION

The invention relates to artificial intervertebral implants and, in particular, to a multiple piece implant that permits relative articulation and/or translation of the multiple pieces.

BACKGROUND OF THE INVENTION

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement may result in, for instance, loss of mobility, urinary and fecal incontinence, and sciatica or pain experienced in the extremities.

Damage to or degeneration of a spinal disc can result from a number of factors such as abuse or age. The disc itself is composed primarily of an annulus and a nucleus contained therein. The annulus is a fibrous annular piece that attaches to the adjacent vertebrae and contains the nucleus, which is in turn a gel-like viscous material capable of shock absorption and flowable to permit poly-axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried and susceptible to damage disc. Because the nuclear material is flowable, extensive damage to the annulus is not necessary for leakage to occur.

Currently, approaches to treatment of spinal problems directly effecting the spinal cord are numerous. For instance, immobilization and high doses of corticosteroids may be employed. The dominant surgical procedures for treatment of these problems are spinal fusion and discectomy. Fusion is a method where adjacent vertebrae are immobilized so that they permanently secure to each other by having bone growth between and to the vertebrae, while discectomy involves removal of a portion or an entirety of a spinal disc.

However, the current practice of each of these procedures typically has certain limitations. With fusion, making a portion of the spine generally rigid produces a reduction in mobility, and drastically alters normal load distribution along the spinal column. Due to these factors, the non-fused portions of the spine experience stress and strain that are significantly increased over normal physiological motions. The increased stress and strain on the non-fused portions may lead to accelerated disc degeneration of the non-fused portions, particularly the adjacent levels of the spine.

Discectomy is effective for relieving sciatic pain by removing the damaged or herniated disc tissue compressing the spinal nerves. However, current discectomy often may lead to a reduction of the disc space between adjacent vertebrae, as well as instability in the affected portion of the spine. Such long-term effects with current discectomy often result in further surgery several years after the initial discectomy surgery.

A recent, though not new, development for spinal surgery of this type is a procedure known as disc arthroplasty for restoring or reconstructing the disc using a prosthesis to replace a portion or entirety of the damaged disc. The primary objective of disc arthroplasty is to restore or maintain the normal disc anatomy and functions, while addressing and treating the causes of the pain. However, little success has been experienced with prosthetic disc implants due to the complexity of the natural disc structure and biomechanical properties of a natural spinal disc. As used herein, the term natural refers to normal tissue including portions of the spine and the disc.

Two types of prostheses for disc arthroplasty are currently believed to merit further development by medical science and research. One type is a total disc prosthesis, or TDP, where the entire spinal disc is replaced after radical discectomy. A typical TDP includes structures that together mimic the properties of a natural disc.

The other type is a disc nucleus prosthesis, or DNP, that is used to replace only the nucleus of a spinal disc after a nucleotomy while retaining the annulus of the disc and, possibly, the end plates intact. As discussed above, failure of the natural disc does not require extensive damage to the annulus, and the annulus would often be capable of retaining a non-flowing prosthetic nucleus. Implantation of an DNP involves clearing of the natural nucleus from the annulus through the procedure known as nucleotomy, and inserting the DNP within the annulus. Accordingly, disc nuclear prostheses (DNPs) are typically smaller and require less extensive surgery than TDPs do.

In using disc implants, there are a number of issues with currently known TDPs and DNPs that attempt to mimic the biomechanical properties of a natural intervertebral disc. Some implants have been designed that provide shock absorption similar to a natural disc. However, these discs have typically been found incapable of maintaining structural integrity over the cyclic load life required of a disc that may be employed for 20 or more years. An early attempt at providing the polyaxial movement and rotation of the spine involved replacing the disc with a metal ball. Undesirably, loading between the ball and the end plates was highly concentrated such that bone subsidence caused the vertebrae to collapse around the ball.

Another issue is implant extrusion, defined as the tendencies for an implant not to remain seated, and for the implant to back out of its intended seat. To prevent this, many designs for disc implants attempt to secure to the end plates of the vertebrae by providing securement features on the implant. The securement features are usually a system of prongs or spikes or other physical protrusions designed to embed in the vertebrae. This, alone, violates the integrity of the end plates to a degree where revision surgery is limited, possibly to spinal fusion for immobilizing the spinal segment and fusing the vertebrae with posterior pedicle instrumentation. Violation of the vertebrae by the securement may cause bleeding, or calcification of the end plate, either of which can result in pain, loss of mobility, necrosis, or deterioration of any implant device. In mating the implant with the end plates, stress concentrations may result due to contour mismatch, such as occur with the above-described implant ball. Thus, positioning of the implant, particularly an implant which utilizes such protrusions, must be performed carefully. To diminish these high stress concentrations or points on the vertebrae, the implant will often have top and bottom plates that cover respective vertebra and often have securement features found on the plates to fix the plates to the vertebrae. In this manner, the stress or forces are distributed thereacross.

Most implants are units that are implanted as a whole. Therefore, the adjacent vertebrae must be sufficiently distracted for the effective size of the implant including the top and bottom plates, which can be significantly increased when fastening protrusions are included. This requires greater invasiveness, which complicates surgery and leads to greater time for recovery and post-surgical pain. Furthermore, this often destroys any remaining utility for the annulus as a large incision must be made, in the event it is even retained. As the annulus does not heal well and suturing the annulus is difficult due to its tissue properties, the ability of the annulus to retain the implant is diminished if not eliminated, and implant extrusion often is not prevented by the annulus.

Some implants that are inserted as a whole utilize a bladder or balloon-like structure. These implants may be inserted in a collapsed state, and then inflated once in situ. However, these implants typically rely on a structure that is entirely resiliently deformable. Therefore, these implants typically are limited to providing shock absorption, while not providing range of motion with high-cyclic loading or sufficient support.

Most spinal disc procedures require an anterio-lateral approach to the surgical site. More specifically, spinal disc implants typically have a size roughly that of the natural spinal disc. In order to evacuate the disc space and implant the prosthetic device, space is required. Because of the geometry and structure of a vertebra, a natural disc, and an artificial disc implant, posterior surgical procedures do not typically permit the access required for evacuation of the disc space and implantation of the prosthetic device. Furthermore, for an anterior-lateral approach to the surgical site, a general surgeon's service must be employed, typically in conjunction with an orthopedic surgeon or neurosurgeon, or both. Therefore, an implant device that may be implanted in multiple surgical approaches is desirable.

Less extensive surgery is required for a DNP than for a TDP. A DNP replaces only part of the disc. Implantation of most DNPs with pre-formed dimensions requires a 5-6 mm, or larger, incision in the annulus for implantation. Some DNPs, such as those utilizing in situ curable polymers, may be performed percutaneously. In any event, implantation of a DNP requires minimal disc tissue resection, and can avoid violating the end plates of the vertebrae for securing. Moreover, recovery and post-surgical pain are minimal due to the minimal invasiveness of the procedure, and interbody fusion remains a viable revision surgery, It has been found herein that it is particularly important to restore the normal range of motion of the spine. Specifically, it has been found to be more important to provide flexion/extension, lateral bending, and axial rotation of the spine, than it is to provide the compressive modulus of elasticity. More particularly, it is believed that failure to provide the normal range of motion has the deleterious effects, as discussed above, of spinal fusion. In contrast, it is believed that the loss of compressive elasticity in that region may be borne by the other natural spinal discs. As the implant needs to restore or maintain disc height, it should withstand a significant amount of compressive load in the proper physiological manner so end plate damage is not induced that may lead to pain and implant subsidence.

A number of attempts have been made at artificial discs, each presenting deficiencies. Some procedures and devices rely on lateral or anterior surgical procedures, which are highly invasive and traumatic and which carry high surgical risk.

Accordingly, there has been a need for an improved disc implant for mimicking the biomechanical properties of a natural disc.

SUMMARY OF THE INVENTION

In accordance with one aspect of the present invention, a multi-piece nucleus implant device is disclosed for replacing a nucleus removed by a nucleotomy. The implant may include at least a first shell or plate member, a second shell or plate member, and a bearing member providing at least one direction of movement between the two shells, and preferably being a polyaxial articulating bearing member. The articulating bearing member provides for the natural movement of the spine including flexion/extension, lateral bending, and rotation. Each of the plate members and the articulating bearing member are generally formed to be rigid. Therefore, the implant is capable of supporting the compressive and cyclic loads required of a natural disc.

In some forms, the implant may also provide for relative sliding and/or translation between the shells and the articulating bearing member. Specifically, the surfaces between the shells and the articulating bearing member are able to slide relative to each other. As the mechanics of a natural disc are those of a viscous fluid, the bend of the spine in one direction forces the fluid in an opposite direction. The shells of the implant rotate relatively in a particular manner due to bending forces on the implant. However, due to the dimension requirements of the implant, the shells need not rotate around a fixed pivot point. To mimic the behavior of the natural nucleus in this manner, and to do so with rigid members, the articulating bearing member permits the components of the implant to shift relative to each other. Furthermore, some forms of the implant allow a center insert or spacer member that may shift away or by sliding and/or translating from the direction of bending to more closely mimic the behavior of a natural disc, as will be discussed below.

One aspect of the present invention is providing a polyaxial articulating device utilizing a concave recess and a dome member formed between the shells. The dome member and recess form an articulating bearing member permitting polyaxial movement of the shells relative to each other, and the dome surface and recess may slide or translate relative to each other.

In some forms, the stiffness of the polyaxial rotation of the articulating bearing member may be controlled and varied. The respective radii of curvature for, and hence the fit between, the recess and dome surface may be varied to produce a different stiffness. In general, if the radius of curvature of the recess is greater than that of the dome surface, there is a less restricted condition, and the stiffness is lowered. Conversely, if the radius of curvature of the recess is lower than that of the dome surface, there is a more restricted condition, and the stiffness is increased.

As another aspect of the present invention, the outer surfaces of the implant that contact the end plates of adjacent vertebrae may be provided with a convexity selected according to the natural, overall concavity of the end plate. When the convexity of the outer surfaces of the implant match the concavity of the end plate, forces will be generally evenly distributed across the end plate and high stress points are avoided. The construction of the implant, then, avoids bone subsidence issues and the integrity of the end plates is maintained. If revision surgery is necessary, this permits the surgery to employ a range of desired methods.

Alternatively, the convexity of the outer surfaces of the implant may be slightly decreased. The bone of the end plate is slightly elastically deformable. A slight mismatch between the outer surfaces and the end plate allows residual stresses to develop between the outer periphery of the outer surface shell and the end plate, stresses which serve to hold the generally convex outer surface of the implant in proper position. Any such alteration should be restricted to the degree that bone subsidence does not occur.

In another aspect of the present invention, the implant has a generally oval or racetrack shape. A natural disc and nucleus are kidney-shaped, having a smaller dimension in the anterior-posterior direction than in the lateral direction. Therefore, the space provided by the removal of the nucleus has a similar shape. Though the kidney-shape may or may not be replicated, implant performance has been found herein to benefit from having a wider lateral dimension than anterior-posterior dimension, such as a generally oval, racetrack, or trapezoidal shape, for the shells. To further reduce the size of the incision made in the annulus, which improves the ability of the annulus to prevent implant extrusion, the shells of the implant may be inserted with a lateral end leading first through a posterior incision in the annulus. In this manner, the shells may then be pivotally rotated within the nuclear space.

To facilitate the rotation of the shells within the nuclear space, an embodiment of the invention includes a post for gripping, inserting, and rotating one or more of the shells. The post may have a flat portion and a round portion so that a tool may grip the post in a first position such that the post may not rotate relative to the tool during insertion. Once inserted, the tool may partially release the post so that the tool no longer abuts the flat, and the post may rotate relative to the tool without being fully released. The tool may then direct the rotation of the shell within the nuclear space.

It has been found that distraction of the annulus helps alleviate pain and improves stability of the intervertebral joint. As discussed above, the shells of the implant do not necessarily replicate the shape of the natural nucleus. In the event the shape of the implant may not match that of the natural nucleus, the outer periphery of the implant may engage and stretch portions of the annulus, thereby providing tension to those portions of the annulus. In addition, an outer curtain or sheath in the form of, for instance, a pleated bellows may be provided spanning between and generally sealing the compartment between the shells. The bellows may then be injected with a material, such as gas or liquid, such that the bellows or curtain distends to apply pressure on the interior of the annulus. Additionally, the injected material may expand slightly in situ the nucleus implant. As a further benefit, the bellows prevents foreign material from entering the implant device which otherwise may hinder or deteriorate the performance of the implant, particularly the articulating bearing member.

In a further aspect of the present invention, it is desirable to restrict the anterior-posterior bending of the implant. Generally, the greatest deflection between vertebrae is approximately 15°. Due to the polyaxial nature of the movement provided by the implants of the present invention, the lateral direction provides approximately 15°, and the anterior-posterior directions may permit greater motion. In some embodiments, then, it is desirable to mechanically prevent deflection beyond 15°. In one form, the shells include a short wall extending towards the opposing shells that physically abut when the 15° bend is reached. In another form, a spacer member may be an annular ring extending from its periphery and between the shells such that the shells contact the ring when the 15° angle is reached. In another form, the shells may be provided secured together by a cable that connects the shells to prevents the shells from bending beyond 15° and to prevent the spacer member from escaping from between the shells.

In some embodiments, each shell may provide for rotational, sliding, or translational movement, and an insert or spacer member may be located between the two shells and may have two surfaces moving against the respective shells. It is believed multiple wear surfaces interfacing increases the life expectancy of the implant with respect to wear. In some forms, each shell may have a concave recess, and the spacer has two dome surface portions, each facing a respective shell, and forms an articulating bearing member with each concave recess. In other forms, the spacer member may have a dome surface on one side meeting a concave recess in a shell thereby providing for polyaxial rotation, translation, and sliding, and may have a flat on another side engaging a flat surface in a recess in a shell thereby providing for linear translation and planar rotation.

In some forms of the multi-piece implant, a multi-piece implant is disclosed where the pieces may be sequentially inserted through an incision in the annulus for assembly within the disc nucleus space. As such, the incision need not provide space for the entire implant to be inserted, and the invasiveness of the procedure is minimized, which in turn diminishes post-surgical recovery and pain. In addition, any distraction of the adjacent vertebrae that need occur is minimized by inserting the implant in portions. As the incision does not allow the entire implant to be inserted, the remaining integrity of the annulus may be utilized. Specifically, the annulus may be used to retain the implant in place within the annulus and in the nucleus space. Therefore, protrusions for securing the implant to end plates of adjacent vertebrae are unnecessary to prevent the implant from escaping from between the vertebrae.

In a similar form of the multi-piece implant, each shell may include a concave recess and a double-domed spacer member. By providing a dome surface for each of the recesses, the wear upon the surfaces therebetween is reduced, as described. The pieces are sequentially inserted in any order through the incision of the annulus, though it is preferred that the shells are inserted first to prevent injury to the end plates. The shells may include aligned ramps, or a similar structures, to the side of their respective concave recesses to allow the spacer member to be inserted therebetween. In addition, the members may be inserted, and then one or more may be rotated or translated so that the spacer member is prevented from backing out through the incision in the annulus and/or to further expand the implant. This embodiment then provides for polyaxial movement and allows the shells each to slide and/or translate relative to the spacer member, and the spacer member may slide or translate away from the direction of bending. It should be noted that the maximum clearance provided by the incision in the annulus need be that required by the largest of the three pieces.

A further form of the multi-piece implant includes a shell with a concave recess, as described above, a shell with steps or ramps rising towards its center, and a spacer member having one side stepped or ramped and the other side domed. Here, the shells may be inserted through the incision in the annulus so that the stepped portion of the shell is facing the incision. The spacer member may be then forced between the shells such that the stepped spacer member cams up the steps of the stepped shell until the dome surface is received in the concave recess of the other shell. The stepped portion of the shell may include sidewalls to direct generally the path of the stepped spacer member. The sidewalls may be positioned so that the spacer member may slide or translate a short distance along the steps, while also preventing overtranslation. Preferably, the steps of the shell extend from a lateral side of the shell. In one form, the stepped shell is rotated after expansion, while in another the stepped shell may be rotated and then the implant is expanded.

In a further aspect of the invention, a multi-piece implant device is disclosed where the entire implant is inserted through an incision in the annulus. The implant is inserted in a compressed or collapsed state as a unit and then expanded after implantation. The size of the incision in the annulus need only provide for the size of the unexpanded implant. As discussed, the implant may be inserted with an end having a shorter, lateral dimension leading first and then may be rotated once the trailing portion of the implant is inserted in the incision. Alternatively, rotation can begin before the implant is entirely inserted through the incision so that rotation occurs as the implant is being pushed through the incision. Accordingly, the incision need only provide for insertion of the compressed implant, the invasiveness of the procedure is minimized, the post-surgical recovery and pain are minimized, distraction of the adjacent vertebrae is minimized, the annulus will assist in retaining the implant in place, and protrusions for securing the implant are unnecessary.

In an embodiment of this aspect, an implant with a helically stepped spacer member that may be inserted in a collapsed state and then expanded is provided. The stepped spacer member allows the implant to be expanded step by step to the desired vertical height. At least one shell has a concave recess into which a dome surface of a spacer member is received. The spacer member has two opposing parts, one of which may be integral with a second shell or may have a dome surface received into a concave recess in the second shell. The opposing spacer member parts have helically oriented steps, and the spacer member and/or implant may be inserted or assembled within the nucleus space in a compressed or collapsed state or arrangement. Once implanted, the opposing parts of the spacer member may be rotated relative to each other such that the steps ratchet up, thereby expanding the spacer member to an expanded arrangement. Each dome surface and recess provide for polyaxial movement of the implant, translation, and arcuate sliding, as described above.

In a further embodiment, a spacer member may be provided with a member rotating around a longitudinal axis and connected to one or more non-rotating wedges. The rotating member is turned to pull or push any wedges from a first, compressed position to a second, expanded arrangement. The wedges are forced between two portions of the spacer member to expand the spacer member and, therefore, to expand the implant. At least a portion of the spacer member has a dome surface that is received in a concave recess of a shell.

In another embodiment, the spacer member may include cam surfaces which cam against mating cam surfaces of another portion of the spacer member or of one of the shells. The cam surfaces may rotate relative to each other, thus camming the portions to expand, thereby expanding the implant. Again, at least a portion of the spacer member has a dome surface that is received in a concave recess of a shell.

In an additional aspect of the present invention, the spacer member may form an internal cavity or canister. In one embodiment, the cavity may be formed by the spacer member and a portion integral with one shell such that the spacer member and shell expand relative to each other, thereby expanding the implant. In another embodiment, the cavity may be formed by two portions of the spacer member that expand relative to each other, thereby expanding the implant. In a further embodiment, the cavity may be formed by two end pieces and a cylindrical wall of the spacer member such that the end pieces expand along the cylindrical wall to expand the implant. In any of these embodiments, the spacer member may include an internal balloon for receiving an injected material so that the injected material is captured within the cavity. Alternatively, injected material may be forced into the cavity such that the portions of the cavity are sealed. Curable material may be used such that the expanded spacer member is rigid. Alternatively, the spacer member may be filled with an elastomeric or flowable material that provides some shock absorption.

Various forms of the present invention may be implanted in an anterior, anterior-lateral, or a posterior surgical procedure. The size of each implant component or a collapsed implant may be such that each may be inserted with only a small incision in the annulus. Furthermore, the spinal structure permits the components or collapsed implant to be inserted through the posterior of the spine. A posterior approach to the surgical site reduces the invasiveness of the procedure, and may often be performed by a single orthopedic surgeon or neurosurgeon without a need for a general surgeon, and thus substantially decreases the cost and complexity of the procedure.

To direct the implantation and the rotation of an implant, an embodiment of the invention includes structures located on multiple portions of the implant for being gripped and manipulated by an inserter tool. The implant structure may include a recess and/or a post for being gripped by the inserter tool. The inserter tool may grip the implant in a predetermined insertion orientation such that rotation of the implant relative to the inserter tool is generally avoided. The grip of the inserter tool may be adjusted during the implantation procedure such that the implant may be rotated by the inserter tool within the nuclear space to an implanted position. The procedure may include inserting the implant with a minor dimension oriented to pass through the incision in the annulus, and the implanted position may include orienting a major dimension to extend at least partially along the incision in the annulus, such as at an oblique angle, to minimize likelihood of the implant backing out through the smaller incision. Thus, it would be difficult for the implant to shift out of the annulus on its own because, in this orientation, backout by the implant would require a turning force to align the minor dimension with the incision. That is, without a turning action, the major dimension of the implant is intended to be too large to fit through the incision. Once implanted, the inserter tool may release from the implant for extraction of the inserter tool.

In a further embodiment, the implant may be provided with structure to secure implant pieces in a particular orientation for implantation as a unit. The implant may be configured as a wedge to provide an insertion configuration to ease insertion of the implant into and through the annulus. For example, a first implant piece may be provided with a recess and a second implant piece may be provided with a projection received within the recess such that the recess and projection are releasably connected with each other. When connected as such, the implant has an insertion configuration, and the insertion configuration may include having an insertion or leading end smaller than a trailing end. In this regard, the first and second implant pieces are positioned as to form a wedge shape or angle for facilitating insertion into and through the annulus, as well as between the vertebrae and within the nuclear space.

The connection providing the insertion configuration may be released once implanted, and the constraint of the annulus and/or vertebrae, combined with the force of insertion, may act upon the first and second implant pieces in a fulcrum-like manner to pivot the implant pieces, thereby releasing the connection. Accordingly, the orientation providing the wedge shape for insertion may be a releasable connection which may include an interference fit between the connecting structures. The interference fit may be formed on a leading end and cooperate in the direction that the pivoting ends of the implant member shift when shifting toward and away from each other between the insertion and operable configurations.

The releasable connection may be a snap-fit connection having a projection received within a recess to hold the members in a pre-determined general relative orientation during insertion, and until the force of insertion against the implant members by the vertebrae forces the projection and recess to release. Thus, the implant may be shifted from the insertion configuration to an operable configuration, particularly by release of the snap-fit connection.

In a form, the releasable connection may be such as a dove-tail joint such that the projection is a dove-tail that is received within the recess having a complementary geometry. The dove-tail joint may be formed by snapping the dove-tail projection into the recess, to form a snap-fit, and also be provided by sliding the dove-tail projection into the recess through an opening at one end thereof such that the dove-tail projection has an interference fit with the recess and is released by snapping out thereof.

In another form, the first and second implant members may be provided with structure at the leading end that forms a catch such that the vertebrae contacting outer surfaces of the implant members act in fulcrum-like manner to release the catch to shift the implant members from the insertion configuration to the operable configuration. The catch may be formed by a projection from the first implant member that is received in a hook or barb on the second implant member.

In another form, the projection may be a tongue received in an opening angled from the plane of the members and generally so the tongue and opening form a butt-joint. Upon a threshold of force from insertion, the tongue slips and releases from the opening to shift the implant members from the insertion configuration to the operable configuration.

As a plurality of size and shapes of implants may be provided, it is advantageous to make an examination of the implantation site, the nuclear cavity, in order to make a proper selection of implant geometry and dimension. In promotion of this, a plurality of trial spacers may be provided for removable insertion such that one or more trial spacers may be sequentially inserted and removed until a proper fit is determined. The trial spacers may be shaped to parallel the shape of the implant in the operable configuration, and may be shaped to facilitate insertion into and through the annulus.

To insert and remove the trial spacers used to assess the nuclear cavity, a trial spacer instrument may be provided. The trial spacer instrument may secure the trial spacer thereto so that the trial spacer is generally in a fixed orientation during insertion, while also adjusting the securement to the trial spacer so that the trial spacer may be rotated within the nuclear cavity in like manner to the implant. The trial spacer instrument may be adjustable and may be provided with a securable member, such as a screw-like member, for adjusting the securement of the trial spacer thereto, and a knob for securing that position. Alternatively, the trial spacer instrument may include a plurality of predetermined positions for the securement of the trial spacer.

BRIEF DESCRIPTION OF THE DRAWINGS

In the drawings,

FIG. 10 is a top plan view of a shell and an insertion implement in a locked position;

FIG. 11 is a top plan view of the shell and the insertion implement of FIG. 10 in an intermediate position;

FIG. 12 is a top plan view of the shell and the insertion implement of FIG. 10 in an unlocked position;

FIG. 55 is a cross-sectional view of an alternative artificial disc device showing a dome member that is distinct from the upper and lower members;

FIG. 56 is a cross-sectional view of an alternative artificial disc device having an alternate connection between the upper and lower members;

FIGS. 57-60 are plan and elevational views showing alternate structure of the respective ends of the lower member (FIGS. 57 and 58) and upper member (FIGS. 59 and 60) for forming a releasable connection therebetween;

FIG. 61 is a side cross-sectional view of a trial spacer instrument holding a trial spacer at a distal end thereof in accordance with the present invention;

FIG. 62 is an exploded, perspective view of the trial spacer instrument of FIG. 61;

FIG. 63 is a perspective view of the trial spacer of FIG. 61;

FIG. 64 is a side elevational view of the trial spacer of FIG. 63;

FIG. 65 is a side elevational view of an alternative trial spacer instrument having an alternative adjustment mechanism;

FIG. 66 is an exploded perspective view of the trial spacer instrument of FIG. 64;

DETAILED DESCRIPTION OF THE PREFERRED EMBODIMENTS

Figure 1:
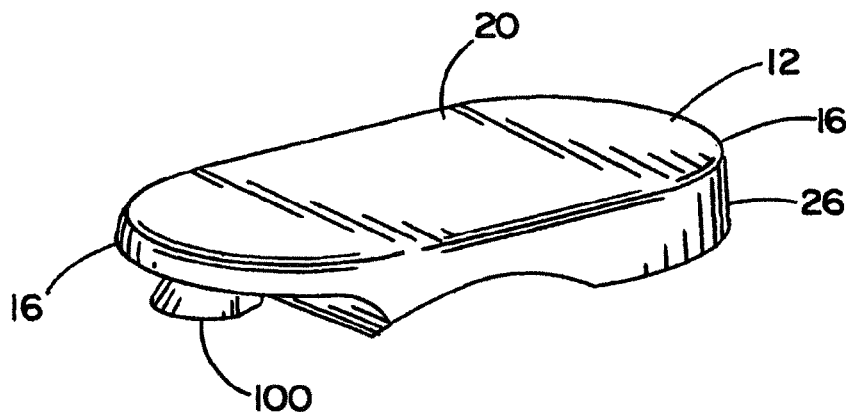
FIG. 1 is a first perspective view of a shell of an implant of an embodiment of the present invention.
Figure 2:
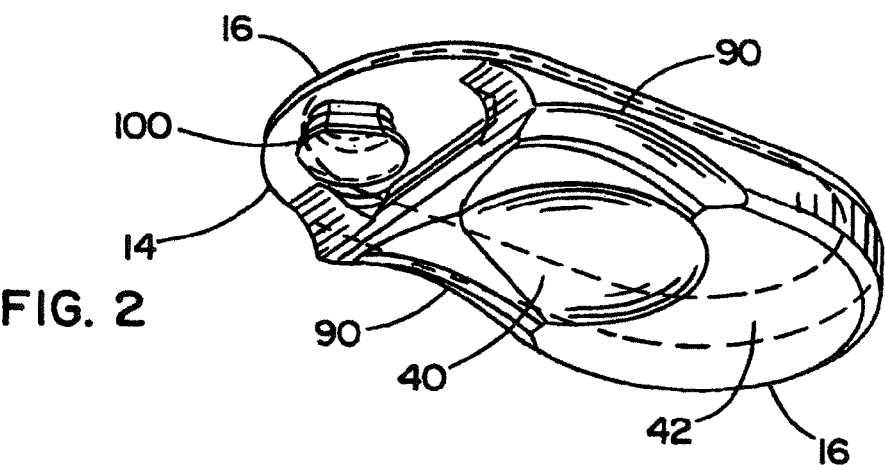
FIG. 2 is a second perspective view of the shell of FIG. 1.
Figure 3:
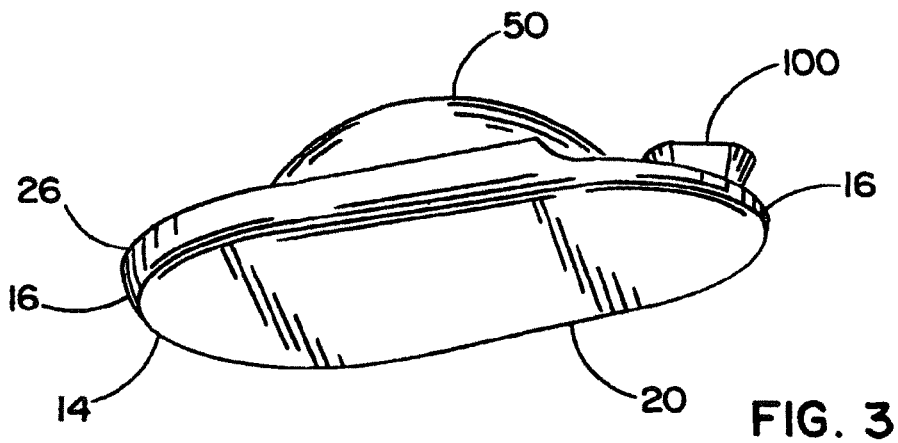
FIG. 3 is a first perspective view of a shell including a dome surface.
Figure 4:
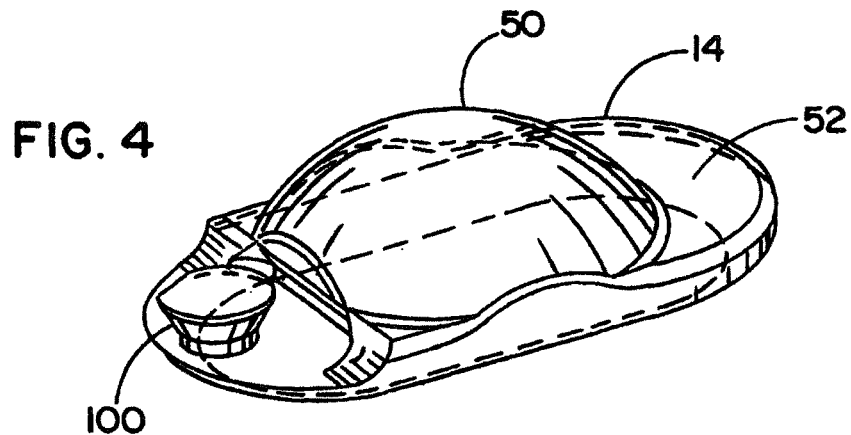
FIG. 4 is a second perspective view of the shell of FIG. 3.
Figure 5:
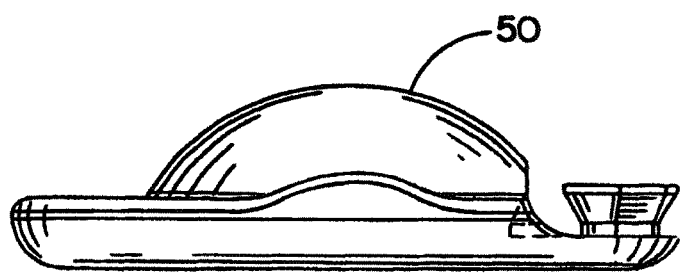
FIG. 5 is a side elevational view of the shell of FIG. 3.

Referring now to the FIGURES, one embodiment of an implant device 10 is depicted including a top shell 12 and a bottom shell 14. As used herein, the terms top shell and bottom shell are simply referential for the arrangement of the shells as depicted, and the arrangement could be reversed. The implant 10 is a prosthetic nucleus implant for replacing the nucleus of a damaged natural spinal disc. The nucleus of the natural spinal disc is generally cleared by a procedure known as a nucleotomoy where an incision is made in an annulus surrounding the nucleus, whereupon the nucleus is substantially removed. Typically, a small amount of the viscous nuclear material remains in the disc space, and this material can be used to provide an interface for reducing possible stress points due to incongruities between the implant 10 and end plates of the adjacent vertebrae.

One embodiment of the implant 10 is inserted through the incision in the annulus such that the annulus remains attached to adjacent vertebra and holds the implant 10 in an intervertebral position in the nucleus space. In order to utilize the annulus in this manner, the implant 10 may be inserted either in components or pieces, or may be inserted in a compressed or unexpanded state or arrangement. Once in situ or implanted, the implant 10 may be assembled, expanded, or both, as will be described below. Accordingly, the incision in the annulus is smaller than a typical nuclear implant requires, and the surgery is minimally invasive. Because the size or arrangement of the implant 10 is altered after being inserted through the annulus, the expanded or assembled implant 10 cannot escape from the annulus. By using the annulus to prevent implant extrusion or escape, protrusions or other securements that penetrate, abrade, or otherwise disturbe the integrity of the surface of the end plates are eliminated. By retaining the annulus, the vertebral sections have greater stability and may more closely return to normal motion, as well as the site minimizes scarring from removing or otherwise excessively damaging the annulus.

Each shell 12, 14 has an outer surface 20 for engaging and mating with an adjacent vertebra (not shown), specifically with an end plate of a vertebra. The outer surface 20 of each shell 12, 14 is preferably smooth to avoid disturbing the surface of the end plates. The end plates of the adjacent vertebrae have naturally occurring concave surfaces mating with the outer surfaces 20 of the shells 12, 14. The vertebra above the implant 10 has a slightly different concavity from that of the vertebra below the implant 10. Preferably, the outer surface 20 of each shell 12, 14 is contoured with a convexity 18 (see, e.g., FIGS. 26, 33, 34) corresponding to the concavity of its respective adjacent vertebra. In one embodiment, the radius of curvature of the convexity 18 of the outer surface 20 of each shell 12, 14 matches the radius of curvature of the concavity of the adjacent vertebra. In another embodiment, the radius of curvature of the convexity 18 of the outer surface 20 of each shell 12, 14 is slightly less than the radius of curvature of the concavity of the adjacent vertebra. As the bone of the end plate is slightly elastically deformable, the slight mismatch of the interface between the outer surface 20 of the shell 12, 14 and the respective vertebrae impart a slight residual stress that serves to impede movement of the shells 12, 14 relative to the vertebrae. As a further alternative, the radius of curvature of the convexity 18 of the outer surface 20 of each shell 12, 14 may be slightly greater than the radius of curvature of the concavity of the adjacent vertebra. Again, as the bone is slightly elastically deformable, the slight over-convexity of the outer surfaces helps insure a more even distribution of compressive force on the implant and adjacent vertebra. Any such mismatch should not be such that bone subsidence, as described above, occurs.

Preferably, each shell 12, 14 has a peripheral shape 26 of an oval or a racetrack shape to have a greater lateral dimension D1 than longitudinal or anterior-posterior dimension D2. Alternatively, each shell 12, 14 may have a trapezoidal, round, or kidney shape (see, e.g., FIGS. 31-32). In addition, the peripheral shape 26 may be rounded or radiused. In order to most evenly distribute the compressive forces experienced by the implant 10 across the end plate, the size and shape 26 of the shells 12, 14 preferably cover as much of the end plate in the nuclear space as possible. In addition, the periphery 26 of the shells 12, 14 preferably contacts and places in tension at least a portion of the inner surface of the annulus in which they are implanted, as will be discussed below.

Figure 7:
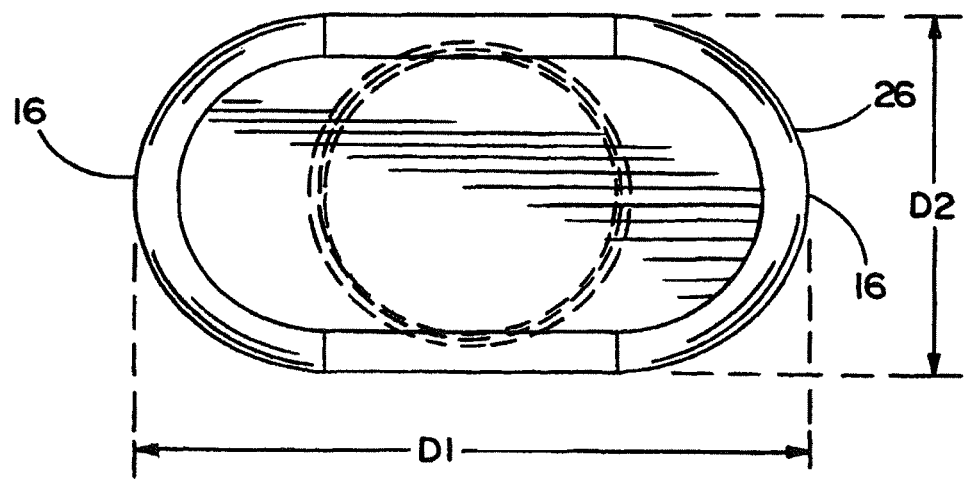
FIG. 7 is a top plan view of an implant with a spacer member in phantom
Figure 6:
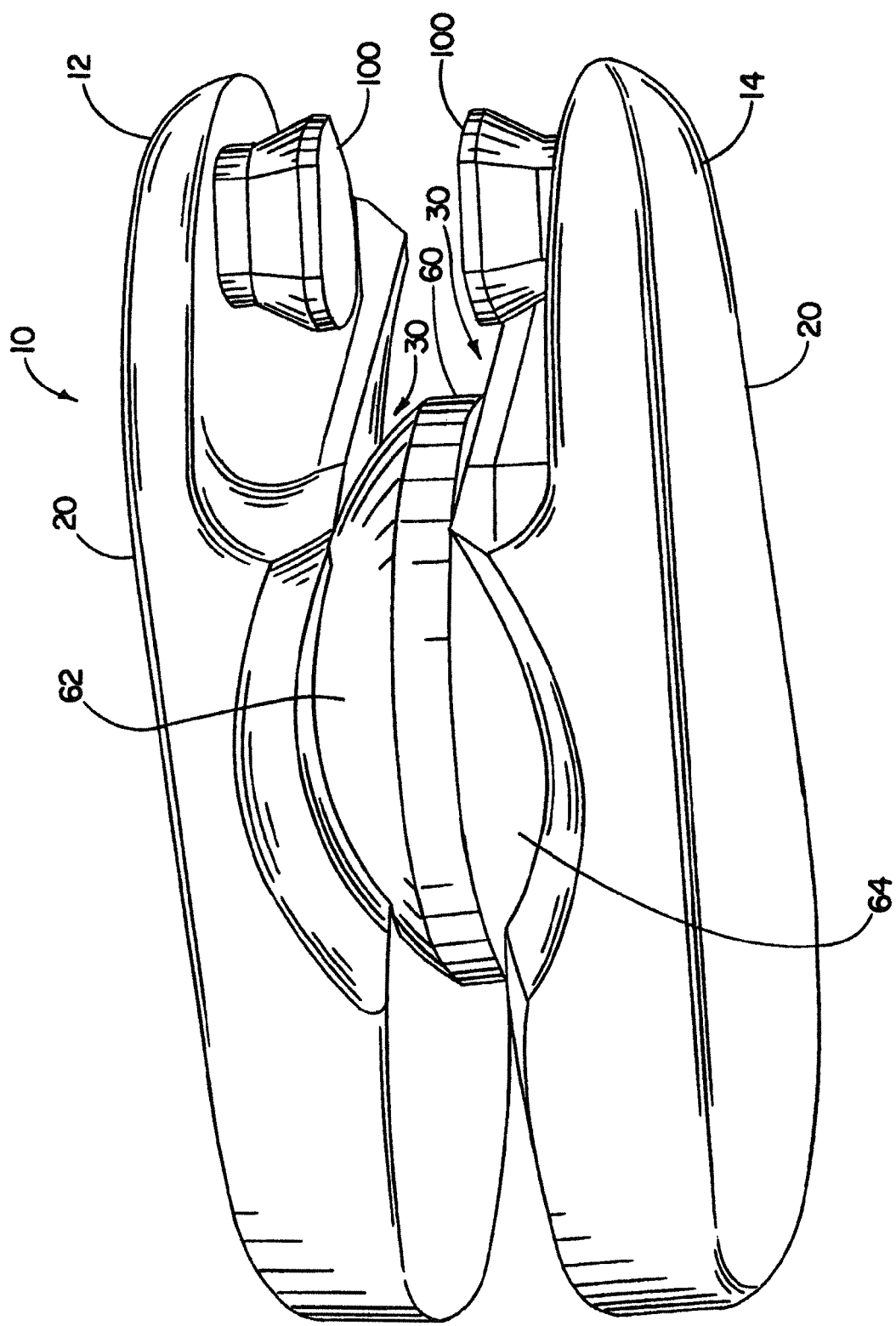
FIG. 6 is a perspective view of an implant of an embodiment of the present invention.
Figure 8:
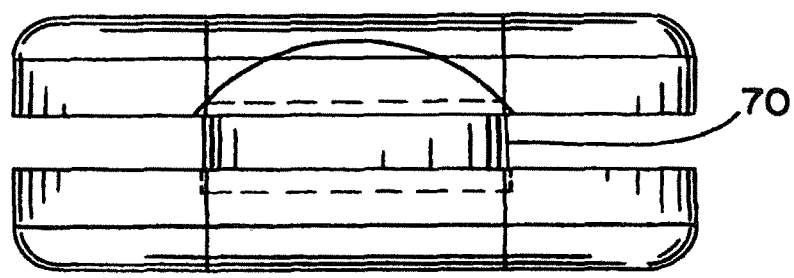
FIG. 8 is a side elevational view of the implant of FIG. 7.
Figure 9:
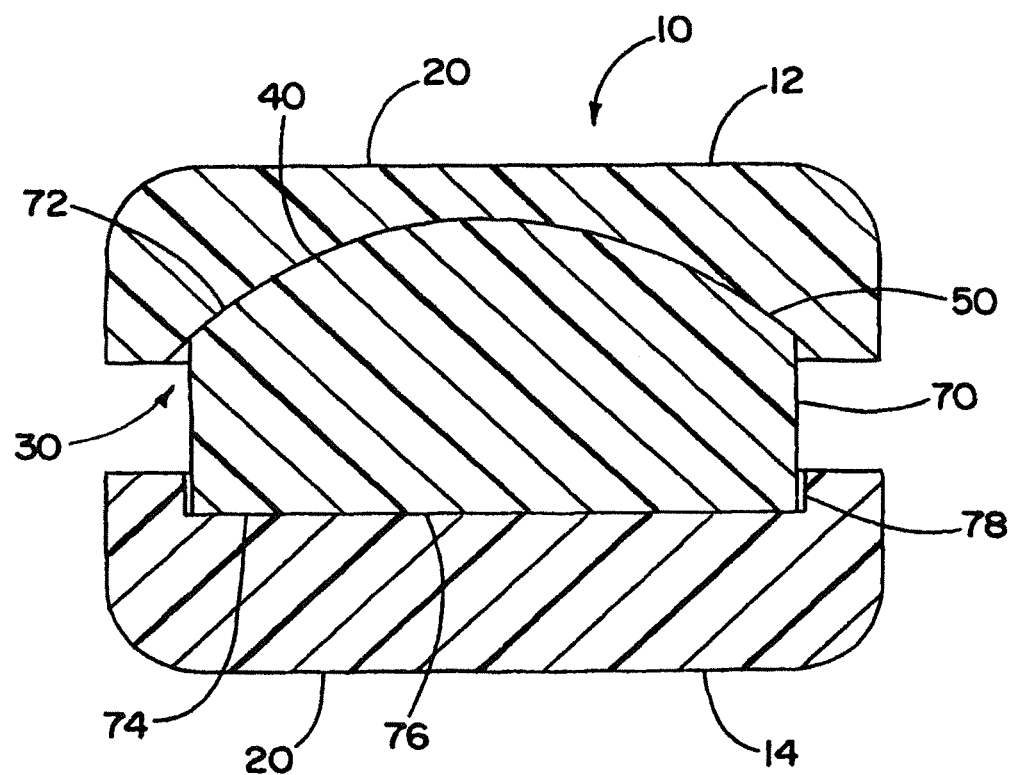
FIG. 9 is a cross-sectional view of the implant of FIG. 7.
Figure 13:
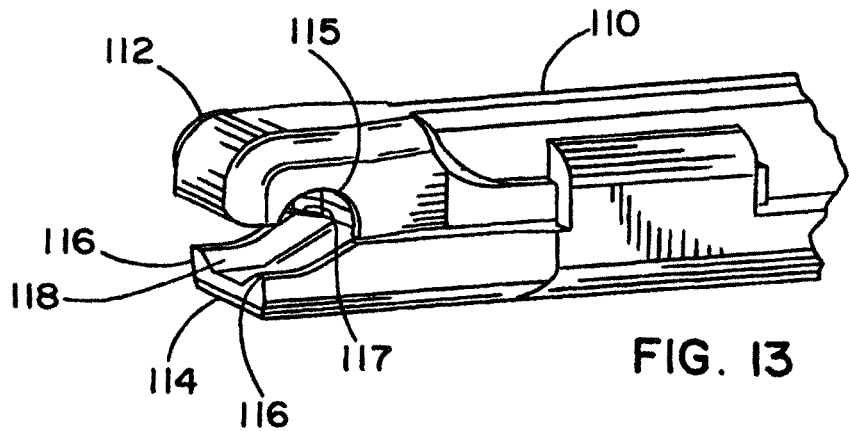
FIG. 13 is a perspective view of the insertion implement of FIG. 10.

Each implant 10 is provided with at least one polyaxial articulating bearing member 30 formed between a concave recess 40 formed in the top shell 12 and a dome surface 50. The dome surface 50 and the surface of recess 40 mating with the dome surface 50, as well as another sliding surfaces as described herein, are preferably smooth for low friction engagement. As depicted in FIGS. 1-5, the recess 40 is formed in a face 42 (FIG. 2) that opposes the bottom shell 14, and the dome surface 50 is formed on a face 52 (FIG. 4) of the bottom shell 14 that opposes the top shell 12. Alternatively, as depicted in FIG. 6, an implant 10 may be provided with a pair of polyaxial articulating bearing members 30, where a spacer member or insert 60 is provided with opposite faces 62, 64 each including a dome surface 50 for being received in a concave recess 40 in each of the confronting shells 12, 14. As a further alternative, FIGS. 7-9 depict a spacer member 70 having opposite faces 72, 74, where the face 72 includes a dome surface 50 and the face 74 includes a flat 76. For the spacer member 70, the dome surface 50 is received in a recess 40, and the flat 76 is received in a similarly shaped, though slightly larger, recess 78 with a flat surface in the bottom shell 14 such that the flat 76 may slide or translate in the recess 78. Two wear surfaces reduce the overall wear experienced in comparison to a single wear surface, and as such two such surfaces are preferred. It should be noted that the radius of curvature of opposing sides of a spacer 60 providing two wear surfaces need not be identical.

Each articulating bearing member 30 between a dome surface 50 and a recess 40 provides polyaxial motion of the concave recess 40 relative to the dome surface 50. Particularly, the bearing member 30 permits flexion/extension, lateral bending, and rotational movement of the recess 40 relative to the dome surface 50. In addition, mating surfaces between the spacer member 60 and the shells 12, 14 each provide for relative sliding or translation, as will be discussed below. The stiffness of the articulating bearing member 30 may be varied or controlled. Specifically, the concave recess 40 and the dome surface 50 each have respective radii of curvature. When the radius of curvature of the recess 40 is greater than the radius of curvature of the dome surface 50, the stiffness is decreased. When the radius of curvature of the recess 40 is smaller than the radius of curvature of the dome surface 50, the stiffness is increased.

In order to more closely mimic the behavior of a natural disc nucleus, the shells 12, 14 and any spacer member, such as but not limited to the spacer members 60, 70, may slide or translate relative to each other. The recess 40 and dome surface 50 may pivot or rotate relative to each other, as well as slide along their mating surfaces. For the flat 76 and flat surface in the recess 78, for instance, the sliding is translational. A natural disc includes a nucleus of viscous fluid, and the fluid moves away from the direction of bending or compression of the nucleus. The shells 12, 14 of the implant 10 are moved in a manner that follows the movement of the vertebrae. However, the spacer member 60 cannot enlarge in the opposite direction of the bending and compress in the direction of bending, as the natural disc can. By allowing the spacer member 60 to slide or translate relative to the shells 12, 14, the spacer member 60 may shift away from the direction of bending, thereby more accurately mimicking the compression of a natural nucleus. In addition, due to the small height of the implant 12, the pivot point of the top shell 12 relative to the bottom shell 14 is below the bottom shell 14. Accordingly, the recess 40 of the top shell 12 preferably may shift across the dome surface 50 such that the pivot point moves along with the top shell 12.

Similarly, for any vertebra-disc-vertebra segment, the center of rotation changes slightly during flexion/extension motion. To provide for this, the radius of curvature of the recess 40 may be larger than the radius of curvature of the dome surface 50 in the anterior-posterior direction. Therefore, the dome surface 50 may slide relative to the recess 40 in a manner that allows the shifting of the center of rotation.

As described above, the implant 10 may be inserted in pieces, specifically inserted sequentially or serially. As shown in FIGS. 1-5, the implant 10 has two principal pieces, namely the top shell 12 and bottom shell 14 where the top shell 12 has the concave recess 40 for receiving the dome surface 50 of the bottom shell 14. As shown in FIG. 6, the implant 10 has three principal pieces, namely the top and bottom shells 12, 14, and the spacer member 60 where the shells 12, 14 have concave recesses 40 for receiving the dome surfaces 50 of the opposite faces 62, 64 of the spacer member 60. In each of these FIGS. 1-6, at least one of the shells 12, 14 includes a ramp 90 adjacent to each recess 40. The ramp 90 may have an arcuately shaped profile against which the dome surface 50 may cam. Regardless of the order in which the shells 12, 14, or spacer member 60 are inserted through the incision in the annulus, the ramps 90 allow the pieces to be forced together by pushing any dome surface 50 against and over an aligned ramp 90 in a camming action during insertion such that the dome surface 50 cams against the aligned ramp 90. In this manner, the size of the incision made in the annulus may be minimized, as it need only provide for the largest piece to be inserted, and the annulus may be utilized for retaining the implant 10 in the nucleus space.

To further minimize the size of the incision made in the annulus, the shells 12, 14 having a smaller anterior-posterior dimension D2 than lateral dimension D1 may be inserted with a shorter, lateral end 16 leading first through a posterior incision in the annulus. The maximum clearance necessarily provided by the incision in the annulus need only be that required by the largest of the three pieces. In other words, the incision forms a deformable hole or bounded loop, and each component or piece of the implant 10 has a minimal encirclement required that the incision must permit to pass therethrough. Part of the instrumentation may include a device for cutting a precision incision into the annulus that is just large enough to insert the implant. The incision need only be large enough for the largest of the minimal encirclements of the individual pieces. Once implanted, the shells 12, 14 and/or any spacer such as spacer member 60 may be rotated within the nuclear space so that the short dimension D2 is no longer aligned with the incision in the annulus.

The shells 12, 14, and the implant 10 in general, may be rotated by an insertion tool 110 either during insertion or after assembly within the nuclear space (see FIGS. 1-6, and 10-13). The shells 12, 14, may include a post 100 including a generally circular outer surface 102 and at least one flat 104 formed on the outer surface 102. As depicted in FIGS. 10-13, the tool has several positions and has an upper, stationary jaw 112 and a lower jaw 114 which may reciprocate along the longitudinal axis of the tool 110. Referring to FIG. 10, the lower jaw 114 of the tool 110 abuts or confronts the flat 104 so that the post 100 is secured in the jaws 112, 114 so that the tool 110 and post 100 are in a locked position for insertion of the shell 12, 14. As can be seen in FIG. 11, the lower jaw 114 is in an intermediate position so that the lower jaw 114 is drawn a short distance away from the post 100 so that the lower jaw 114 does not abut or confront the flat 104. In the intermediate position, the post 100 remains captured in the jaws 112, 114. However, the post 100 may rotate relatively within the jaws 112, 114 so that the shell 12, 14 may be rotated during or after insertion in the annulus. FIG. 12 further shows a released position wherein the lower jaw 114 is drawn away from the post 100 so that the tool 110 may be removed from the post 100 and the tool 110 may be extracted from the implantation site. As can be seen, the post 100 enlarges in a direction away from the shell 12, 14 to which it is attached. The jaws 112, 114 each have opposed walls 115, 116, respectively. The walls 115, 116 are shaped as to follow the contour of the jaws 112, 114 while providing recesses 117, 118 between the walls 115, 116. Thus, the jaws 112, 114 may simultaneously encircle and manipulate a pair of posts 100 on a pair of shells 12, 14 in the manner described. The recess 118 between the walls 116 of the jaw 114 has an open terminal end 119 such that the lower jaw 114 may pass along an edge of the post 100 in a line so as to reciprocate between the locked, intermediate, or unlocked positions.

Figure 14:
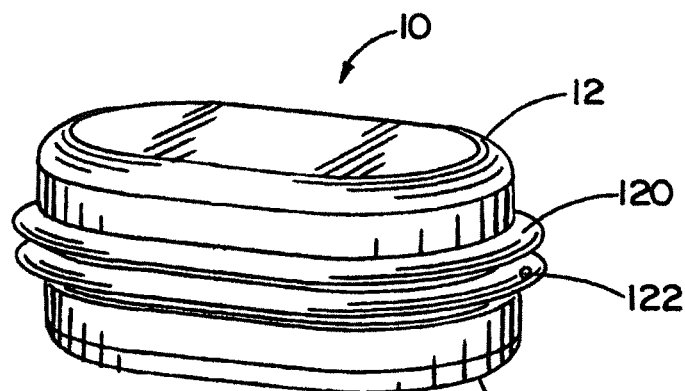
FIG. 14 is a perspective view of an implant including a curtain.
Figure 15:
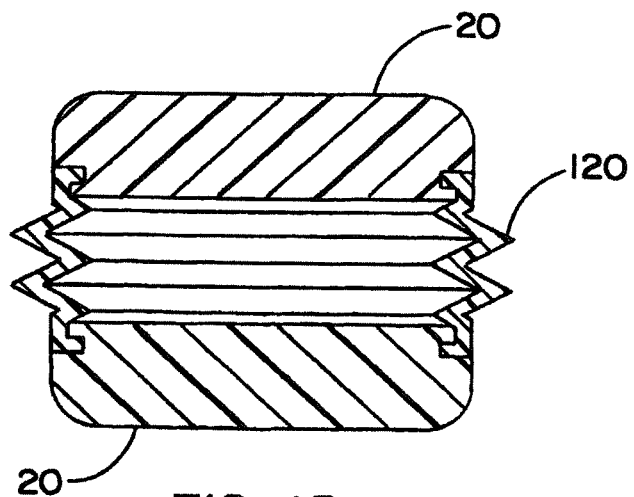
FIG. 15 is a side elevation cross-sectional view of the implant of FIG. 14.

As discussed above, the shells 12, 14 of the implant 10 do not necessarily replicate the shape of the natural nucleus so that the periphery 26 of the implant 10 may abut and stretch portions of the annulus, thereby providing tension to those portions of the annulus. It has been found that tension on the annulus alleviates pain and improves stability of the intervertebral joint. As depicted in FIGS. 14-15, an outer curtain in the form of, for instance, a pleated bellows 120 is secured to the shells 12, 14. The bellows 120 may form a seal between the shells 12, 14 and extend thereabout so that the implant 10 may be injected with a material. The material may be gas or liquid or other flowable material, such that the bellows 120 distends to apply pressure on the interior of the annulus. Preferably, the bellows is filled with saline or other non-curable material. Additionally, the injected material may slightly expand the implant 10 to provide some shock absorption and additional distraction if so desired. Furthermore, the bellows 120 prevents foreign material from entering the implant 10 which otherwise may hinder or deteriorate the performance of an articulating bearing member 30. In some embodiments, the material may be hydrogel pellets and the bellows 120 may include a permeable or semi-permeable portion to allow fluid absorption. By using pellets, the material may move within the implant 10 as any bearing member 30 articulates between the shells 12, 14. By inflating or expanding the bellows 120, or a similar structure, pressure is applied radially to the annulus to place the annulus in tension.

The bellows 120 may be attached to the shells 12, 14 by several methods. For instance, heat bonding, adhesive bonding, or a compression seal may be used to make the bellows firmly and permanently bonded to the shells 12, 14. As the bellows 120 is compressed, a portion may deflect outward. Accordingly, the compliance of the bellows 120 is preferably less in the posterior direction than in anterior and lateral directions so that, in the event the bellows 120 deflects outward, the deflection is minimized in the direction of the spinal cord. As used herein, the term compliance refers the ability for a material to stretch. The bellows 120 may be provided with a portal 122 to which a catheter or needle can be attached for injecting the bellows 120, and the portal 122 includes a sealing mechanism.

Figure 16:
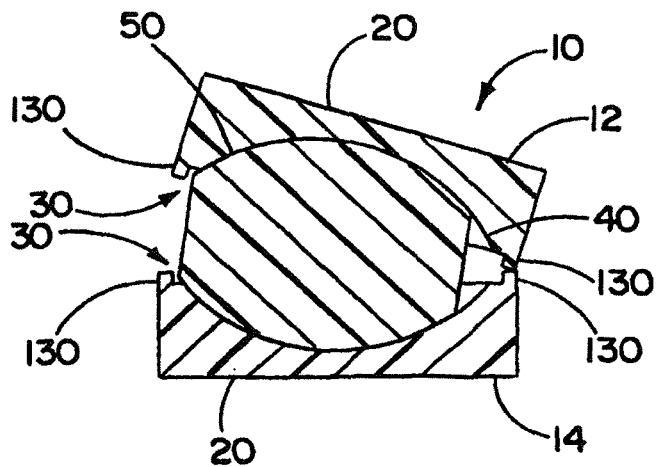
FIG. 16 is a cross-sectional view of an implant with walls to restrict motion of the shells in the anterior-posterior or lateral directions and to prevent the spacer from escaping.
Figure 17:
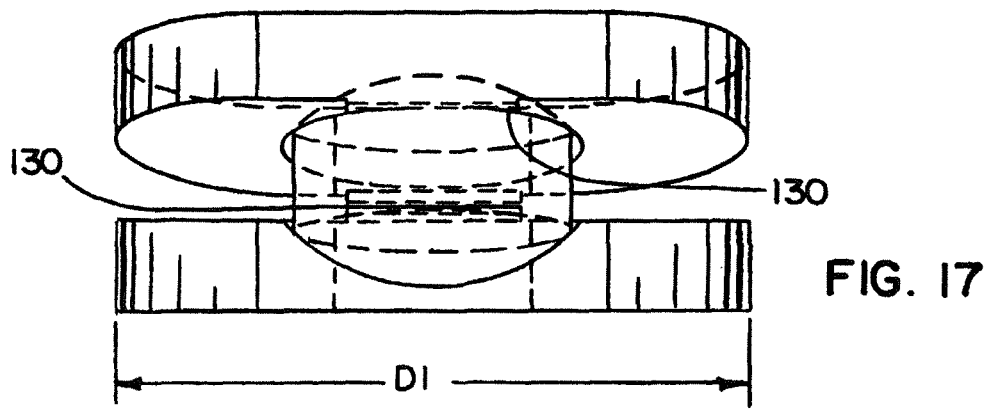
FIG. 17 is a perspective view of the implant of FIG. 17.
Figure 18:
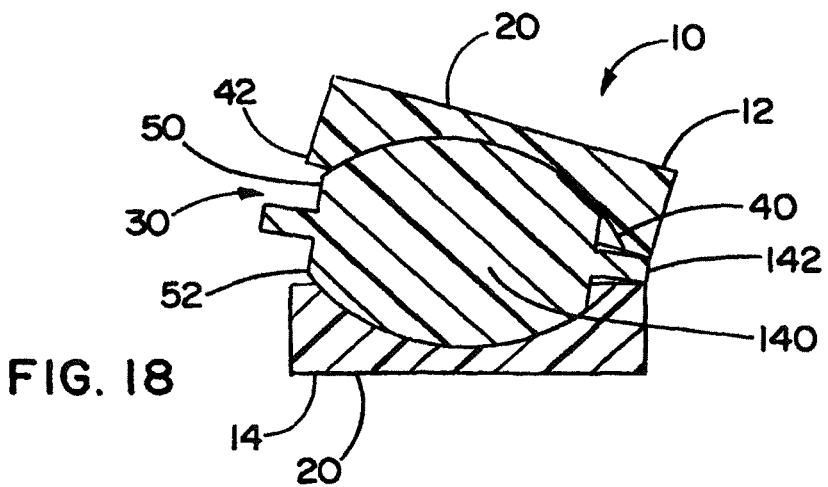
FIG. 18 is a cross-sectional view of an implant with a spacer member having a peripheral structure for restricting motion of the shells in the anterior-posterior direction.
Figure 19:
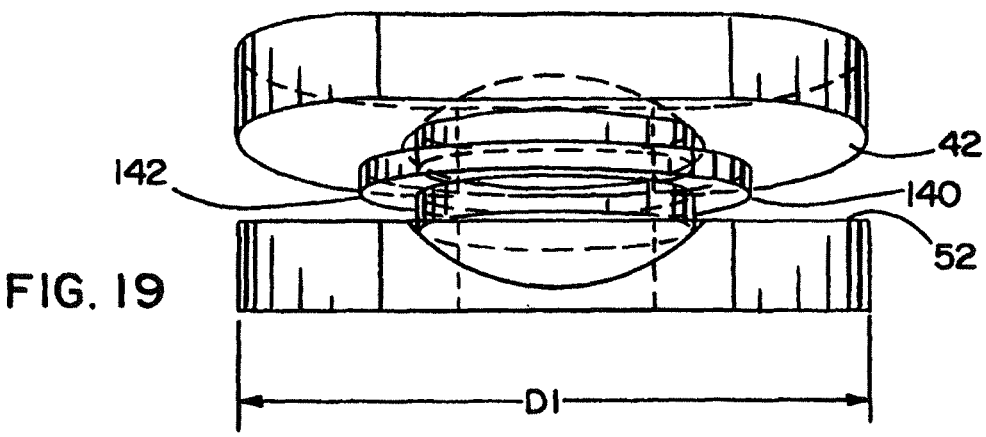
FIG. 19 is a perspective view of the implant of FIG. 18.

As discussed previously, the greatest angle of deflection between vertebrae in a natural disc is approximately 15°. The extended lateral dimension D1 of the shells 12, 14 restricts the lateral bending to 15°. However, it may be necessary to restrict the anterior-posterior bending of the implant 10. As can be seen in FIGS. 16-17, the shells 12, 14 include short walls 130 that oppose and extend toward each other such that the walls 130 abut when a 15° bend is reached. Alternatively, as can be seen in FIGS. 18-19, a spacer member 140 may include an annular ring 142 extending from its periphery and between the shells 12, 14 such that the faces 42, 52 of the top and bottom shells 12, 14 contact the ring 142 when the 15° angle is reached. The ring 142 may be made of a softer material than that of the shells 12, 14 to minimize wear, and may be resiliently compressible. The short walls 130 and the dimension of the ring 142 may be sized to provide or restrict motion of the shells 12, 14 to an angle, such as 15° or another angle, as desired.

Figure 20:
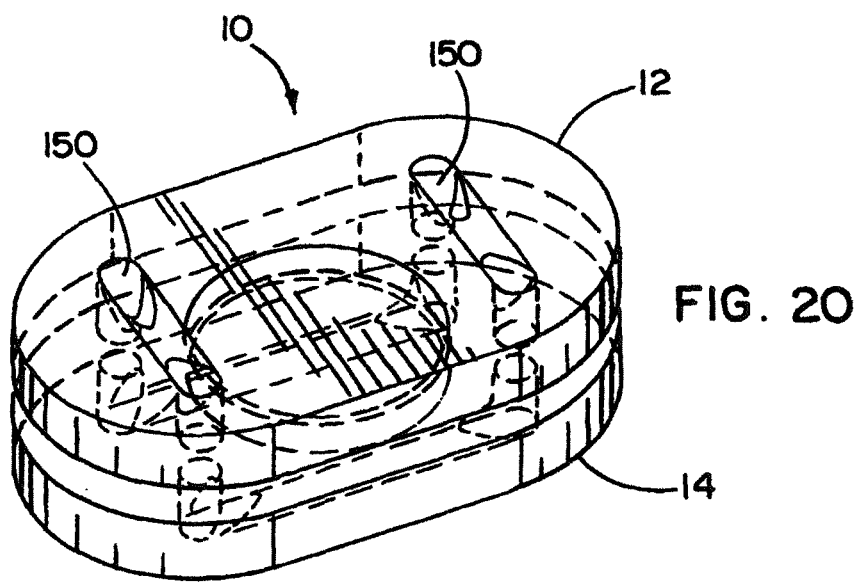
FIG. 20 is a perspective view of an implant having channels for a cable to restrict motion of the shells.
Figure 21:
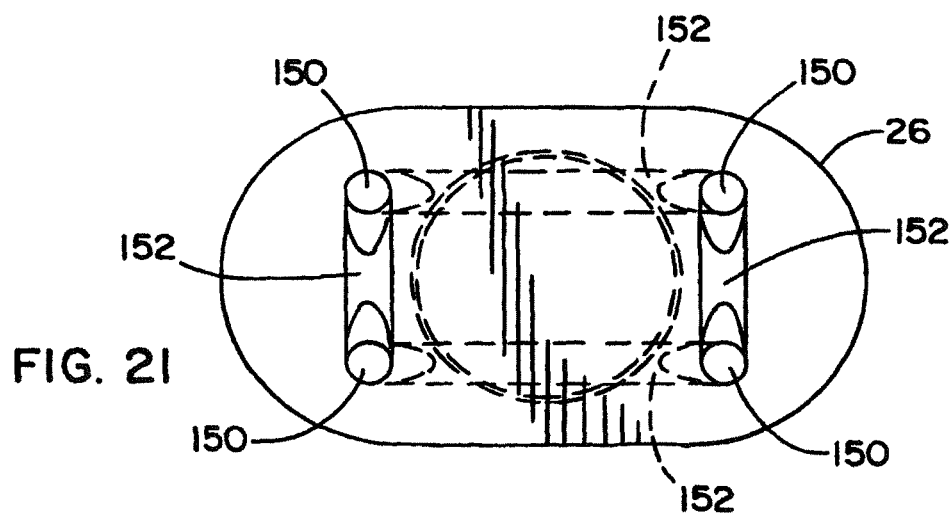
FIG. 21 is a top plan view of the implant of FIG. 20.
Figure 22:
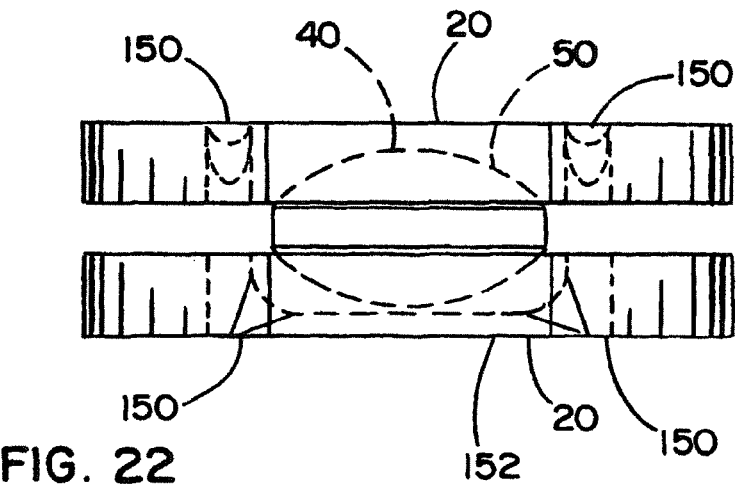
FIG. 22 is a side elevational view of the implant of FIG. 20.

In an alternative embodiment depicted in FIGS. 20-22, each shell 12, 14 includes two pairs of ports 150, each port 150 generally aligned with a port 150 of the opposing shell 12, 14 and each pair including a channel 152 recessed in the outer surface 20 of the shell 12, 14 to connect the pair. A cable or cable segments (not shown) may be threaded through the ports 150 and through the channels 152 so as to be recessed from the outer surfaces 20 of the shells such that the cable forms a closed loop. In this manner, the sides of the shells 12, 14 opposite the direction of bending can only be separated to a degree provided by the length of the cable. The cable is provided with length such that the degree of separation between the shells 12, 14 does not exceed 15°, or any other angle, in the anterior-posterior direction. Furthermore, the cable arrangement prevents the shells 12, 14 from separating from each other and blocks the space between the shells 12, 14 so that the spacer member 60 therebetween cannot come loose and escape from between the shells 12, 14.

Figure 23:
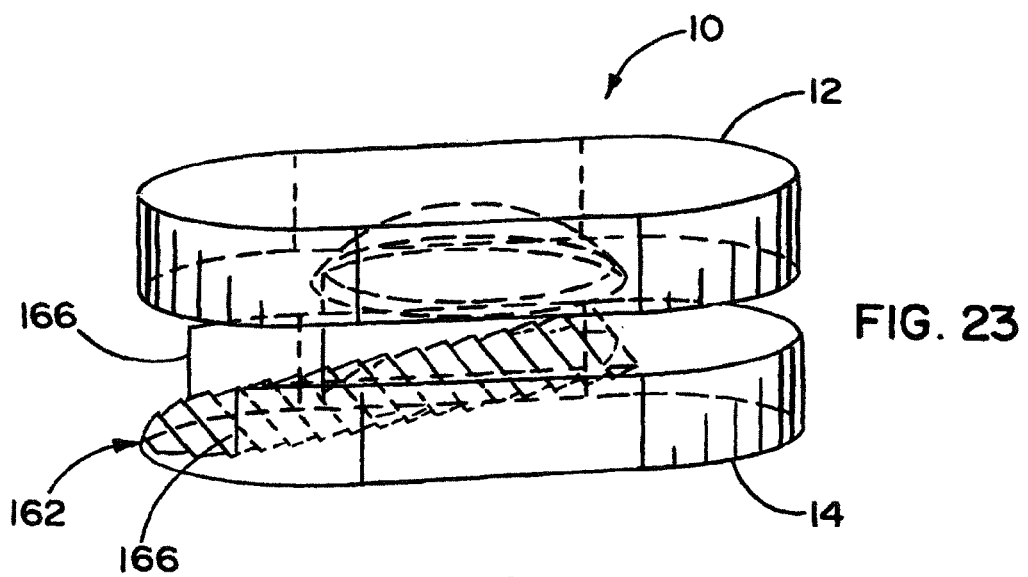
FIG. 23 is a perspective view of an implant and a spacer member in partial phantom.
Figure 24:
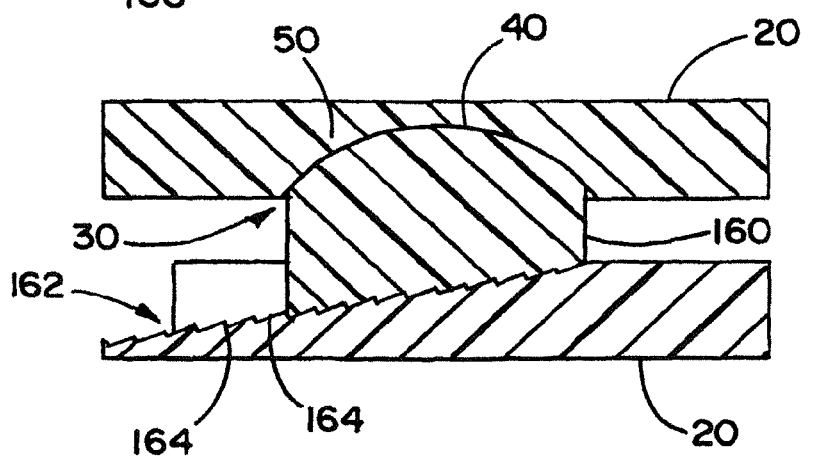
FIG. 24 is a cross-sectional view of the implant of FIG. 23.
Figure 25:
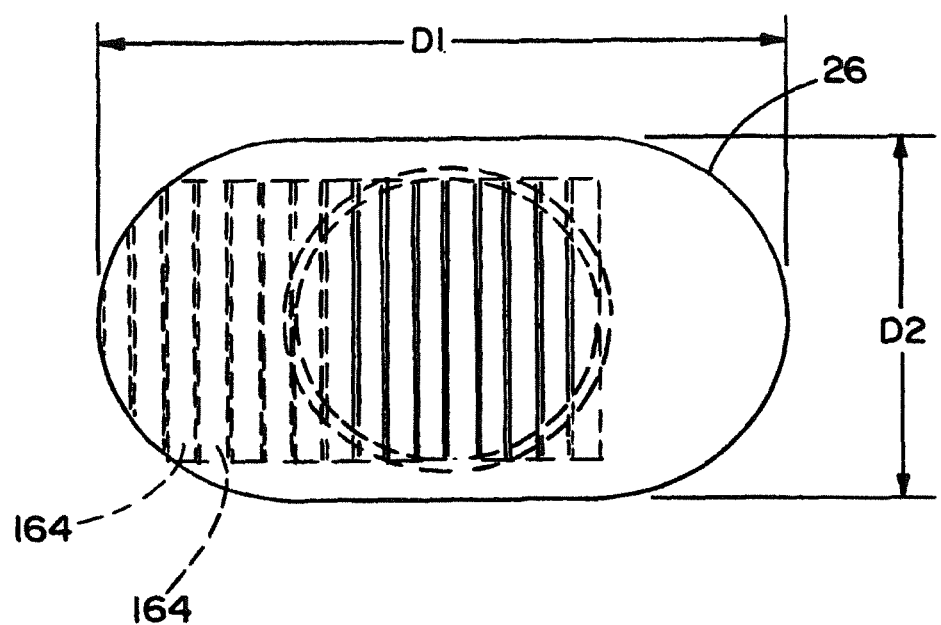
FIG. 25 is a top plan view of the implant of FIG. 23 in partial phantom.

Referring now to FIGS. 23-25, an implant 10 is depicted having top and bottom shells 12, 14 and a stepped spacer member 160. The bottom shell 14 includes an inclined stepped ramp 162 with, preferably, steps 164 aligned in the anterior-posterior direction and sidewalls 166 to the sides of the steps 164. The steps 164 rise toward the center of the shell 14, and a dome surface 50 on the opposite side of the spacer member 160 contacts and is received in a recess 40. The shells 12, 14 may be inserted in the nucleus space with the stepped ramp 162 aligned with the incision in the annulus. In one form, the dome surface 50 of the spacer member 160 may cam against the top shell 12 while being forced between the shells 12, 14 and into the nuclear space. The stepped spacer member 160 may be forced between the shells 12, 14 so that the stepped spacer member 160 cams against and ratchets up the steps 164. The sidewalls 166 are positioned so that the spacer member 160 may slide or translate a short distance in the anterior-posterior direction along the steps, while also preventing overtranslation. Once the stepped spacer member 160 is inserted, the stepped shell 14 may be rotated so the ramp 162 is no longer aligned with the incision of the annulus. To prevent the spacer member 160 from repositioning to a lower portion of the stepped ramp 162 once implanted, a stop (not shown) may be provided, or the steps 164 may be canted such that each step 164 is angled downward toward the inboard edge of the step 164, and the steps 164 and the bottom surface of the stepped spacer member 160 interlock, as is depicted. Alternatively, the bottom shell 14 including the stepped ramp 162 may be inserted, and then the spacer member 160 and the top shell 12 may be inserted together with the dome surface 50 received in the concave recess 40. Accordingly, both the spacer member 160 and the top shell 12 are forced into the nuclear cavity such that the spacer member 160 ratchets up the steps 164 of the bottom shell 14. As a further alternative, the top and bottom shells 12, 14 and the stepped spacer member 160 may be inserted together with the spacer member 160 positioned at the lower steps 164 so the implant has a reduced size or thickness during insertion into the nuclear cavity.

Figure 26:
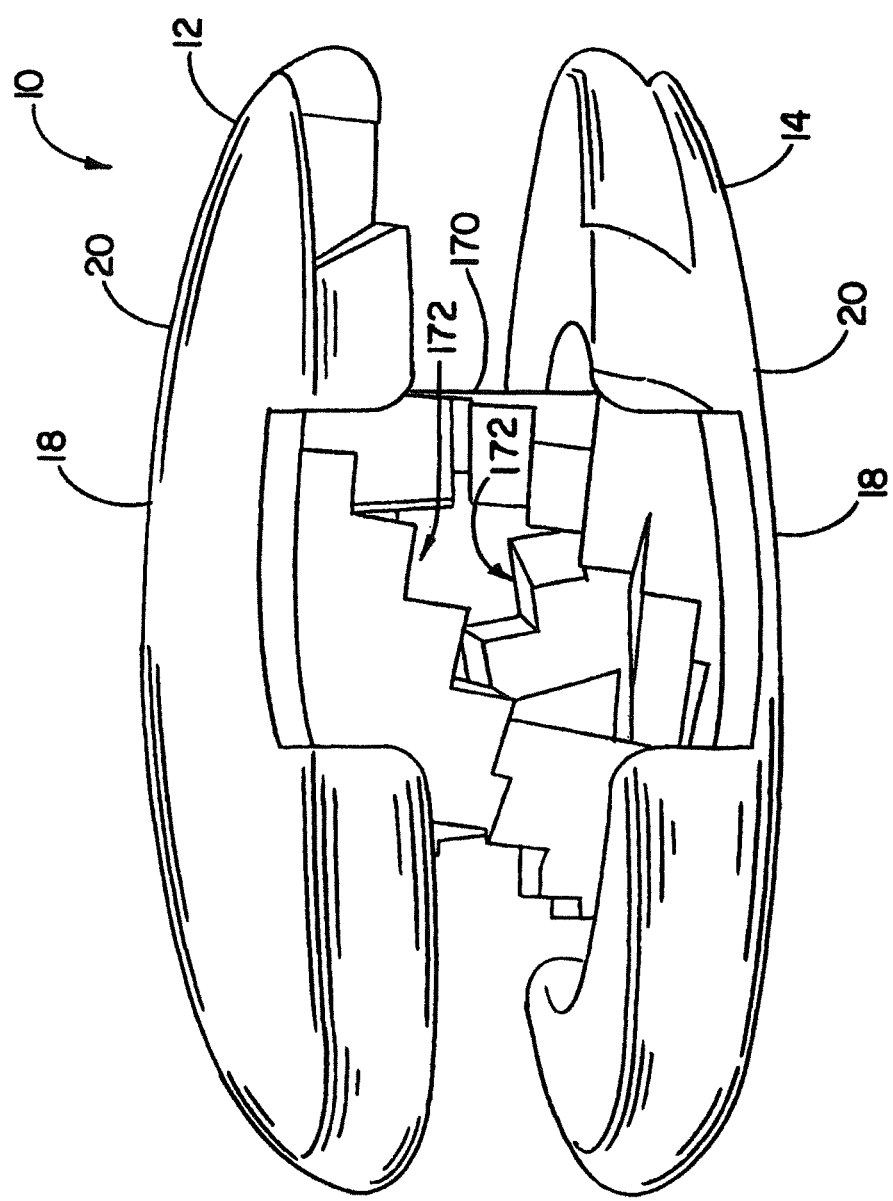
FIG. 26 is a perspective view of an implant having a helical insert.
Figure 27:
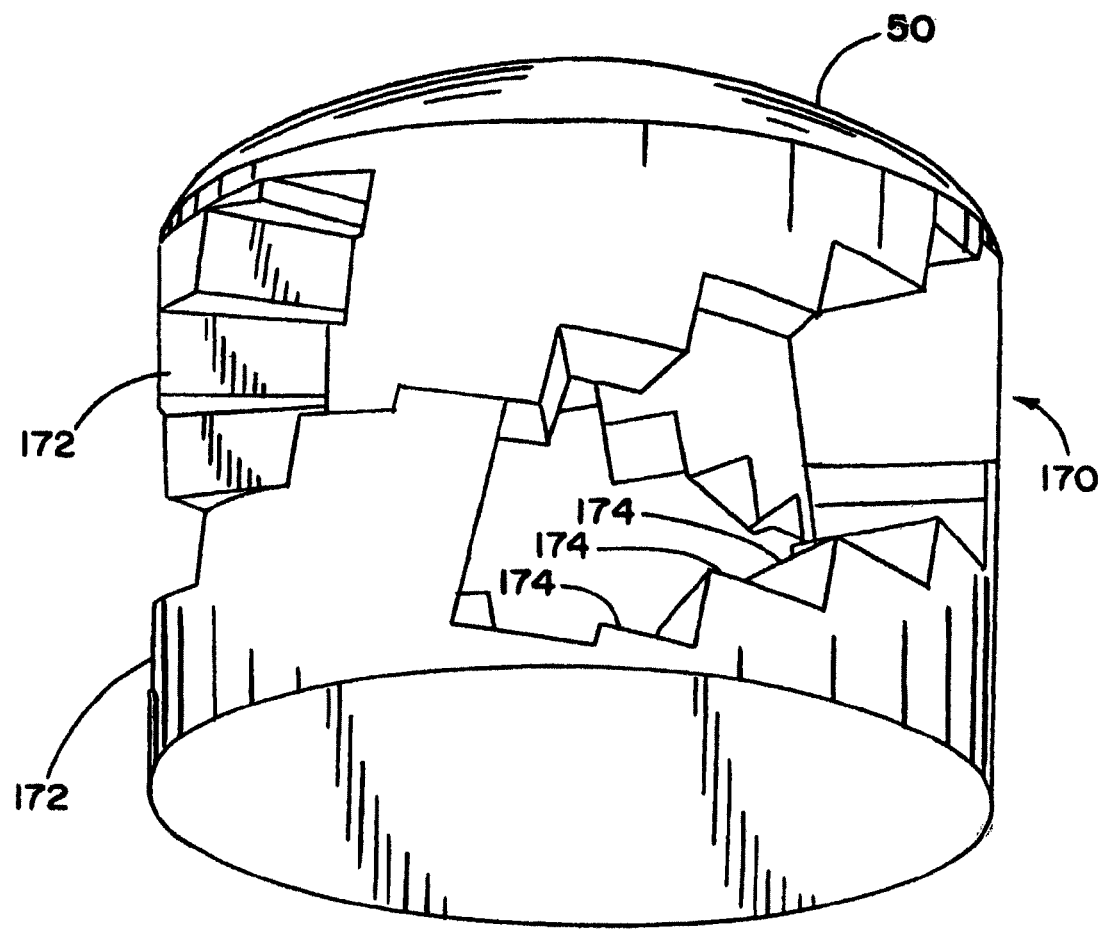
FIG. 27 is a perspective view of the helical insert of FIG. 26.

Referring to FIGS. 26-27, an implant 10 inserted in a collapsed or compressed state or arrangement and then expanded is depicted having top and bottom shells 12, 14 and a helically stepped spacer member 170. Both shells 12, 14, but preferably one shell 12, 14, have a concave recess 40 into which a dome surface 50 formed on the spacer member 170 is received. The spacer member 170 has two opposing stepped helical wall sections 172. In some forms, one of the helical walls sections 172 is integral with one of the shells 12, 14, while in other forms both helical wall sections 172 include a dome surface 50 received by a concave recess 40 in the respective mating shells 12, 14. The helical wall sections 172 have opposing helically arranged steps 174. The implant 10 is inserted into or assembled within the nucleus in a compressed arrangement with the helical wall sections 172 fully intermeshed with each other. Once inserted, the helical wall sections 172 may be rotated relative to each other such that the opposing steps 174 of the helical wall sections 172 ratchet against each other and thereby expand the implant 10 to an expanded arrangement. The implant 10 may be constructed to prevent undesired repositioning of the helical wall sections 172. Similarly to the implant 10 described above having a stepped ramp 162, the steps 174 of the helical wall sections 172 may be canted forward in the direction of rotation for expansion to prevent or impede repositioning, or a stop (not shown) may be provided. As a further alternative, the implant 10 may be provided with a compression and/or torsional spring (not shown) so that, once implanted, the helical wall sections 172 are automatically forced open and rotated to an expanded arrangement, and the helical wall sections 172 may then hold the shells 12, 14 in the expanded arrangement.

Figure 28:
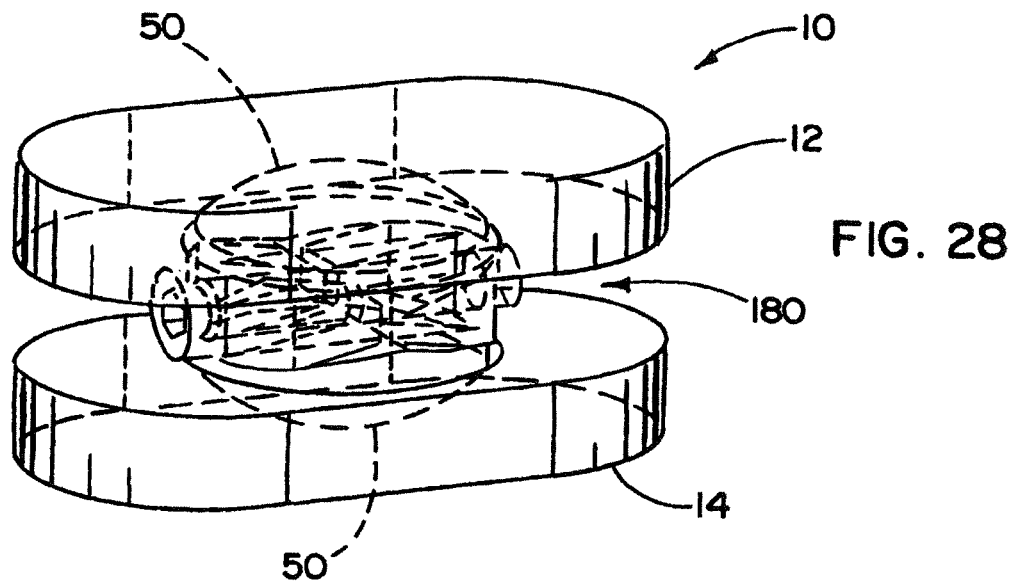
FIG. 28 is a perspective view of an implant having a rotational member for directing wedges.
Figure 29:
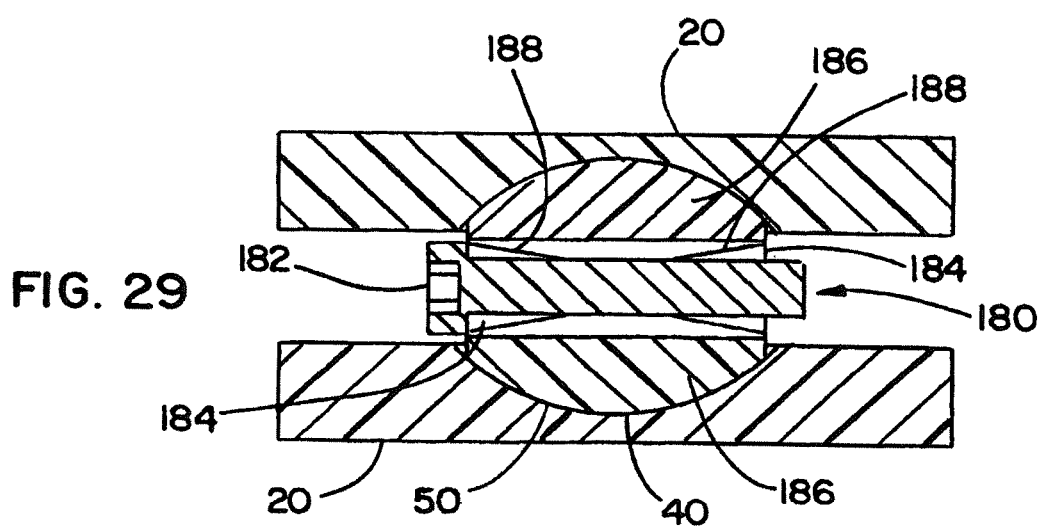
FIG. 29 is a cross-sectional view of the implant of FIG. 28.
Figure 30:
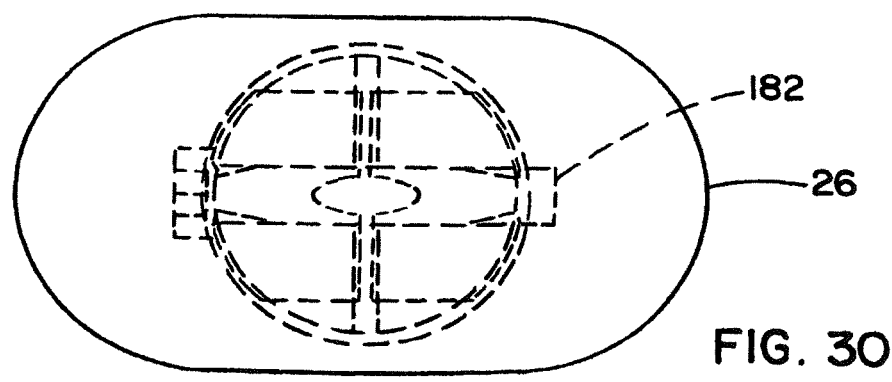
FIG. 30 is a top plan view of the implant of FIG. 28 in partial phantom.

As a further alternative, FIGS. 28-30 depict an implant 10 having top and bottom shells 12, 14, and a spacer member 180 which includes a rotating member 182 that rotates around its longitudinal axis connected to a pair of opposed wedges 184 and a pair of hemispherical members 186. Each hemispherical member 186 includes a dome surface 50 received within a recess 40 in the respective shell 12, 14. The rotating member 182 is threaded within the wedges 184. Turning the rotating member 182 in a particular direction forces the wedges 184 from a compressed arrangement where the wedges 184 are separated to an expanded arrangement with the wedges 184 closer together or abutting each other. The wedges 184 in the compressed arrangement are generally positioned laterally to a space 186 between the hemispherical members 186. Turning the rotating member 182 to draw the wedges 184 closer pulls the wedges 184 to a position within the space 186. In doing so, wedge surfaces 188 abut the hemispherical members 186, thereby forcing the hemispherical members 186 away from each other and forcing the implant to the expanded arrangement. The implant 10 may be inserted in the compressed arrangement, and then expanded as described. As alternatives, a single wedge may be utilized with a rotating member rotationally secured (not shown) to either a shell or a hemispherical member, or the wedges may expand the implant by being forced outward, away from each other, as opposed to being forced inward, as described. It is preferred that an end of the rotating member 182 used to effect its rotation is positioned to face the incision during its rotation.

Figure 31:
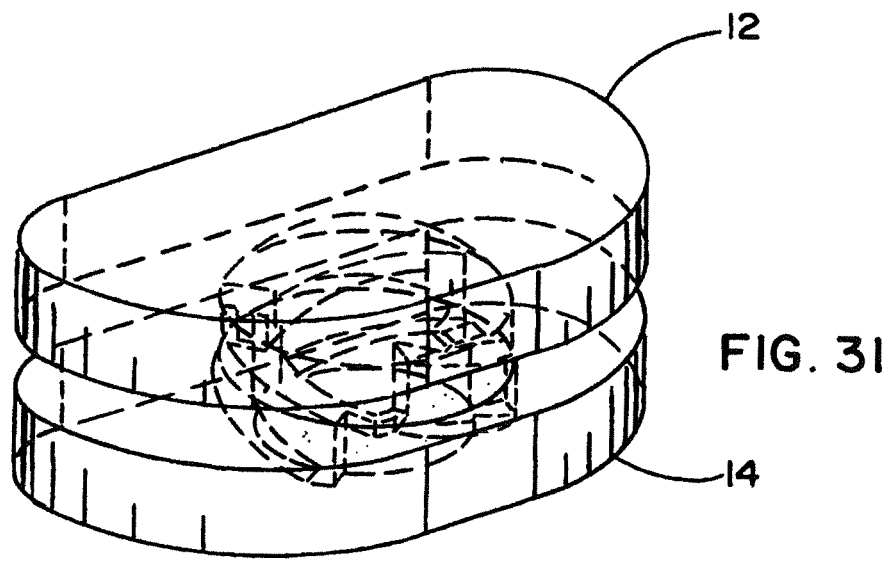
FIG. 31 is a partial phantom perspective view of an implant with a camming spacer member.
Figure 32:
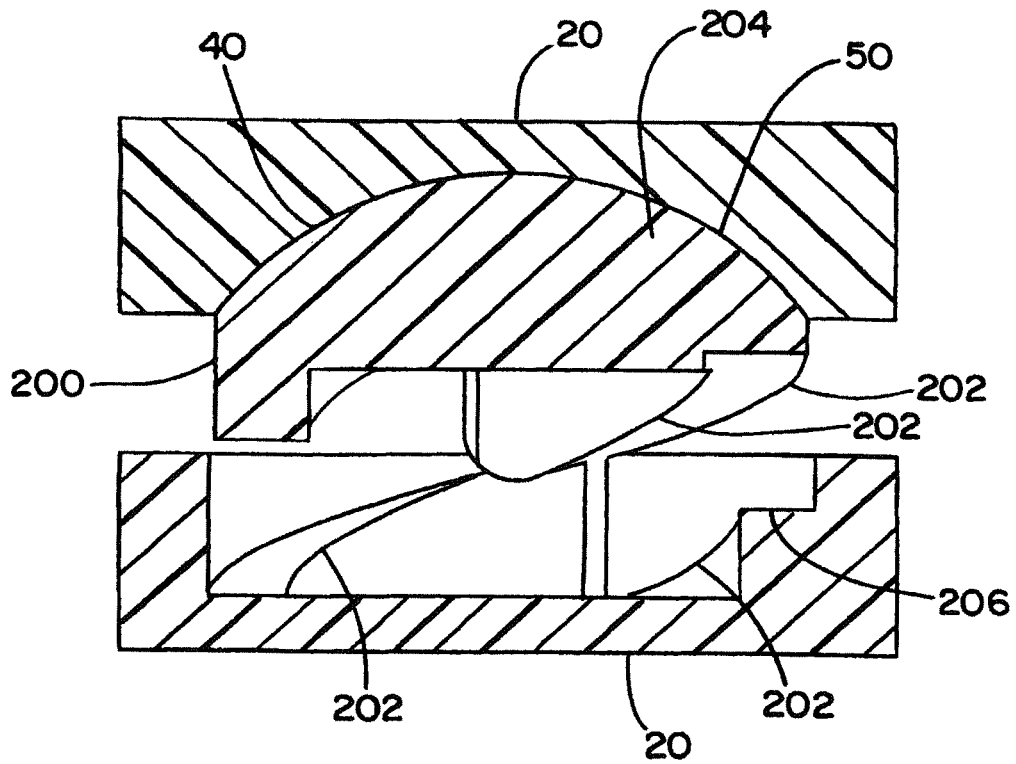
FIG. 32 is a cross-sectional view of the implant of FIG. 31.

Referring now to FIGS. 31-32, an implant 10 is depicted having a spacer in the form of cam member 200 with cam surfaces 202 such that the implant 10 may be in inserted in a compressed arrangement, and the cam surfaces 202 may then rotate to expand the implant 10. The cam member 200 includes a camming dome 204 having a dome surface 50 received in a recess 40 in the top shell 12. The calming dome 204 preferably has three or more cam surfaces 202 mating with opposed cam surfaces 202 of the bottom shell 14. In the compressed or unexpanded arrangement, the cam surfaces 202 of the camming dome 204 and bottom shell 14 are fully interlocked and intermeshed. The camming dome 204 may be rotated relative to the bottom shell 14 such that the mating cam surfaces 202 cam against each other, thereby forcing the camming dome 204 up and expanding the implant 10 from a compressed arrangement to an expanded arrangement. At the highest point 206 of the cam surfaces 202 of the bottom shell 14, there is a hump or other stop, beyond which the cam surfaces 202 may seated to prevent the camming dome 204 from repositioning to a lower level. Alternatively, a pair of camming domes 204 may be provided with cam surfaces 202 therebetween such that the camming domes 204 may be rotated relative to each other to expand the implant 10.

Figure 33:
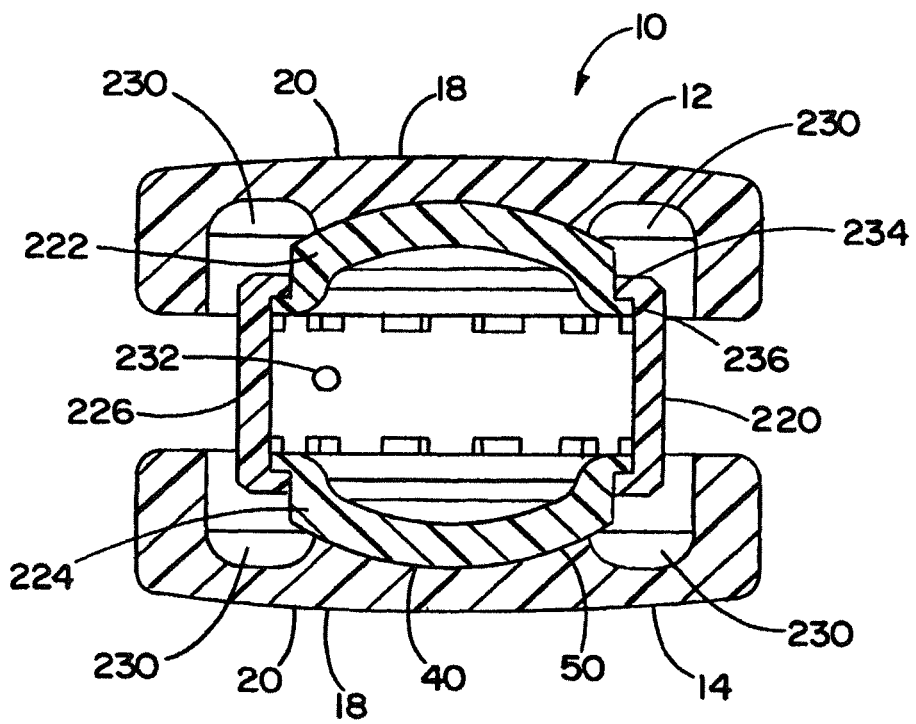
FIG. 33 is a cross-sectional view of a first implant with an expandable canister.
Figure 34:
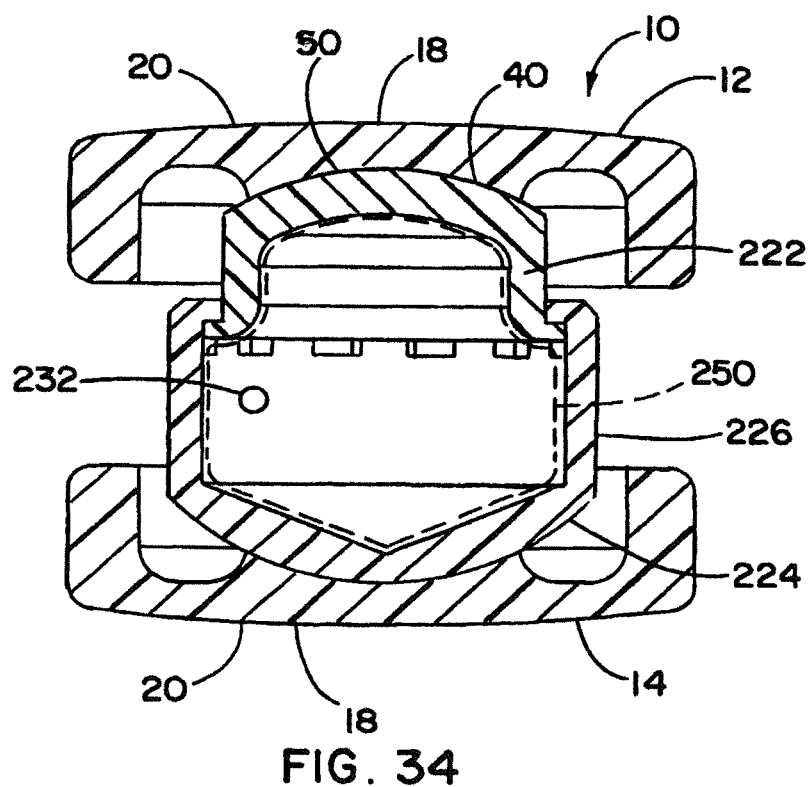
FIG. 34 is a cross-sectional view of a second implant with an expandable canister.

In an alternative embodiment of the expandable implant, FIGS. 33-34 depict implants 10 with top and bottom shells 12, 14 and an expandable canister. In FIG. 33, a canister 220 has a top cap 222, a bottom cap 224, and a sidewall 226. The top cap 222 and bottom cap 224 each have a dome surface 50 mating with a recess 40 on respective shells 12, 14. The implant 10 is inserted in the nucleus space in a compressed or unexpanded arrangement, and the shells 12, 14 have annular recesses 230 for receiving the sidewall 226 when the implant 10 is in the compressed arrangement. The sidewall 226 includes an inlet 232 so that the canister 220 may be expanded by injecting the canister 220 with a flowable material, thereby expanding the implant 10 to the expanded arrangement. The sidewall 226 has an inwardly extending lip 234 on its top and bottom edge which interferes with an outwardly extending lip 236 on each of the caps 222, 224 when the canister 220 is fully expanded. Referring to FIG. 34, an alternative canister 240 is depicted where the bottom cap 224 is integral with the sidewall 226. The canister 220 may preferably be filled with a curable material so that the material does not leak from the expanded canister 220. In these embodiments, the caps 222, 224 should form a sufficient seal with the sidewall 226 so that the material is retained within the canister 220, 240. As an alternative, one of the caps 222, 224 may be integral with one of the shells 12, 14.

Alternatively, the canister 220 may be filled with fluid, or may be filled with elastomeric material so that the canister 220, 240 provides some degree of shock absorption. As a further alternative, a balloon 250 may be used instead of the canister 220, 240. If only a balloon is used, a deflated balloon may be pre-positioned within the shells 12, 14 when the implant 10 is inserted in the nuclear space, or a deflated balloon may be inserted after the shells are implanted. In order to fill the balloon 250, it should have a port or inlet aligned with the inlet 232 in the sidewall 226 for receiving the injected material from, for instance, a catheter. When the catheter, for instance, is removed after filling the implant, the balloon or canister should be sealed. Accordingly, it is preferred that a self-sealing valve or valve-less connection is made between the injection device and the balloon or canister. Alternatively, the injected material may seal the balloon or canister, such as when the material is curable. When a balloon is used with the sidewall 226, the function of the sidewall 226 is to limit or reduce the lateral deformation of the balloon so that the height of the implant 10 is maintained.

If a balloon 250 is used without being enclosed and generally immobilized in another structure and is filled with a non-curable material, a non-compliant or minimally compliant balloon may be used to maintain rigidity during physiological loading. The balloon may be filled with, as examples, saline, silicone oil, or PEG solution. If the balloon is filled with curable material, the balloon may be formed of both compliant and non-compliant material. Suitable curable materials include but are not limited to, as examples, PMMA, calcium phosphate, polyurethane, and silicone.

In some forms of the expandable implant, the ability to control the degree of expansion is provided. For instance, the wall sections 172 of the helical stepped spacer member 170 may be rotated to a desired height, or the expansion of the canister 220 may be controlled by controlling the amount of injected material. Both the height or expansion of the implant 10 and the distraction force on the vertebrae may be monitored and controlled. However, it is preferred from a clinical standpoint to expand the implant 10 to a pre-determined distraction force so the expansion is performed with respect to contact pressure on the end plate of the vertebrae.

Each polyaxial bearing member 30 as described herein has an outer contour mating with a similar shaped recess. Though the outer contour of the dome surface may be a partial spheroid, hemispherical, or similar structure, it should be noted that other shapes, such as oblong or parabolic, may offer greater function. Alteration of the shape of the dome surface may be utilized to provide different ranges of motion to the polyaxial bearing member 30. As depicted, the spacers have one or two arcuate dome surfaces with radii of curvature that, if they were to form a complete spheroid, would be prohibitively large for use in the intervertebral space. Alternatively, a spacer member may be provided as a rigid ball or semi-rigid arcuate ball.

Advantageously, the dome surface and recess bearing member 30 produces an interface between the shell and the spacer member that allows greater freedom for the shells to be relatively oriented when implanted. Specifically, the shells may orient in an angle appropriate for various intervertebral disc levels, as discussed above. For instance, at different levels, such as the L5/S1 level, the vertebrae are oriented in the angle for maintaining a lordotic shape in the spine. With the free rotation of the shells against the bearing member portion, the shells may angularly adjust in accordance with the natural curvature of the spine without creating uneven stress distributions on the end plates of the vertebrae.

Materials for the shells 12, 14, and any spacer such as spacer member 60 may be selected to provide certain properties. The components of the implants may be coated with polyurethane to reduce damage to surrounding tissues during implantation and to reduce abrasiveness during micromotion between the components and surrounding tissues when in situ. Materials may be selected to provide desirable wear characteristics between sliding surfaces, and may be selected to provide radiotranslucency. In any event, the materials for the shells 12, 14, and any components of the articulating bearing member 30 are generally rigid so that the implant 10 is capable of supporting the cyclic compressive loads experienced by the implant 10, as a natural disc would experience. Some examples of materials are metals, ceramics, plastics, composite materials and elastomers. Metals may include surgical grade stainless steel, Co—Cr alloys, liquid metal, titanium, and titanium alloys. Ceramics may include alumina, and zirconia. Plastics may include polyethylene, polypropylene, pyrolytic carbon, PEEK™, and BioPEKK™. Composites may include carbon fiber PEEK and carbon fiber BioPEKK. Elastomers may include polyurethane. Non-metallic materials benefit from being radiolucent and from not causing artifact during imaging, such as radiographic, magnetic resonance, or CAT scan. With non-metallic materials, it may be beneficial to include radio opaque markers in the device to assist in identification in an image. For instance, one or more markers may be provided for each shell such that the orientation and position of each may be seen, and the markers may be of different sizes so that the marks of each shell may be distinguished and recognized. By way of example, each discrete member of the implant may be provided with a marker of non-uniform shape, or two transverse markers of different size or shape, such that when viewed on an image the markers clearly present the position and orientation of each member. It should be realized that the above-named materials are only examples, and this is not an attempt to catalog a complete list of materials which may be used.

The spacer member and the shells may be made from matching material, or may be made from different materials. Generally, use of a non-metallic material for the shell would benefit from using a non-metallic material for the spacer member to avoid artifact during imaging. However, use of a metallic material on the wear surfaces may improve the wear resistance on the articulating and sliding surfaces.

Referring now to FIGS. 35-50, further embodiments of an implant or artificial disc device 300 are illustrated. The implant 300 has a body 301 that can be formed from two pieces including a lower member or shell 312 and an upper member or shell 314 having respective outer surfaces 320, 322 for contacting the endplates of adjacent vertebrae. As with the previous embodiments, the convexity or concavity of the outer surfaces 320, 322 of the implant members 312, 314 may match or slightly mismatch the contours of the adjacent vertebrae. The outer surfaces 320, 322 may also be flat, and one or the other may be either flat, convex, or concave while the other is not. Also like the previous embodiments, the surfaces 320, 322 preferably need not have protrusions or the like for securing the implant to the endplates, though these may be provided.

To allow the members 312, 314 to shift relative to each other, a bearing interface 315 is formed between the members 312, 314 via bearing members or portions of the members 312, 314, as has been described for the previous embodiments. More particularly, the lower member 312 has an arcuate or dome bearing portion 319 which can have a substantially matching configuration to the recessed bearing portion 317 of the upper member 314. Manifestly, the recess 317 and dome portion 319 could be reversed to be formed on the lower member 312 and upper member 314, respectively. In addition, the dome bearing portion 319 may have a mismatched configuration relative to the recessed bearing portion 317, such as has been described above to provide a desired articulation stiffness. It should be noted that the motion could be limited to a single axis, two axes, or be polyaxial. For example, motion limiters (not shown) may be located on the members 312, 314, or a single axis joint may be formed with bearing members having an elongated concave or convex surface.

Accordingly, like the previously described bearing member 30, the dome bearing portion 319 fits into the arcuate recess 317 so that the respective surface 319*a* and 317*a* thereof are in preferably substantially flush, sliding contact with each other to allow the shell members 312, 314 to turn or pivot and arcuately slide or translate relative to each other. This relative shifting between the shell members 312, 314 is similar to that previously described for the other implants herein. Accordingly, herein the term bearing member can be a bearing portion of the lower member 312, the upper member 314, or both, or a separate piece disposed between lower and upper shell members, as previously indicated.

The implant 300 is inserted between adjacent lower and upper vertebrae with the shell members 312 and 314 preferably connected to each other as will be described hereinafter. The implant 300 and the shells 312, 314 have the above-described racetrack shape having an anterior-posterior dimension D2 that is smaller than a lateral dimension D1 including sides 303*a* and 303*b*. The implant 300 is inserted advantageously utilizing a narrower, leading or forward end 304 having the minor dimension D2. The implant 300 has a longitudinal axis extending from the leading ends 304*a*, 304*b* to respective trailing ends 306*a*, 306*b*, and a lateral axis extending between the substantially longer sides 303*a*, 303*b*. The longitudinal and lateral axes of the implant members 312, 314 define general planes of each thereof. Consequently, the incision 308 in the annulus 309 need only have a length sufficient to fit the lateral width D2 therethrough. During or after insertion, the implant 300 may be rotated so that the smaller, lateral dimension D2 is no longer exactly aligned with the incision 308 and inserted to bring the larger, lateral dimension D1 into at least partial alignment with the incision 308 after implantation. In this manner, the size of the incision 308 made in the annulus 309 for insertion is minimized. In addition, by turning the implant 300 in the nuclear space, it is captured in the space by the annulus 309 and is unlikely to back out of the smaller incision 308 generally aligned with one of the longer sides 303*a*, 303*b* of the implant 300 adjacent thereto.

With the preferred oval or racetrack configuration, the leading end 304 of the implant 300, and specifically the ends 304*a*, 304*b* of the disc shell members 312, 314 are curved in the general plane of the members to ease insertion through the incision 308. On the other hand, once the implant 300 has been inserted and rotated such that the substantially longer sides 303*a*, 303*b* of the implant 300, and particularly the members 312 and 314 thereof, are aligned with the incision, the substantially longer sides 303*a*, 303*b*, in addition to their length, make it highly unlikely that the disc members 312, 314 will back out through the incision 308 after implantation. Moreover, in the present preferred embodiment the substantially longer sides 303*a*, 303*b* are generally straight, further contributing to the resistance to backing out by the implant members 312, 314.

As previously described, an optional ramp 90 could be provided to facilitate alignment of the implant members as the members are preferably sequentially inserted with one member already inserted in the nuclear space between adjacent vertebrae 321 and the other member inserted into an operable configuration relative to already inserted member via the ramp 90. On the other hand, the preferred disc device 300 is inserted as a single unit so that the members 312, 314 are inserted together through the annulus incision 308. Accordingly, alignment structure such as the aforedescribed ramp for bringing the shell members together in an operable configuration in the vertebral disc space need not be provided. In this regard, the upper member 314 can have flats 390 in the general plane of the upper member on either side of arcuate recess 317.

Figure 47:
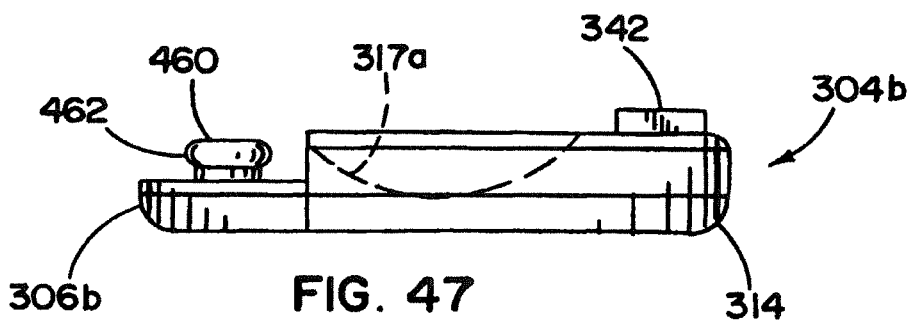
FIG. 47 is a side elevational view of the upper member showing an arcuate recess and a grip post for securing with the inserter tool during implantation.
Figure 48:
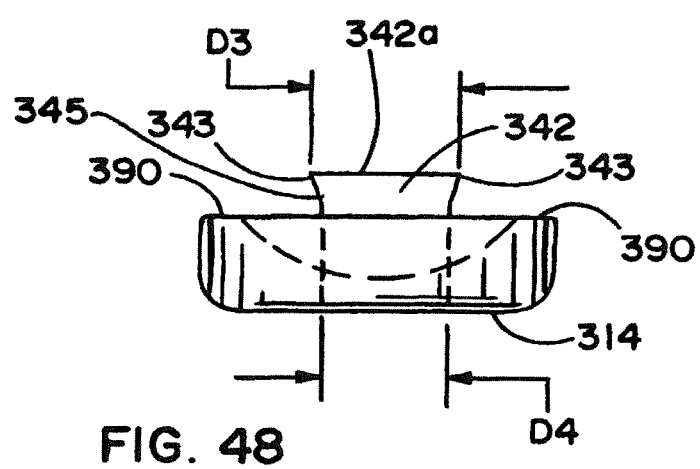
FIG. 48 is a side elevational view of the upper member showing the dove-tail configuration of the projection of the trailing end of the upper member.
Figure 50:
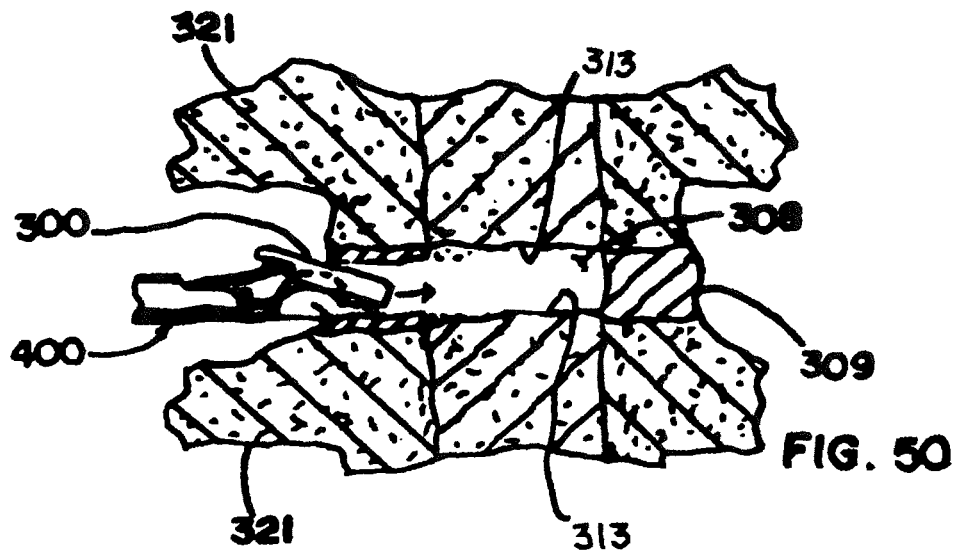
FIG. 50 is a partial cross-sectional view of the spinal section of FIG. 49 showing the artificial disc device in the insertion configuration being inserted through the annulus.
Figure 51:
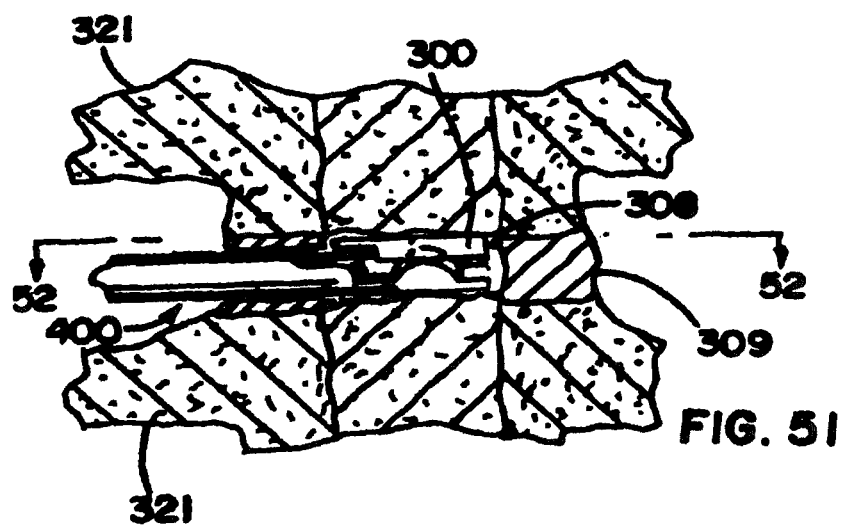
FIG. 51 is a partial cross-sectional view corresponding to FIG. 50 showing the members released and in the operable configuration in the nuclear space.
Figure 52:
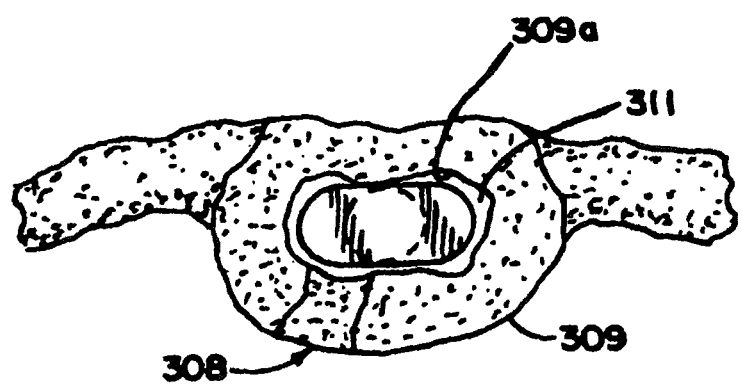
FIG. 52 is a cross-sectional view taken along the line 52-52 of FIG. 51 showing the artificial disc device turned to an implanted orientation from the insertion orientation.

The artificial disc members 312, 314 are preferably connected to each other so that the disc device 300 can be inserted as a single unit or disc assembly, as previously mentioned. To this end, the disc members 312, 314 are connected so that they assume an insertion configuration that enables efficient implantation of the disc assembly 300 while minimizing the invasiveness thereof in terms of the incision size required therefor in the annulus 309. As shown in FIGS. 47 and 50, the insertion configuration of the disc unit 300 is preferably a wedge configuration so that a low profile, leading end 304 of the unit 300 is formed. At the trailing end 306 of the unit 300, the disc members 312, 314 taper away from each other so that the trailing end 306 has a larger profile than the leading end 304.

Thus, the insertion configuration for the artificial disc assembly 300 allows a surgeon to initially insert the leading end 304 through the narrow, slit incision 308 formed in the fibrous annulus material with resistance to the initial stage of the implant insertion kept to a minimum. Continued insertion of the unit 300 spreads the incision 308 apart to allow the entire implant 300 including the enlarged trailing end 305 to be fit therethrough and into the nuclear space 311. The bearing portion or interface 315 between the implant members 312, 314 acts as a fulcrum between the members 312, 314. During initial insertion, the force exerted on the top and bottom surfaces 322, 320 is on the fore of the fulcrum of the bearing portion 315. As the implant 300 continues into the annulus 309, the force will increase on the fore, as well as act upon a greater portion of the surfaces 320, 322 as they enter the annulus 309. At a point, the force exerted on the aft portion of the fulcrum of the implant members 312, 314 will exceed that on the fore of the fulcrum to a sufficient extent that the implant members 312, 314 are shifted to the operable configuration, as will be described below. As such, the wedge insertion configuration assists both in inserting the leading end 304 of the implant 300 and in enabling efficient shifting of the disc device 300 to the operable configuration in the nuclear space 311 between the adjacent upper and lower vertebrae 321 and, specifically, the end plates 313 thereof.

More particularly, the respective axes 312a and 314a of the disc members 312 and 314 form an insertion wedge angle ω which, along with the length the disc members 312,314, dictates the extent of the separation of the trailing member ends 306a and 306b. To maintain the insertion configuration of the disc unit 300, the disc members 312, 314 have a releasable connection 340 formed between the respective leading ends 304a and 304b thereof. The releasable connection 340 sets the disc members 312, 314 in their insertion configuration with the predetermined insertion wedge angle ω formed therebetween. In the preferred and illustrated form, the releasable connection 340 cooperates with the dome bearing portion 319 and the recess portion 317 of the respective members 312, 314 to form the insertion wedge angle ω of a particular disc unit 300.

Figure 35:
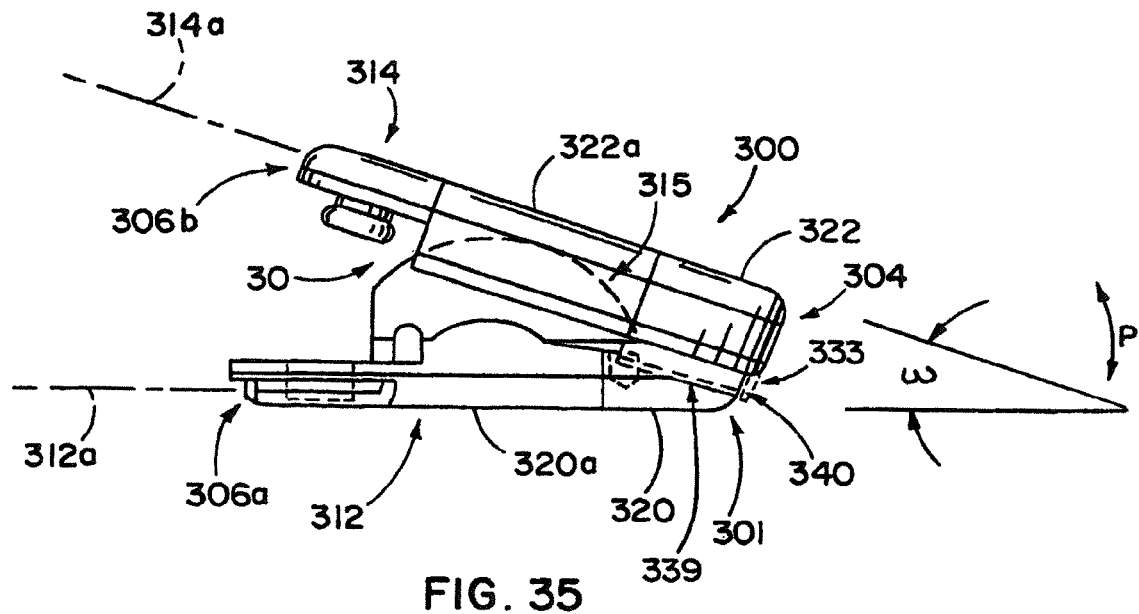
FIG. 35 is a side elevational view of an artificial disc device in accordance with the present invention showing upper and lower members releasably connected in an insertion configuration.
Figure 41:
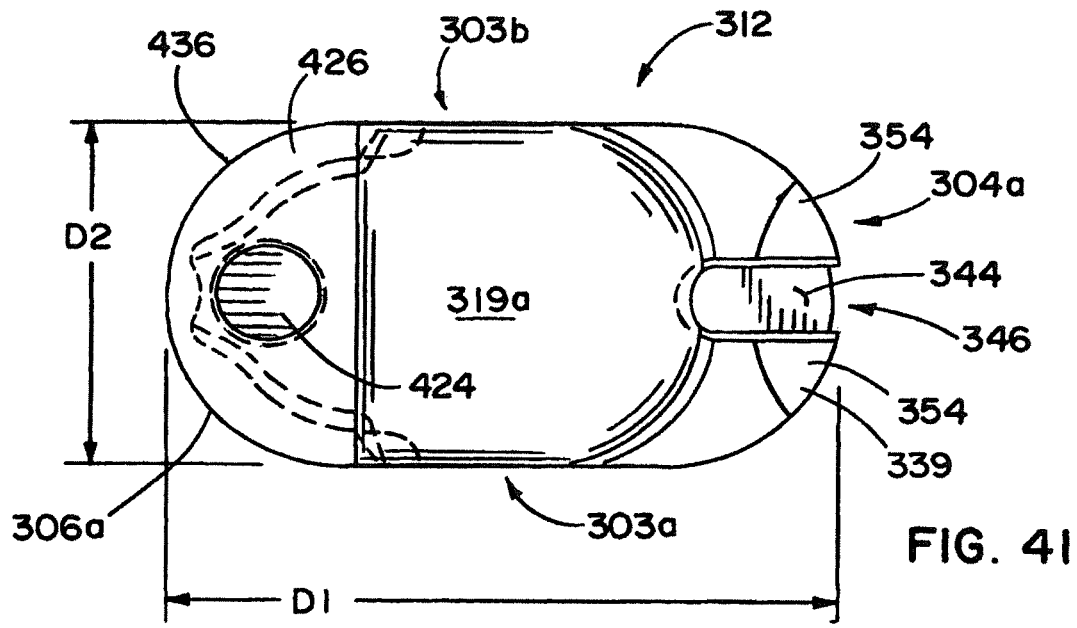
FIG. 41 is a top plan view of the lower member of the artificial disc device of FIGS. 35 and 36 showing a generally racetrack peripheral configuration and a recess at the leading edge of the lower member.
Figure 42:
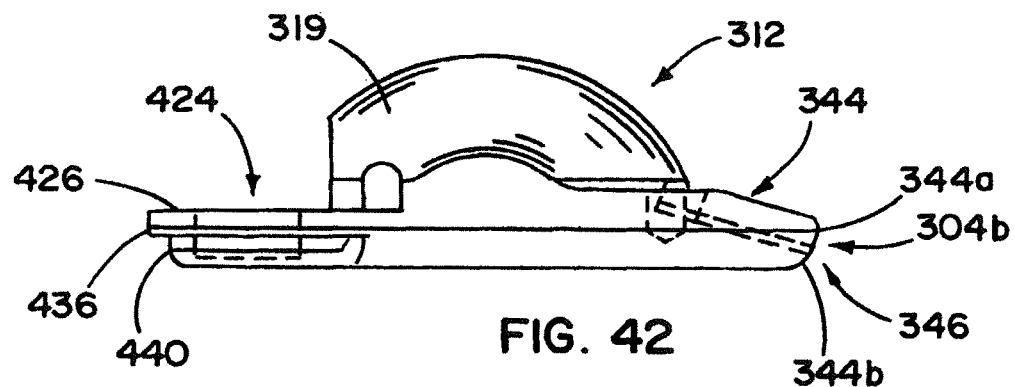
FIG. 42 is a side elevational view of the lower member showing a dome bearing portion thereof.
Figure 43:
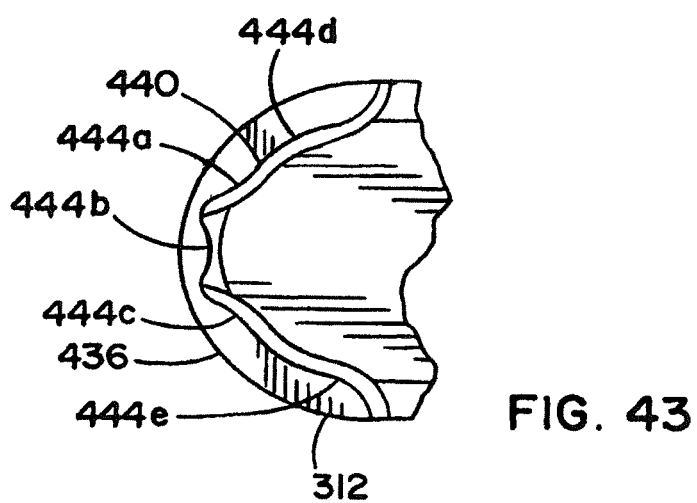
FIG. 43 is a fragmentary bottom plan view of the lower member showing the wall portion and wall for confronting the inserter tool during insertion.
Figure 44:
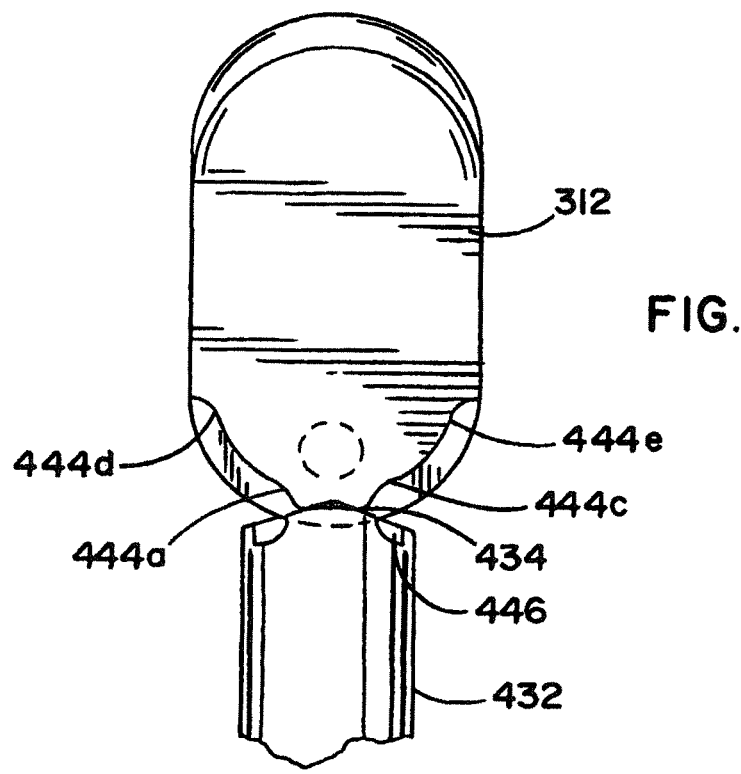
FIG. 44 is a bottom plan view of a grip member of the inserter tool secured to the lower member in the insertion orientation.
Figure 45:
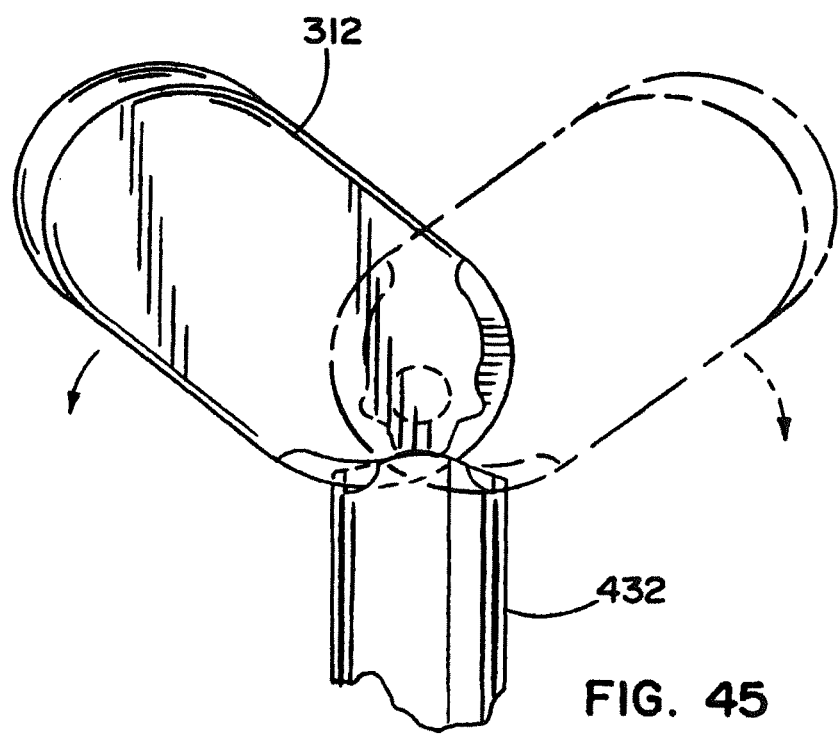
FIG. 45 is a bottom plan view of the grip member and lower member corresponding to FIG. 44 showing the lower member rotated relative to the grip member for positioning the lower member within the annulus.

Referring to FIGS. 41 and 42, it can be seen that the lower member 312 includes a recess 344 formed at the end 304a thereof with the recess 344 extending at an incline upwardly in a direction extending from the front end 304a toward the rear end 306a relative to the general plane of the disc member 312. A projection 342 that fits in the recess 344 is provided on the upper member 314, and it is configured to extend in or parallel to the general plane of the member 314. In this manner, with the disc members 312, 314 releasably attached via receipt of the projection 342 in the recess 344, the upper member 314 will be inclined or tilted upwardly relative to the plane of the lower member 312. Also, the bearing portions 317 and 319 cooperate so that the upper member 314 is engaged with and supported by the lower member 312 with the members 312, 314 releasably attached. In particular, rearward of the releasable connection 340 the recess bearing portion 317 of the upper member 314 will rest on the front side of the upper member bearing portion 319, as can be seen in FIG. 35.

The releasable connection 340 is of sufficient strength to keep the disc members 312, 314 attached together as the disc unit 300 is being pushed through the annulus incision 308 and for the initial stage of insertion into the vertebral disc space 311. As discussed, the shells 312, 314 are preferably provided with cooperating structure such as a projection 342 and recess 344 that releasably secures the shells 312, 314 in the desired wedge-angle orientation. In the preferred and illustrated form, the releasable connection 340 is in the form of an interference or snap-fit connection such as a dove-tail joint 340 located at the leading end portions 304a, 304b of the shells 312, 314. In this regard, the top shell 314 includes the projection in the form of a dove-tail projection 342, and the bottom shell 312 includes a mating recess 344 configured to substantially match the configuration of the dove-tail projection 342.

As described above for the previous embodiments, the leading and trailing ends 304a, 304b, 306a, 306b of the upper and lower members 312, 314 are provided with an extent that, when implanted, provides the desired maximum physiological movement between the implant members 312, 314. The leading ends 304a, 304b may also include abutment surfaces 352, 354 so that the members 312, 314 may contact and abut along surfaces 352, 354 when in the insertion configuration. The members 312, 314 may be oriented so that the surfaces 352, 354 are in flush contact when the projection 342 and recess 344 are secured or snap-fit together. Towards this end, the upper shell member 314 includes a flat surface 352 from which the dove-tail projection 342 extends that abuts the raised flat surfaces 354 on either side of the recess 344 of the bottom member 312. The flat surfaces 354 are inclined upward in a direction from the front, or leading edge, toward the rear of the lower member 312. As illustrated, the top member surface 352 is not inclined, and the wedge-angle ω may correspond to the angle provided between the surfaces 354, 352 by the inclination of the surfaces 354 of the lower member 312. However, the angle of the surfaces 354, 352 may be reversed such that the surface 352 is angled inwardly from respective leading edges 304a, 304b, or the angle of the surfaces 354, 352 may each be angled inwardly, each configuration being such that the surfaces 354, 352 may be in a flush abutting relationship at the wedge-angle ω.

To secure the dove-tail 342 in the recess 344, the shells 312, 314 may be placed together such that the recess 344 is positioned in a confronting relationship to the dove-tail projection 342. The dove-tail projection 342 includes wings 343 angled outwardly from a base 345 of the projection 342 such that the projection 342 has a leading surface 342a with a dimension D3 greater than a dimension D4 at the base 345. The recess 344 is provided with a geometry for receiving the angled wings 343 of the projection 342 such that an upper portion 344a of the recess 344 is smaller in dimension than a lower portion 344b. In this manner, manual pressure may then be applied to the top and bottom surfaces 320, 322 of the shells 312, 314 so that the wings 343 of the dove-tail 342 are forced into the recess 344 and secured there in a snap-fit or interference fit. Alternatively, the dove-tail 342 may be secured in the recess 344 simply by aligning the dove-tail 342 with an opening 346 at the forward end of the recess 344 and sliding the dove-tail projection 342 therein. At least a portion of the connection 340 is formed of material that is resiliently deformable such that either the projection 342, the surfaces about the recess 344, or both may resiliently deform to permit the projection 342 to be received with the recess 344 in the snap-fit or interference fit. In addition, the resiliently deformable material permits the connection 340 to be released during insertion due to the force of implantation and constraint of adjacent vertebrae, as will be discussed hereinafter. Surfaces of the projection 342 and recess 344 may be coated with a material that facilitates joining the projection 342 and recess to form the connection, and/or material that resists the separation of the connection 340 during implantation, as will be discussed below.

Figure 36:
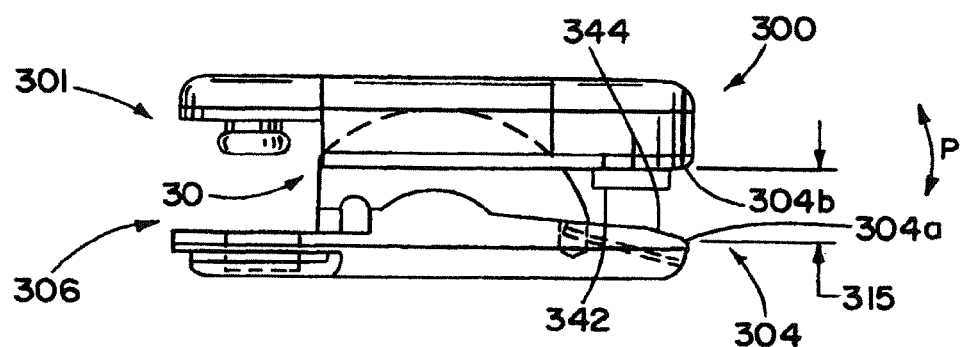
FIG. 36 is a side elevational view similar to FIG. 36 except with the connection between the members released with the members in an operable configuration.
Figure 37:
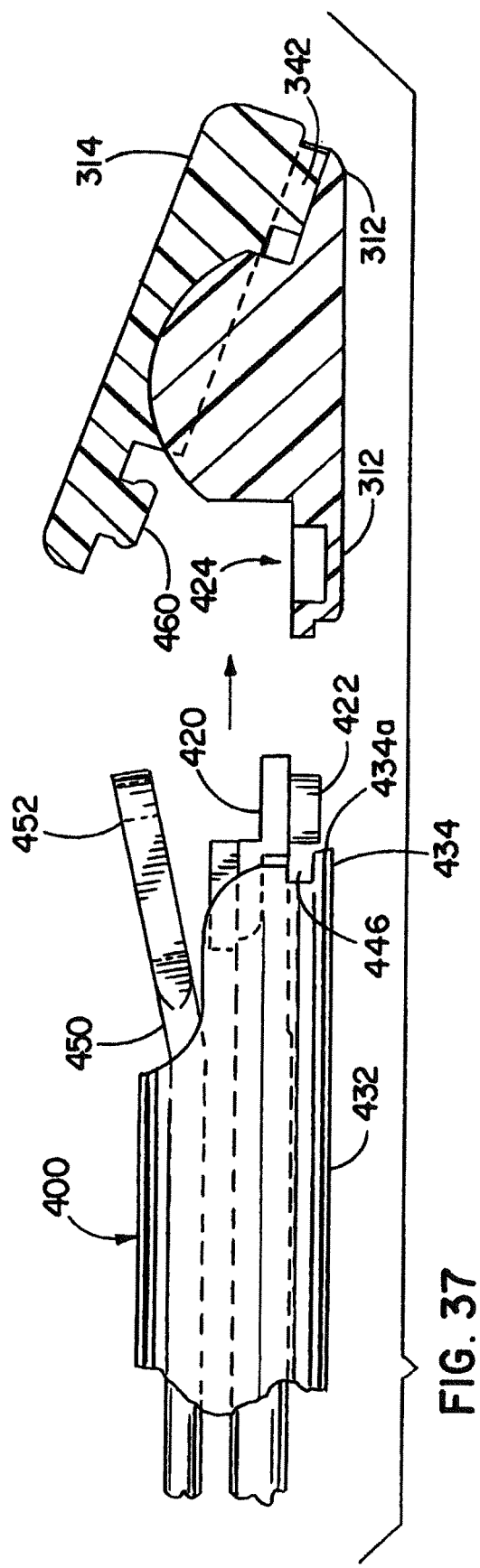
FIG. 37 is a partial cross-sectional view corresponding to FIG. 35 showing the members connected in the insertion configuration and an inserter tool for implanting the artificial disc device.
Figure 38:
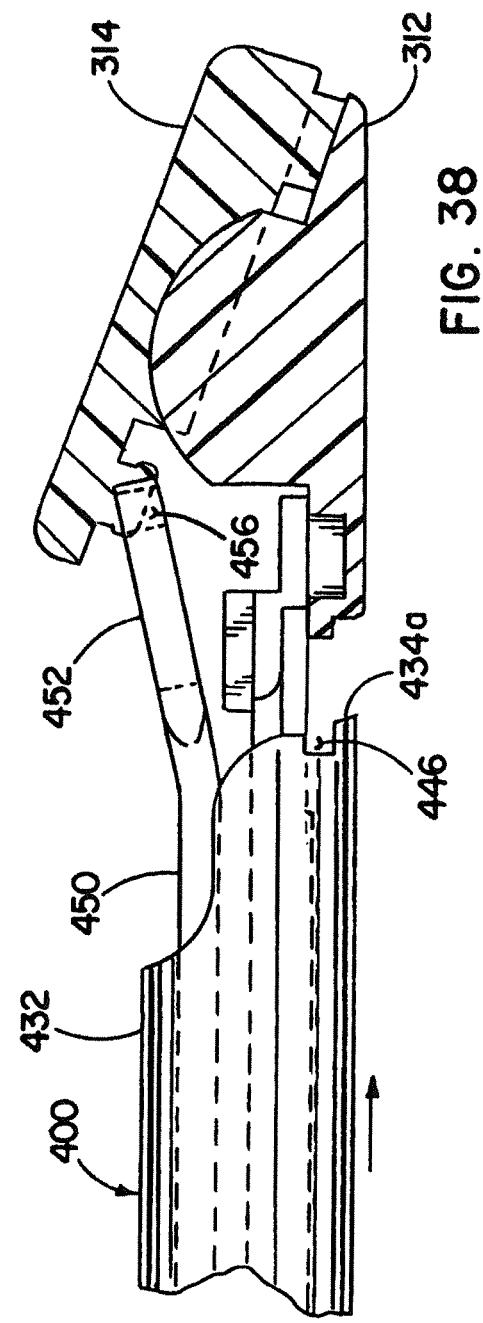
FIG. 38 is a partial cross-sectional view corresponding to FIG. 37 showing a grip member of the inserter tool extended relative to a grip shaft to grip the artificial disc device for implantation.
Figure 39:
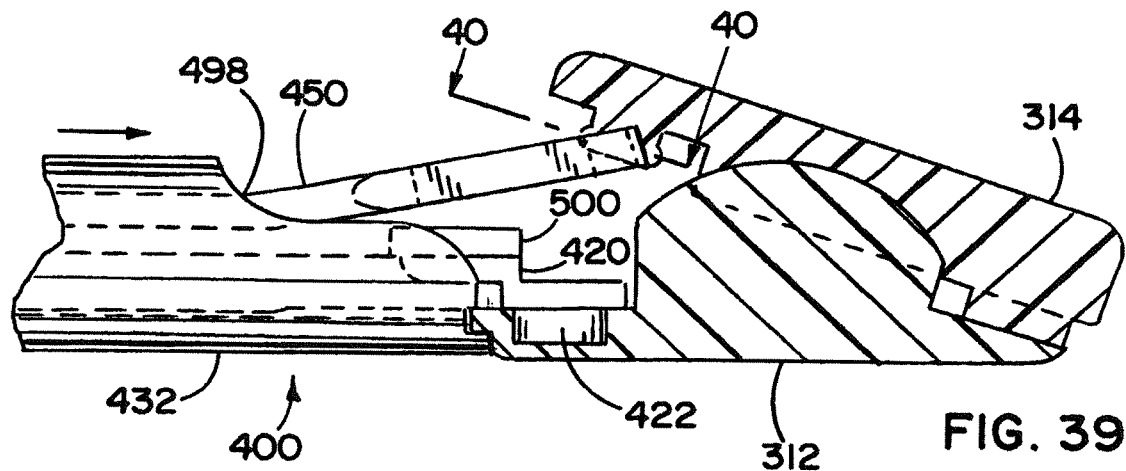
FIG. 39 is a partial cross-sectional view corresponding to FIG. 38 showing the inserter tool secured to the artificial disc device for implantation with the grip member advanced to hold the lower member.
Figure 40:
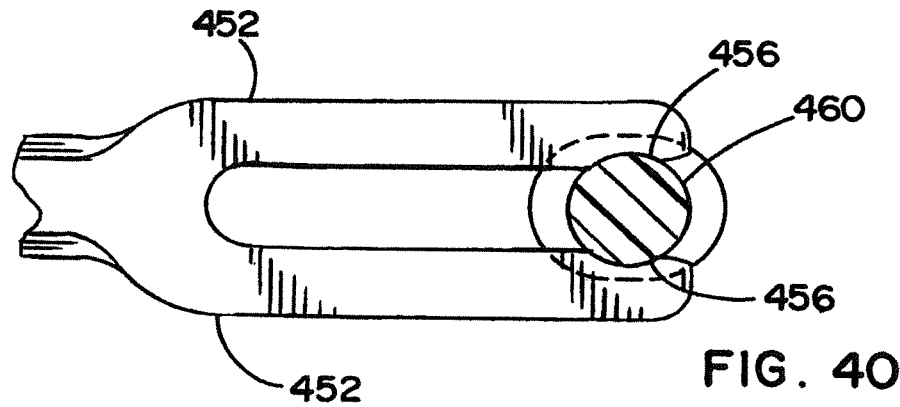
FIG. 40 is a partial cross-sectional view taken through the line 40-40 of FIG. 39 showing a grip post of the upper member secured in a yoke grip.
Figure 49:
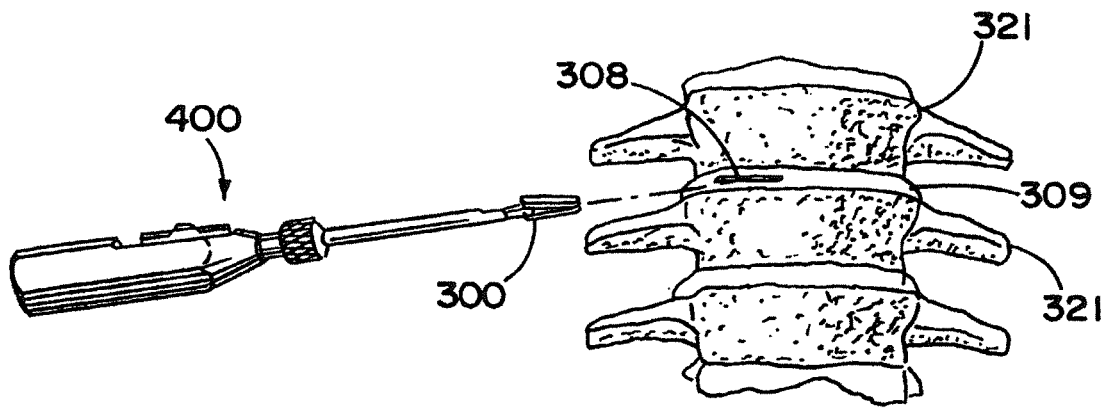
FIG. 49 is a view of the artificial disc device secured to the inserter tool in the insertion configuration and a spinal section including an annulus of a spinal disc having an incision made therein.

Accordingly, the interference fit provided between the connecting portions 342 and 344 provides a predetermined level of resistance against pivoting of the disc members 312, 314 relative to each other and, in particular, the upper member 314 at the forward end 304b thereof away from the lower member forward end 304a. On the other hand, with sufficient force applied to members 312, 314, the interference fit of the dove-tail connection 340 is overcome so that the disc members 312, 314 can assume an operable configuration where the members 312, 314 can shift relative to each other, as shown in FIG. 36. To this end, the disc device 300 is selected relative to the size of the vertebral or nuclear space into which it is to be inserted. The distance between the trailing or rearward end portions 306a and 306b of the respective members 312, 314 in their attached insertion configuration should be slightly greater than the distance between the adjacent vertebrae 321, and specifically the end plates 313 thereof between which the disc device 300 is to be inserted.

Thus, as the disc device or unit 300 slides into the space as described further hereafter, the lower and upper trailing ends 306a, 306b will be brought into engagement with the corresponding end plates 313. Accordingly, in the preferred form herein, it is the top and bottom surfaces 322, 320 that serve as engagement portions of the disc body 301 during the implantation procedure. Continued pushing of the disc unit 300 into the vertebral disc space 311 causes the surfaces 322, 320 to engage or cam initially against the annulus, which becomes compressed, and then against the vertebrae and end plates 313 with progressively greater force. With a properly sized disc unit 300 relative to the vertebral disc space 311, this squeezing force at the opposing, spaced apart ends 306a, 306b eventually will become great enough to cause the releasable connection 340 to snap apart so that the members 312, 314 pivot relative to each other about the bearing interface 315 therebetween. With the connection 340 formed at the leading end portion 304 of the disc assembly 300, and the separation force applied on the top and bottom surfaces 322, 320 thereof, there is a lever arm advantage that is utilized to overcome the interference fit at the preferred connection 340 with the intermediate dome bearing portion 319 serving as a fulcrum for this purpose. This allows the strength of the attachment between the members 312, 314 as provided by the connection 340 to be maximized to ensure that the disc unit 300 maintains its connected insertion configuration during insertion until it is inserted into the annulus 309 a sufficient amount. On the other hand, it is also true that this wedge arrangement and utilizing the members as lever arms 312, 314 allows for relatively low force insertion of the disc assembly 300 into the vertebral disc space 311 and to achieve the operable configuration of the disc assembly 300. In addition, the small configuration of the leading end allows the assembly 300 to be easily aligned with the incision for initial insertion. Moreover, the separation force can be applied to the ends 306a and 306b as the disc unit 300 is being turned or rotated, as previously described, toward its fully seated position between the vertebrae in the nuclear space therebetween. In shifting between the insertion configuration and the operable configuration, the members 312, 314 have a pivoting direction, as represented by arrow P in FIGS. 35 and 36.

Figure 53:
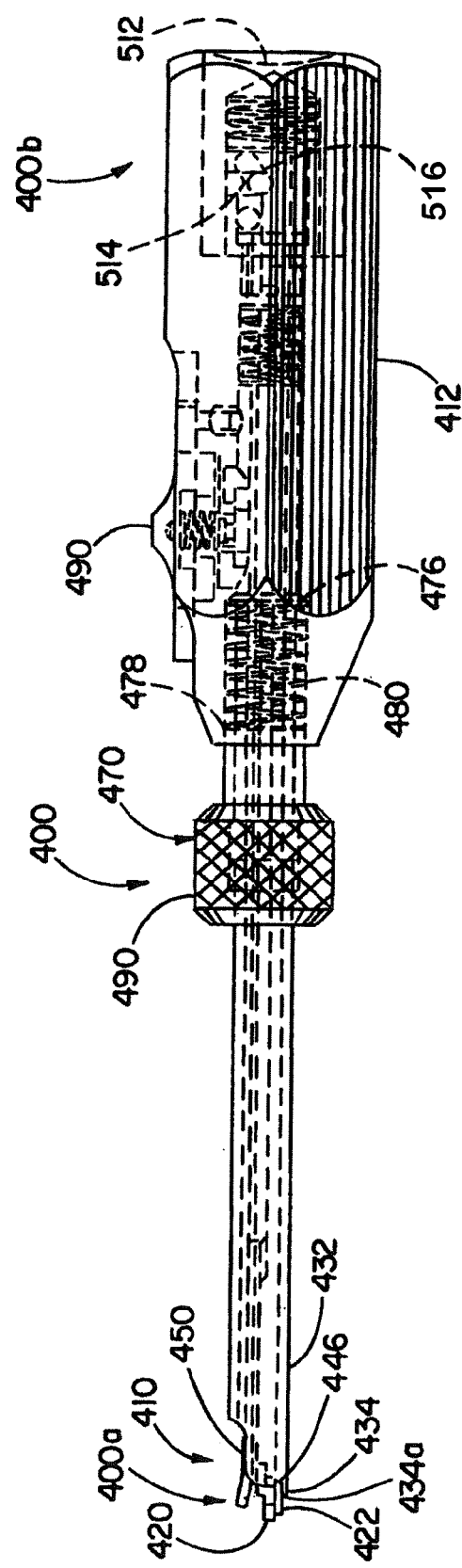
FIG. 53 is a side elevational view of the inserter tool in accordance with the present invention.
Figure 54:
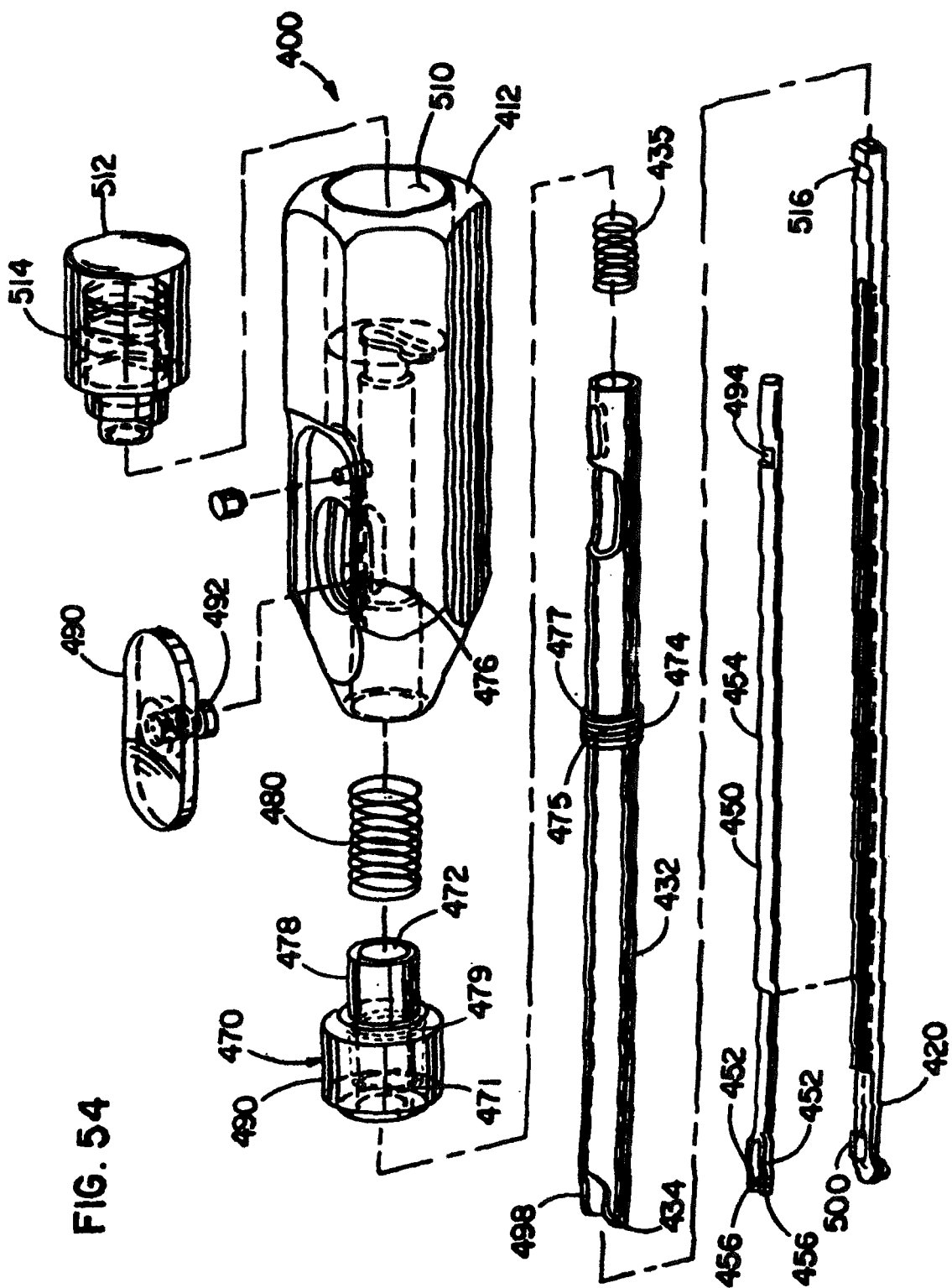
FIG. 54 is an exploded perspective view of the inserter tool of FIG. 53 showing grip members for securing the inserter tool to the artificial disc device.

An inserter instrument 400 for implanting an artificial disc device such as implant 300 is illustrated in FIGS. 53 and 54. The inserter 400 may grip or releasably secure the shells 312, 314 of the implant 300 for insertion and rotation into and within the nuclear cavity 311.

In order to initially grip the shells 312, 314, the inserter 400 is provided with grip members 410 for retaining the shells 312, 314 on a distal end 400a of the inserter 400 while a surgeon, for instance, holds a handle 412 on a proximal end 400b. A first grip member in the form of an elongate, rod-like base grip 420 is generally fixed relative to the handle 412 and includes structure in the form of a boss 422 extending from the grip member 420, and the bottom shell 312 has engaging structure in the form of a recess 424 formed in a surface 426 thereof. The recess 424 is formed proximal a trailing end 306a of the bottom shell 312. The surface 426 is generally oriented towards and facing the top shell 314 when the implant 300 is assembled. Therefore, the boss 422 extends in a direction generally away from the top shell 314 when attached to the bottom shell 312.

The inserter 400 is further provided with a second grip member which may selectively reciprocate in a direction parallel with the base grip 420. Specifically, the second grip member is in the form of a cylindrical grip shaft 432 generally surrounding the base grip 420, and the grip shaft 432 is biased towards the distal end 400a of the inserter 400 by, for instance, a spring 435. The grip shaft 432 includes a contoured tip 434 for contacting the trailing end 306a of the bottom shell 312.

More specifically, the trailing end 306a of the bottom shell 312 includes a wall portion 436 extending from the bottom shell 312. The wall portion 436 forms a shoulder 440 at its base with the bottom shell 312 near the trailing end 306a. The shoulder 440 is scalloped to define a continuous surface including sequential, arcuate surfaces 444. A middle arcuate surface 444b is aligned with the longitudinal dimension D1 of the shell 312. The grip shaft tip 434 is contoured to provide a surface 434a that matches the curve of the middle arcuate surface 444b. Accordingly, the shaft tip 434 and the middle arcuate surface 444b mate in a pre-determined orientation.

To the sides of the middle arcuate surface 444b are side arcuate surfaces in the form of secondary arcuate surfaces 444a, 444c, which are generally identically curved to each other and are angled outward from the middle arcuate surface 444b, and of tertiary arcuate surfaces 444d, 444e which are also generally identically curved and are angled outward from the secondary arcuate surfaces 444a, 444c. As an example, the total angle between the middle arcuate surface 44b and the left side arcuate surfaces 444a, 444c, or right side arcuate surfaces 444d, 444e may be approximately 90-95°. However, the side arcuate surfaces 444a, 444c, 444d, 444e do not require a precise orientation for the shaft tip 434. In this manner, when the shaft tip 434 is against any side arcuate surface 444a, 444c, 444d, 444e, the bottom shell 312 may shift in orientation against the side surface 444a, 444c, 444d, 444e. The grip shaft 432 further includes a shell recess 446 located near the shaft tip 434 and in between the shaft tip 434 and the base grip 420 positioned within the grip shaft 432.

The bottom shell 312 is secured to the inserter 400 by the grip shaft 432 and the base grip 420. To do so, the grip shaft 432 is partially retracted against the spring bias so that the shaft tip 434 is moved a distance away from the boss 422. The boss 422 is then inserted into recess 424 of the bottom shell 312, and the wall portion 436 is inserted into the shell recess 446. The grip shaft 432 is then allowed to shift towards the bottom shell 312 such that the shaft tip 434 mates with the middle arcuate surface trial spacer. In this manner, the bottom shell 312 is clamped by the bias force of the grip shaft 432, and its longitudinal dimension is aligned with the elongate base grip 420 and grip shaft 432.

In the preferred embodiment, the grip shaft 432 may be mechanically tightened or secured so that accidental refraction against the bias does not occur. In the present embodiment, this is achieved by including a biased-forward securement sleeve 470 having an internal bore 472 such that the securement sleeve 470 is positioned around the grip shaft 432, as well as partially within the handle 412. The grip shaft 432 has a widened portion 474 having external threads 475 forming a shoulder 477, while the securement sleeve 470 has a butt shoulder 478 at its proximal end, a shoulder 479 within its internal bore 472, and threads 471 within the bore 472. A spring 480 is located between the butt shoulder 478 and a shoulder 476 formed in the handle 412, while the shoulders 477, 479 are generally in contact by force of the spring 480. Therefore, retraction of the grip shaft 432 causes its shoulder 477 to press against the shoulder 479 of the securement sleeve 470 so that both retract together.

However, the securement sleeve 470 may retract relative to the grip shaft 432 by compressing the spring 480, as well as may rotate independent of and relative to the grip shaft 432. More specifically, the securement sleeve threads 471 mate with the grip shaft threads 475. In a normal position, the spring 480 biases the securement sleeve threads 471 away from the grip shaft threads 475. When the securement sleeve 470 is retracted against the spring 480, the securement sleeve threads 471 move to a position where they may engage the grip shaft threads 475. The securement sleeve 470 may be rotated by a knurled knob 490 so that the securement sleeve is threaded onto the grip shaft 432. Eventually, the knob 490 comes into contact with the handle 412 such that the securement sleeve 470 is tightened thereagainst, along with the grip shaft 432 threaded into the securement sleeve 470. In this manner, the grip shaft 432 is unable to retract, and the bottom shell 312 is locked between the secured grip shaft 432 and the fixed base grip 420.

The inserter 400 may also secure the top shell 314 for insertion. To do so, the inserter 400 includes a third grip member in the form of a yoke grip 450, and the top shell 314 is provided with a grip post 460 received by the yoke grip 450. The yoke grip 450 includes an elongate shaft 454 also generally positioned within the grip shaft 432, and a pair of yoke arms 452 at a distal end 450a. Each yoke arm 452 includes a cup- or hemispherical-shaped recess 456 on an interior surface such that the cup recesses 456 of the respective yoke arms 452 are generally oriented toward and facing each other.

The grip post 460 of the top shell 314 includes an exterior surface 462 for engaging within the cup recesses 456. To insert the grip post 460 within the yoke arms 452, the yoke arms 452 may flex outwardly slightly, as well as the grip post 460 may compress slightly. In this manner, the grip post 460 is snap or interference fit within the yoke arms 452 and releasably secured therein. Unlike the securement of the bottom shell 312, which has a rigid orientation with the inserter 400 in the initial position, the top shell 314 is allowed to pivot around its grip post 460 within the yoke arms 452, such as like a ball joint.

It should be noted that the shells 312, 314 may be secured to form the dove-tail joint 340 prior to being secured to the inserter 400. Alternatively, the shells 312, 314 may be provided with the insertion orientation after being secured to the inserter 400. For this, as the top shell 314 is pivotable, manual pressure is simply applied to force the dove-tail 342 and recess 344 together. As an additional alternative, the inserter 400 may secure to the top shell 314 such that the top surface 322 is provided with a specific angle, and the shells 312, 314 then are provided with the wedge-angle ω and the insertion configuration.

Once releasably secured to the inserter 400 and in the insertion configuration, the implant 300 is ready to be inserted into and through the annulus 309 and into the nuclear cavity 311. As discussed above, the force of insertion experience by the implant 300 causes the implant 300 to shift from the insertion configuration to the operable configuration. As also noted, the inserter 400 may be used to rotate the implant 300 to orient and align the larger, longitudinal dimension D1 with the incision 308 in the annulus 309. During insertion and rotation, the implant 300 may contact an inner surface 309a of the annulus such that the contact guides the implant 300 into the nuclear cavity 311 and guides the rotation of the implant 300 therewithin. It should be noted that the implant 300 and inserter 400 may be used in a variety of surgical approaches or techniques, including those from a direction other than posterior. For instance, in a lateral incision direction, the manipulation and cooperation of the inserter 400 and implant 300 would not require the same adjustments as those required for the posterior approach.

Once the implant 300 has shifted to the operable configuration, the top shell 314 is generally not free to move. That is, despite being secured to the inserter 400 by a ball joint type securement in the form of the grip post 460 and yoke arms 452, the top shell 314 is constrained from significant movement by the annulus 309 and vertebral endplates 313, as well as the articulating bearing member 30 formed between the shells 312, 314. Accordingly, the top shell 314 generally follows the bottom shell 312.

The bottom shell 312 remains generally fixed relative to the inserter 400 until the surgeon selects otherwise. When a determination is made that the implant 300 has been advanced within the annulus 309 and nuclear cavity 311a sufficient amount that the rigidity is no longer necessary, or that the implant is in a position that it needs to be rotated, the grip shaft 432 may permit the bottom shell 312 to shift or pivot around the boss 422 to one of the side arcuate surfaces 444a, 444c, 444d, 444e. The bias of the grip shaft 432 may then shift the grip shaft 432 into an abutting relationship with one of the 444a, 444c, 444d, 444e. Accordingly, the top shell 314 also pivots with the bottom shell 312 around the grip post 460. As the side arcuate surfaces 444a, 444c, 444d, 444e are angled from the middle arcuate surface 444b, the surgeon may direct the implant 300 into the nuclear cavity 311 in the lateral direction (orthogonal to the anterior-posterior direction) when the shaft tip 434 is secured in one of the side arcuate surfaces 444a, 444c, 444d, 444e.

It should be noted that, once the implant 300 is inserted sufficiently into the incision, the grip shaft 432 may be completely retracted. Because of the pressure and constraint provided by the superior and inferior endplates 313, coupled with the yoke arms 452 and the grip shaft boss 422, the bottom and top shells 312, 314 are generally unable to escape, though they are able to pivot. In this manner, the surgeon may pivot and manipulate the implant 300 within the nuclear cavity 311, for instance, until a desired position is achieved while the grip shaft 432 is still biased by the spring in a confronting relationship with the surfaces 444.

To withdraw the inserter 400, the implant 300 must be released therefrom. In the preferred embodiment, the yoke grip 450 is selectively reciprocable by a slide 490. To secure the top shell 314 thereto, the yoke grip 450 is advanced relative to the grip shaft 432 by advancing the slide 490 relative to the handle 412. The slide 490 includes a post 492 received within a recess 494 in the yoke grip shaft 454 within the handle 412. To release the implant 300, the top shell 314 is released by retracting the slide 490, thereby retracting the yoke grip 450. As the shell members 312, 314 are mated, such retraction should allow the yoke arms 452 to separate from the top shell 314. Alternatively, such retraction may draw the yoke arms 452 towards and within the cylindrical grip shaft 432 such that a trailing end 306b of the top shell 314 contacts an edge 498 of the grip shaft 432. Continued retraction of the yoke grip 450 forces the top shell 314 to be released from the yoke arms 452. As a further alternative, retraction of the yoke grip 450 may force the top shell 314 against a portion, such as post 500, of the base grip 420, thereby causing the top shell 314 to be released from the yoke arms 452. The grip shaft 432 may then be retracted, and the boss 422 may be lifted out of the recess 424.

The proximal end 400b of the handle 412 includes an opening 510 in which a release 512 is secured and spring-biased in the proximal direction. When the bias is overcome and the release 512 is pushed into the handle 412, a pin 514 is shifted from a secure position to a release position. In the secure position, the pin 514 is received in a recess 516 of and secures the base grip 420 in a generally fixed position. In the release position, with the pin 514 shifted out of the recess 516, the base grip 420 may be removed, as well as the yoke grip 450 and the slide 490. In this manner, the inserter 400 may be disassembled for cleaning and sterilization post-procedure.

Referring now to FIG. 55, a further embodiment of an implant 600 is depicted having a bottom shell 612 and a top shell 614 forming an articulating bearing member 30. The top shell 614 has a recess 616 for receiving and articulating with a dome 618 on a spacer 620. The spacer 620 is secured in a stepped recess 630 such that the spacer 620 may move a slight amount within the stepped recess 630. More specifically, the spacer 620 has a depending post 622 with a lower flange 624 for securing in a lowermost recess portion 632 of the stepped recess 630. The spacer 620 has a intermediate post portion 626 connecting the lower flange 624 to the dome 618. The intermediate post portion 626 is located within, and slightly smaller than, a intermediate recess portion 634 of the stepped recess 630. The dome 618 includes a bottom surface 640 that forms a shoulder 642 with the intermediate post portion 626. The stepped recess 630 includes an upper recess portion 636 within which a low friction washer or bushing 638 is located for friction reduction. That is, the bushing 638 has a top surface 638a that abuts against the bottom surface 640 of the dome 618, and a bottom surface 638b that abuts a top surface 636a of the bottom shell 612 in the upper recess portion 636. The bushing 638 may be polymeric and, for instance, polyurethane.

With further reference to FIG. 35, an alternative releasable connection is shown in phantom as a band 333 connected to the upper member 314 and lower member 312 at the insertion end of the implant 300. The band 333 retains the members 312, 314 in the insertion configuration during initial insertion to provide the wedge angle ω, as discussed above. As force increases that acts on the members 312, 314 due to insertion against the spinal material such as the annulus or vertebrae, tension is increased on the band 333 until the band 333 is broken or otherwise disconnect from one of the members 312, 314, thus allowing the members 312, 314 to shift to the operable configuration. Furthermore, the band 333 may be a bioabsorable material such that, after a period of time, the band 333 is absorbed.

Figure 46:
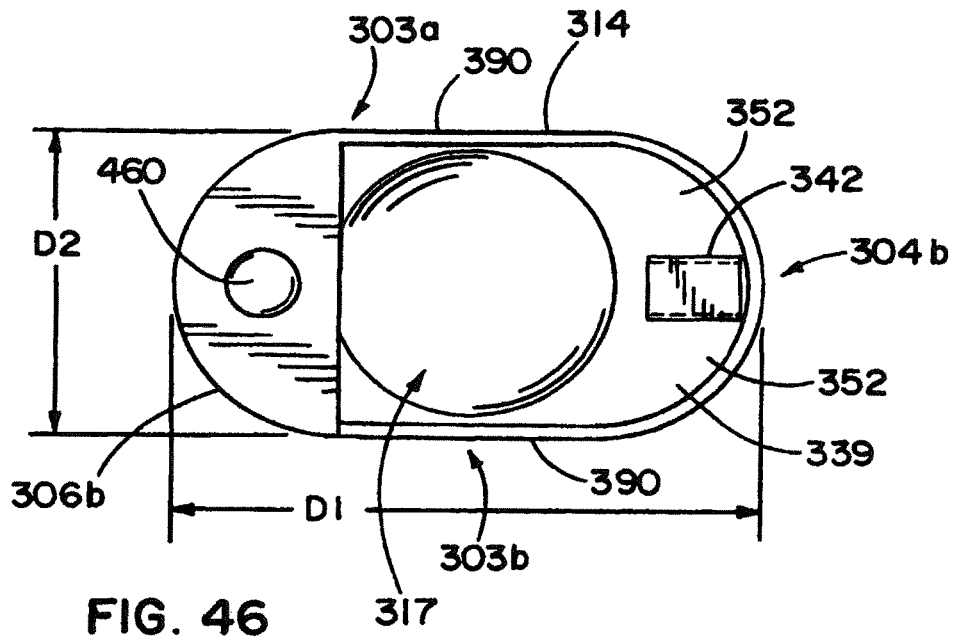
FIG. 46 is a top plan view of the upper member of the artificial disc device of FIGS. 35 and 36 showing a generally racetrack peripheral configuration and a projection at the leading end of the upper member.

With continued reference to FIG. 35, as well as FIGS. 41 and 46, a further releasable connection is shown as a chemical bond 339. The chemical bond 339 may be placed on the flat surface 352 of the upper shell member 314, on the flat surfaces 354 on either side of the recess 344 of the bottom member 312, or both. As stated, the releasable connection of the chemical bond 339 holds the members 312, 314 in position during initial insertion until the bond 339 is broken, thereby allowing the members 312, 314 to shift to the operable configuration. The chemical bond 339 may also be bioabsorbable or biocompatible.

FIG. 56 depicts a further embodiment of an implant 650 in an insertion configuration and having a bottom shell 660 and top shell 662 forming an articulating bearing member 30. Similarly to the implant 300, the implant 650 has a pivoting direction P. Cooperating structure is provided such that the implant has an insertion configuration. The cooperation structure includes a hook 670 on a leading end 672 of the top shell 662 and a prong 674 on a leading end 676 of the bottom shell 660. In this embodiment, the force applied to the shells 660, 662 during insertion causes the hook 670 to release from the prong 674, thereby allowing the shells 660, 662 to pivot in the pivot direction P and to re-orient to an operable position.

Referring to FIGS. 57-60, an implant 700 is depicted having a bottom shell 712 and top shell 714 forming a butt-joint with an interference fit. The bottom shell 712 has a leading end 712a and has a recess 720 proximately located to the leading end 712a. The recess 720 is angled downward so that it increases in depth towards the leading end 712a and forms an angled surface 722 therein. At an outer periphery 724 of the recess 720 and near a top surface 726 of the bottom shell 712, a lip 728 is formed. The top shell 714 includes a surface 740 that tapers upward towards a leading end 714a. Extending from the surface 740 is a tongue 742 with a lip 744 around an outer periphery 746 of the tongue 742. The tongue 742 of the top shell 714 is received within the recess 720 such that the lip 744 of the top shell 714 is confronted by the lip 728 of the bottom shell 712. The confronting lips 744, 728 form an interference fit, thereby holding the implant 700 in the insertion configuration. When sufficient insertion force is experienced by the implant 700, the lips 744, 728 release from each other so that the shells pivot in the pivoting direction P and may re-orient themselves to the operable configuration.

Figure 69:
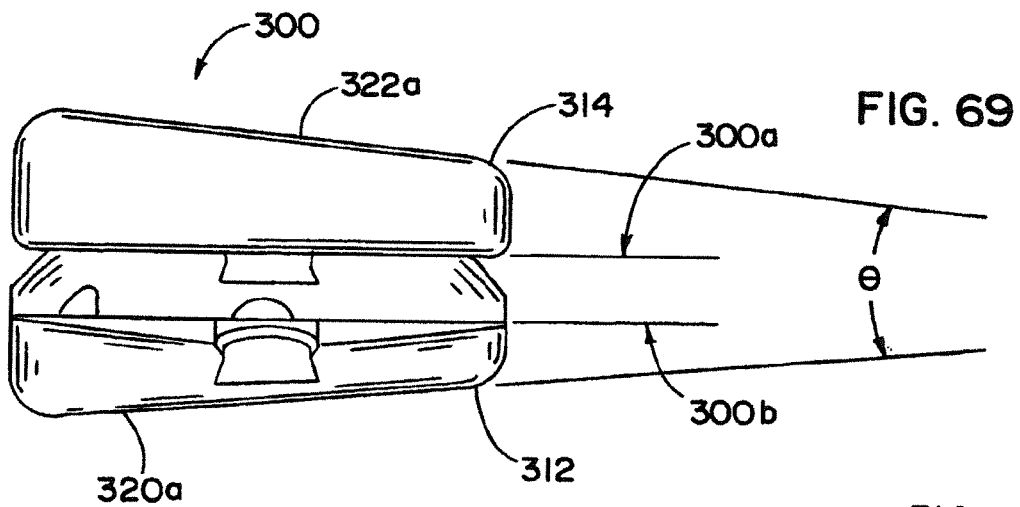
FIG. 69 is a side elevational view of a trailing end of an artificial disc device have an operable lordotic angle.
Figure 70:
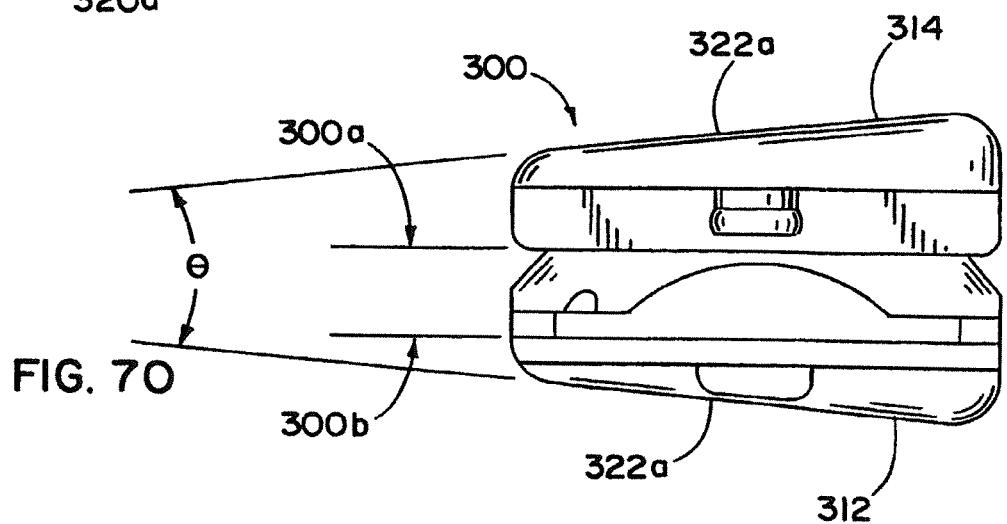
FIG. 70 is a side elevational view of an insertion end of the artificial disc device of FIG. 61 showing the operable lordotic angle.
Figure 71:
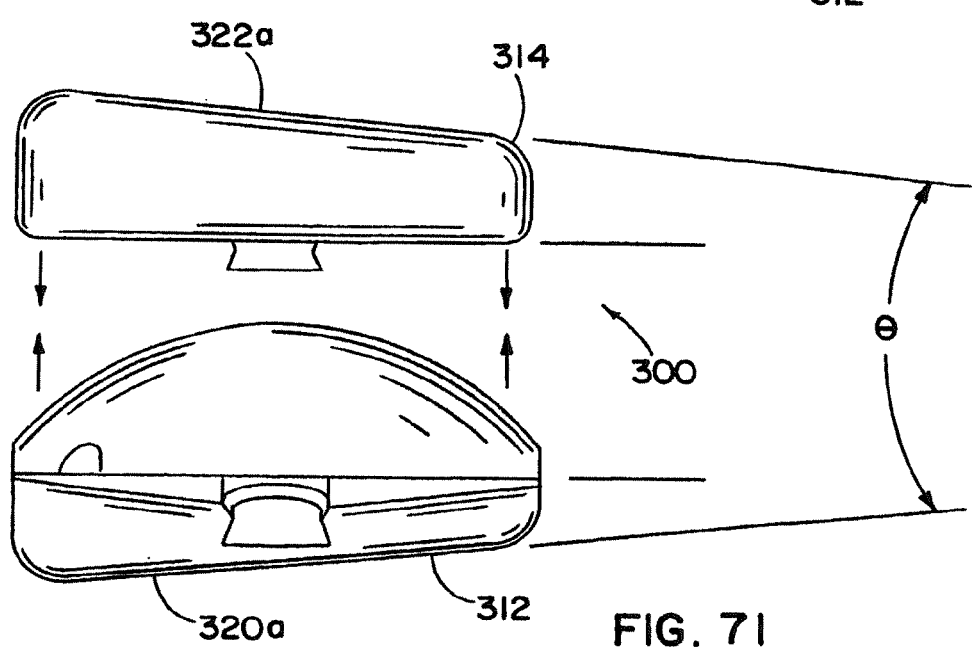
FIG. 71 is an exploded view of the artificial disc device of FIG. 69 showing upper and lower members.

In embodiments of the present invention, various implants may be provided and selected from during a surgical procedure. The implants may vary by size depending on the size of the nuclear cavity. Additionally, the vertebral endplates between which the implant is to be located may be other than generally parallel to each other. Accordingly, once implanted and rotated, the implant 300 may be provided with a similar configuration in the operable configuration to provide for the natural curvature of the adjacent vertebrae. As such the operable configuration provides implant top and bottom surfaces 322a, 320a with an operable angle θ corresponding to the angle of the endplates of the adjacent vertebrae. As can be seen in FIGS. 69-71, the operable angle θ is the angle measured between the operable configuration top and bottom surfaces 322a, 320a measured in the anterior-posterior direction.

In FIGS. 69 and 70, the implant members 312, 314 of the implant unit 300 have respective general planes 300a, 300b, described earlier as being defined by the longitudinal and lateral axes of the implant members 312, 314. As can be seen, the planes 300a, 300b are generally parallel in the operable configuration. The operable angle θ is formed by the top and bottom surfaces 322a, 320a when the planes 300a, 300b are generally parallel. Several different sizes of artificial disc units 300 will be provided which will vary based on the size of the implant members 312 and 314 including the operable angle θ therebetween. For instance, the implants 300 may be provided with operable angles θ of zero, 6 or 12 degrees.

In order to select the proper size and operable angle θ, the implant site is examined. For this, a trial spacer instrument 800 may be provided, as illustrated in FIGS. 61 and 62. The trial spacer instrument 800 is utilized with a series of trial spacers, a representative trial spacer 850 being depicted in FIGS. 63 and 64. As depicted, the trial spacer 850 has an operable angle θ of zero, though it is preferably provided with an operable angle θ of zero, 6, or 12 degrees, for instance, so that it can be matched with the proper implant 300.

The trial spacer instrument 800 includes an elongate handle 810 with a brace 812 located on one side thereof. The brace 812 preferably includes two arms 814, each including a bore 816 aligned in the length-wise direction of the handle 810. Between the arms 814 is a nut 818 separated from the arms 814 by low friction washers (not shown). The nut 818 includes a central, internally threaded bore 820 aligned with the bores 816 of the arms 814. A screw 824 is located within the bores 816, 820 and includes threads mating with the threads of the nut bore 820. The nut 818 is positioned between the two arms 814 so that it is generally stationary, though it is free to rotate therebetween. As the nut 818 is rotated relative, the screw 824 located within the nut bore 820 is shifted axially relative to the arms 814, and to the handle 810.

To permit this, the screw 824 has a distal end non-rotatably connected to a slide arm 828. Therefore, the nut 818 may be rotated clockwise relative to the screw 824 to advance the screw 824, and the nut 818 may be counter-rotated to retract the screw 824. As the slide arm 828 is connected to the screw 824, it is advanced or retracted along with the screw 824. The slide arm 828 is aligned with and rests adjacent to a rail arm 830 fixed to the handle 810. In this manner, the screw 824 may be advanced or retracted to advance or retract the rail arm 830 relative to the rail arm 830 in the same direction.

The trial spacer 850 is secured to a distal end 800a of the trial spacer instrument 800. More specifically, the trial spacer 850 includes a trial spacer body 852, a instrument port 854, and a securing pin 856. The instrument port 854 is a recess flanked by top and bottom walls 860 and a rear wall 862. The pin 856 is passed through each of the top and bottom walls 860 and through the instrument port 854 recess. The instrument port 854 receives the distal end 800a of the trial spacer instrument 800 so that the trial spacer 850 is generally secured thereto.

The slide arm 828 and rail arm 830 each have respective distal ends 828a, 830a. The rail arm distal end 830a includes a barb or hook 840. When the slide arm 828 is retracted a sufficient distance, the hook 840 is exposed so that the pin 856 may be located therein. The slide arm 828 may then be advanced to that its distal end 828 passes over and beyond the hook 840. In this manner, the pin 856 located therein is captured and generally prevented from escaping the hook 840. Furthermore, the slide arm 828 may be advanced so that a terminal surface 828b of the distal end 828a abuts an interior wall 861 within the instrument port 854. In such a position, the mating surface 828b and interior wall 861 are generally prevented from moving relative to each other such that the trial spacer 850 is generally locked in a particular orientation to the trial spacer instrument 800. When the slide arm 828 is retracted a predetermined amount from the locked position, the trial spacer 850 may be rotated as desirable for insertion into the nuclear space. When the slide arm 828 is retracted further, the pin 856 may be released from the hook 840, and the trial spacer instrument 800 may be removed.

The trial spacer 850 is generally fashioned to provide ease of insertion through the incision to determine the size of the nuclear cavity. The trial spacer 850 may have a leading end 870 that is flat, or that is tapered to ease with insertion. The trial spacer 850 may also be shaped such that a desired operable angle θ may be determined. The edges of the trial spacer 850 may be radiused or smoothed to promote insertion and manipulation. Multiple trial spacers 850 of varying dimensional size may be sequentially attached to the distal end 800a of the trial spacer instrument 800 and inserted within the incision in order to determine the proper size and operable angle θ for the implant that is to be used in the operation. Alternatively, the leading end 870 may not be tapered.

The handle 810 of the trial spacer instrument 800 may include structure allowing an additional tool to be utilized in insertion of the trial spacer instrument 800. More specifically, as illustrated in FIGS. 65 and 66, an alternative trial spacer instrument 900 may include a driving or tapping mechanism 910 for providing a controlled strike directly through the central, longitudinal axis of the instrument 900 for communication to the trial spacer 850. In the present embodiment, the tapping mechanism is in the form of a mass 910 located at a proximal end 900a of the instrument 900 slidingly received and supported by a mass support in the form of a cylindrical slide 922 connected at a first end 922a to a handle 920. Accordingly, the mass 910 may be positioned away from the handle 920 and then directed towards the handle 920 along the slide 922 to strike the handle 920. The momentum of the mass 910 is communicated to the handle 920 to direct the trial spacer 850 into and through the annulus and into the nuclear space. The mass 910 may be accelerated towards the handle 920 by the surgeon, or by its own weight. A stub 915 is located on a second end 922b of the slide 922 to define the extent that the mass 910 may be positioned away from the handle 920, and to retain the mass 910 on the instrument 900. Thus, the operation of the tapping mechanism 910 enables a more controlled force to be communicated to the trial spacer 850 than manual force, and serves to retard the possibility that the trial spacer 850 will be pushed too hard or too far by the surgeon.

The trial spacer instrument 900 further includes an alternative advancement mechanism. The trial spacer instrument 900 has a slide arm 928 and a rail arm 930, similar to those described above for the trial spacer instrument 800. The slide arm 928 and rail arm 930 are slidingly secured to each other by a projection 932 extending from the slide arm 928 and received by a slot 934 in the rail arm 930. The projection 932 is permitted to reciprocate within the slot 934 while also guiding the slide arm 928 and rail arm 930 in a linear translation. The slide arm 928 further includes a bracket 940 extending from sides 942 of the slide arm 928 and generally forming a C-shape with bracket arms 944 wrapping around sides 946 and bottom 948 of rail guides 949 formed on the rail arm 930. In addition, a capture bracket 950 is located at a more distal portion of the slide arm 928, the capture bracket 950 also extending from sides 952 of the slide arm 928 and generally forming a C-shape with capture arms 954 wrapping around the side portions 930a and bottom 930b of the rail arm 930. The bracket 940 further serves to attach and slidingly secure the rail arm 930 with the slide arm 928. The slide arm 928 and rail arm 930 linearly translate relative to each other such that the slide arm 928 may be retracted to a position such that the trial spacer 850 may be received by a hook 840 and may be extended to capture the trial spacer 850 therein, as has been described above.

In the illustrated embodiment, the trial spacer instrument 900 is provided with selectable, discrete positions. More specifically, the slide arm 928 may be slid relative to the rail arm 930 to and between predetermined discrete positions. The rail arm 930 includes a port 960 generally opening to and facing the slide arm 928. The port 960 includes a spring-biased member that is, in the illustrated embodiment, post 962, though it may be a ball or other structure. The post 962 is bias-forced against a surface 964 on the rail arm 930, and the surface 964 includes detent-like recesses 966. Accordingly, when the rail arm 930 and slide rail 928 are relatively positioned such that the post 962 is forced into a recess 966, the bias holding the post 962 within the recess 966 must be overcome in order to force the slide rail 928 to move relative to the rail arm 930.

More specifically, the recesses 966 include a first recess 966a, and the slide arm 928 may be retracted to a position where the post 962 is located within the first recess 966a and the slide arm 928 is clear of the hook 840. Moreover, in this retracted position, the bracket arms 944 are aligned with spaces 970 in the proximal end 949a of the rail guides 949 such that the slide arm 928 may be removed from the rail arm 930, such as for cleaning.

A second recess 966b may be provided into which the post 962 may be located when the slide arm 928 is extended a short distance relative to the rail arm 930. In this position, the slide arm 928 and rail arm 930 are generally secured to each other, and the slide arm 928 is clear of the hook 840 such that a trial spacer 850 may be removed or attached to the trial spacer instrument 900.

A third recess 966c is provided when the slide arm 928 is extended such that the post 962 is moved from the second recess 966b to the third recess 966c. In this position, the trial spacer 840 attached to the trial spacer instrument 900 is permitted to rotate 0-45°.

Lastly, a fourth recess 966d may be provided. The slide arm 928 may be fully extended such that the trial spacer 940 is secured therein and generally locked in a particular orientation. As such, the post 962 is located within the recess 966d.

Figure 67:
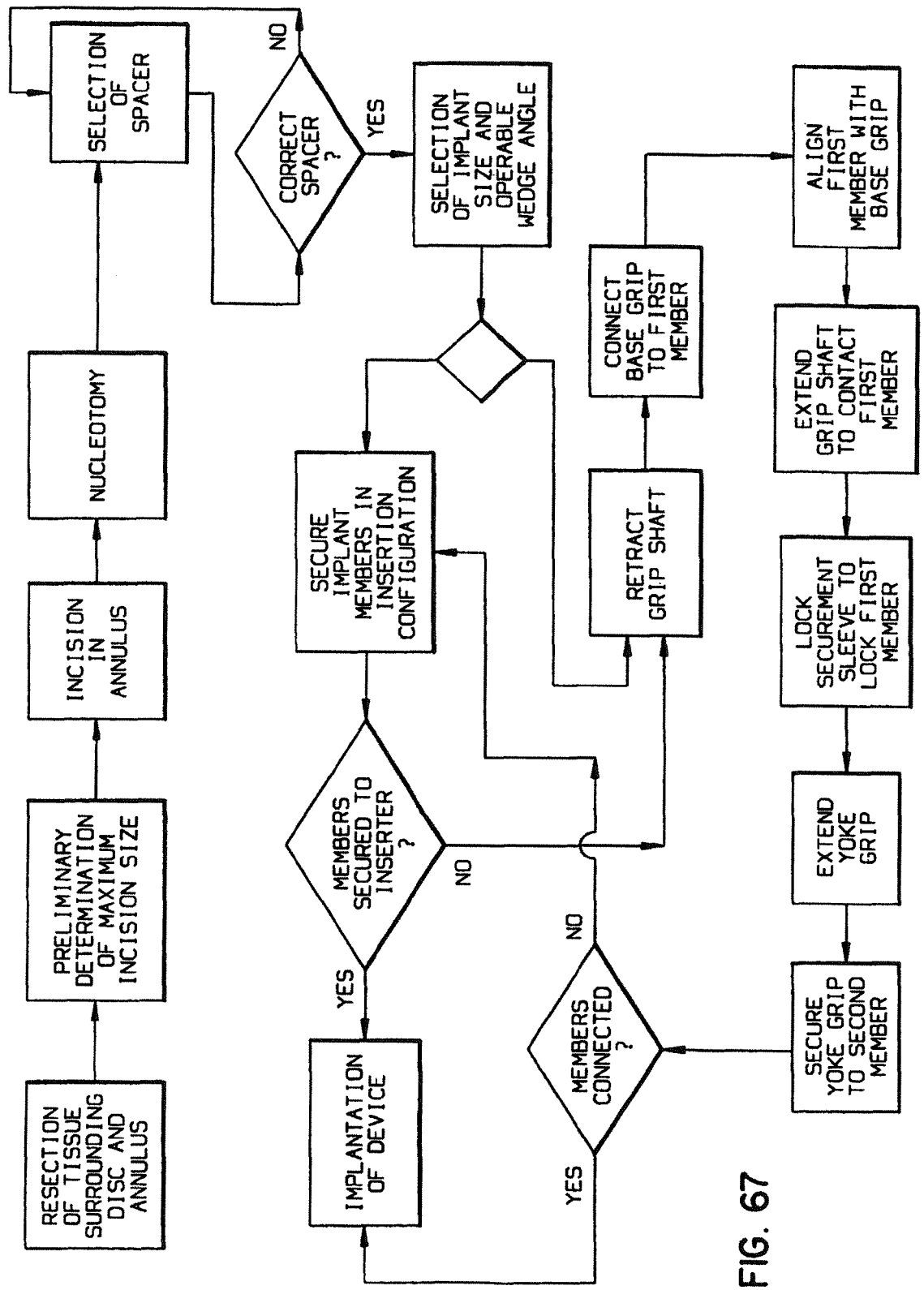
FIG. 67 is a flowchart illustrating a method of preparing to implant an artificial disc device within a spine in accordance with the present invention.
Figure 68:
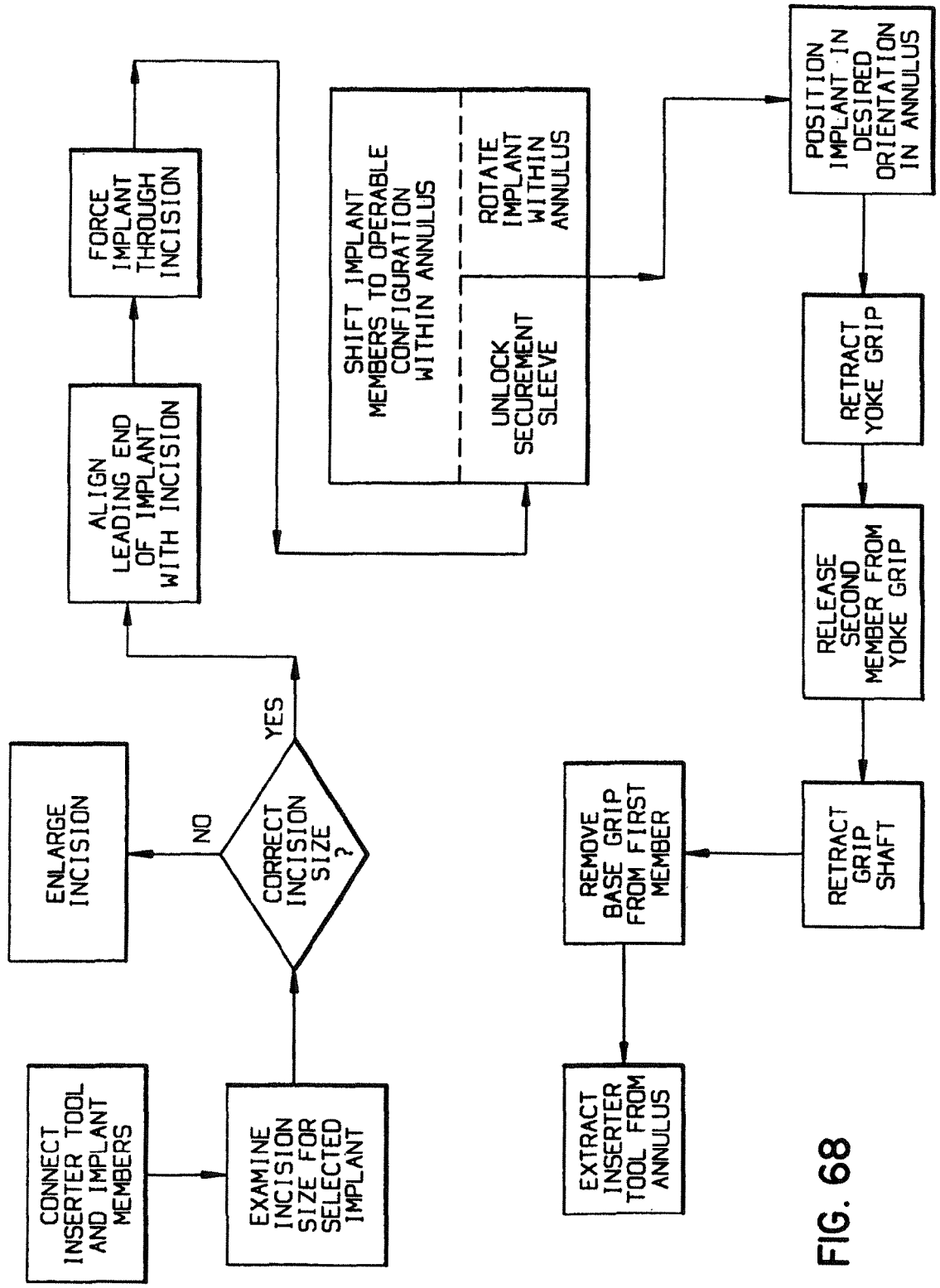
FIG. 68 is a flowchart illustrating a method of implanting an artificial disc device within the spine in accordance with the present invention.

A representative surgical technique is illustrated in FIGS. 67 and 68. Specifically, the technique includes resection of the tissue surrounding the damaged spinal disc to expose the annulus. A preliminary determination is made for the size of the artificial disc device to be implanted or, alternatively, a minimum incision size is selected. The annulus is then incised through to the interior of the disc to a depth sufficient to reach the nucleus. At least a portion of the nuclear material is then removed to provide a cavity within the annulus for receiving the artificial disc device. A trial spacer is then selected and secured to a trial spacer instrument, which is then guided into the incision. Examination of the fit of the trial spacer, if the cavity permits the trial spacer entrance, is performed to determine if the trial spacer accurately measures the cavity size and shape, including operable angle θ. If the trial spacer is not optimal based on available trial spacers and corresponding implants, additional trial spacers are selected and inserted within the cavity until the proper trial spacer is determined. Once the proper trial spacer is determined, an implant is selected based on the trial spacer. That is, an artificial disc device is selected for its size and operable angle θ based on the trial spacer determined to be proper.

The artificial disc device is then configured to its insertion configuration, and it is attached to the inserter instrument or tool. The artificial disc device may be configured first and then attached to the inserter tool, or vice versa.

To configure the implant in the insertion configuration, the cooperating structures of the implant are connected such that the leading end of the implant is relatively small and the implant forms a wedge-angle. For instance, a first member having a winged dove-tail may be positioned close to a second member having a recess with a structure mating with that of the dove-tail. Manual pressure is then be applied to the members to force the dove-tail within the recess. Alternatively, the dove-tail may be slid into an open end of the recess to join the recess and the dove-tail. As described above, other connecting or cooperating structures may be utilized to connected the members of the implant.

The inserter instrument may connect to the first and second members of the implant. The inserter instrument may include a projection on a first grip member wherein the projection is pivotally received within a recess formed in the first implant member. To insert the projection into the recess, a second grip member in the form of the above-described grip shaft is retracted, and the projection is inserted into the recess. The grip shaft is then released, and, having a forward spring-bias, the grip shaft shifts forward and contacts the first implant member. The first implant member is then aligned with the grip shaft so that an arcuate surface on the first implant member receives an arcuate shaft tip in a mating relationship. The securement sleeve is then shifted rearwardly and rotated so as to lock the grip shaft against the arcuate surface on the first implant member. The yoke grip of the inserter instrument is then extended. The yoke grip receives and secures on a post located on the second implant member. The post and/or opposed yoke arms flex to permit the post to be captured within the yoke grip.

Once the first and second implant members are secured to the inserter tool, the implant is ready for implantation. The size of the incision in the annulus is examined to ensure it is large enough for the selected implant. If not, the incision is enlarged. Otherwise, the smaller, leading end of the implant is aligned with the incision in the annulus. Force is then applied to direct the implant into and through the incision and into the nuclear cavity.

As the implant is being inserted, the outer surfaces of the first and second members contact the annulus and the vertebral endplates. As the force increases, this contact causes the cooperating structures providing the connection between the first and second implant members to release. This may occur at any point during the insertion. In this manner, the implant members are shifted from the insertion configuration to the operable configuration where the members are free to pivot and rotate relatively to each other within the nuclear cavity.

Subsequent to or simultaneously with the shifting to the operable configuration, the implant is rotated. More specifically, the securement sleeve is unlocked so that the grip shaft may retract. The shaft tip is then permitted to cam from the arcuate surface in which it was initially aligned to side arcuate surfaces positioned adjacent to the initial arcuate surface. In this manner, the implant is movably secured to the inserter instrument such that the implant may be rotated to be aligned in a proper orientation. Additionally, the inserter instrument may continue to insert and manipulate the implant. The implant is then adjusted to the desired position or orientation with the nuclear cavity. As described above, radio-opaque markers may be utilized on the implant members to facilitate a surgeon using radiographic equipment to examine and position the implant.

Once the implant is in the desired position and orientation, the inserter tool may be removed. More specifically, the yoke grip is retracted so that the post is forced from the yoke arms, such as by contact with a relatively stationary structure on the base grip. The grip shaft is then retracted so that the shaft tip is retracted from the first implant member, and so that the grip shaft itself is clear of the first implant member. The projection on the base grip is then removed from the recess in the first implant member. At this point, the inserter tool may be removed from the annulus and from the surgical site in general.

Natural discs is the lumbar area are presently reported as having a typical range of motion. The average range of motion for flexion/extension is 12-17 degrees, the average for lateral bending is 6-16 degrees, and the average for axial rotation is 2-3 degrees. In the present embodiments, the flexion/extension range is 15-20 degrees, the lateral bending is in the order of 7.5-8, and there is no restriction on axial rotation.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

The invention claimed is:

1. A method of replacing a nucleus of a spinal disc, the steps including:

providing an implant device comprising distinct upper and lower disc members having mating inner arcuate bearing surfaces configured to slidingly engage one another to allow the disc members to shift polyaxially with respect to one another and each having a major dimension extending along a longitudinal axis and a minor dimension transverse to the longitudinal axis;

forming an opening in an annulus of the spinal disc having a predetermined size and defining an insertion axis about which the opening extends;

attaching the upper disc member to a distal end of an inserter instrument at a tool engaging portion of the upper disc member to form a pivotal connection therebetween;

attaching the lower disc member to the distal end of the inserter instrument at a tool engaging portion of the lower disc member to form a pivotal connection therebetween such that each one of the upper and lower disc members is held independently of the other one of the upper and lower disc members by the inserter instrument in a superimposed orientation such that the distinct upper and lower disc members are kept from separating, and each one of the upper and lower disc members is configured to be pivoted about its respective pivotal connection at the distal end of the inserter instrument;

orienting the device with the longitudinal axis aligned with the insertion axis of the opening to keep the predetermined opening size to a minimum;

inserting the device through the opening into the nuclear space along the insertion axis; and pivoting the device relative to the distal end of the inserter instrument while the device is attached thereto within the nuclear space so that the longitudinal axis of the implant device is transverse to the insertion axis;

releasing the distinct upper and lower disc members from the distal end of the inserter instrument in the nuclear space.

2. The method of claim 1 wherein the step of forming an opening includes incising a portion of the annulus at an angle oblique to an anterior-posterior direction of the spinal disc.

3. The method of claim 1 further including fixedly securing the device in a predetermined orientation relative to the inserter instrument prior to the step of inserting the device.

4. The method of claim 3 wherein the inserter instrument includes a grip member, and the step of fixedly securing the device includes securing the grip member with the device.

5. The method of claim 4 further including the step of adjusting the grip member after the step of insertion such that the inserter instrument and the implant device may pivot relatively to each other.

6. The method of claim 1 wherein the step of forming an opening includes sizing the opening based on at least the minor dimension of the device.

7. The method of claim 1 further including selecting the device based on one of a size of the spinal disc, an angle formed between the upper and lower vertebrae, and the size of a nuclear cavity.

8. The method of claim 7 further including inserting a trial spacer within the nuclear cavity to select the implant device.

9. The method of claim 8 wherein the step of inserting the trial spacer includes utilizing a trial spacer instrument to direct the trial spacer within the annulus.

10. The method of claim 1 wherein the pivoting of the device occurs during the step of inserting the device.

11. The method of claim 1 wherein the pivoting of the device includes contacting an interior wall of the annulus to slide and position the device therewithin.

12. The method of claim 1, wherein the tool engaging portions of the upper and lower disc members comprise post members, and attaching the upper and lower disc members to the distal end of the inserter instrument comprises receiving each of the post members of the upper and lower disc members with corresponding post member receiving portions of the inserter tool.

* * * * *